United States Patent [19]

Drumm, III et al.

[11] Patent Number: 5,378,708
[45] Date of Patent: Jan. 3, 1995

[54] INSECTICIDAL, ACARICIDAL AND FUNGICIDAL AMINOPYRIMIDINES

[75] Inventors: Joseph E. Drumm, III, Newark; Renee M. Lett, Wilmington; Thomas M. Stevenson, Newark, all of Del.

[73] Assignee: E. I. Du Pont de Nemours and Company, Wilmington, Del.

[21] Appl. No.: 50,263

[22] PCT Filed: Nov. 13, 1991

[86] PCT No.: PCT/US91/08241
§ 371 Date: May 13, 1993
§ 102(e) Date: May 13, 1993

[87] PCT Pub. No.: WO92/08704
PCT Pub. Date: May 29, 1992

Related U.S. Application Data

[63] Continuation-in-part of Ser. No. 615,509, Nov. 19, 1990, abandoned.

[51] Int. Cl.⁶ .................. C07D 239/42; C07D 407/12; C07D 409/12; A01N 43/54
[52] U.S. Cl. .................. 514/256; 544/326; 544/327; 544/328; 544/329; 544/225; 544/229; 544/122
[58] Field of Search ............... 544/326, 327, 328, 329, 544/225, 229, 122; 514/256

[56] References Cited

U.S. PATENT DOCUMENTS

| | | | |
|---|---|---|---|
| 2,994,637 | 8/1961 | Bimber | 167/33 |
| 3,426,019 | 2/1969 | Pachter | 260/240 |
| 4,435,402 | 3/1984 | Tsuji et al. | 424/251 |
| 4,895,849 | 1/1990 | Yashioka et al. | 514/241 |
| 4,985,426 | 1/1991 | Yoshioka et al. | 514/241 |

FOREIGN PATENT DOCUMENTS

| | | |
|---|---|---|
| 196524 | 10/1986 | European Pat. Off. |
| 264217 | 4/1988 | European Pat. Off. |
| 323757 | 7/1989 | European Pat. Off. |
| 326328 | 8/1989 | European Pat. Off. |
| 326329 | 8/1989 | European Pat. Off. |
| 326331 | 8/1989 | European Pat. Off. |
| 370704 | 5/1990 | European Pat. Off. |
| 424125 | 4/1991 | European Pat. Off. |

OTHER PUBLICATIONS

Kristiansen et al, Chemical Abstracts, vol. 117, entry 7945e (1992).
Drumm et al., Chemical Abstracts, vol. 117, entry 69881q (1992).
Paegle et al., Chemical Abstracts, vol. 75, entry 49531m (1971).

*Primary Examiner*—John M. Ford
*Attorney, Agent, or Firm*—James A. Costello

[57] ABSTRACT

Compounds of the formula:

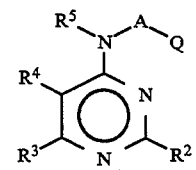

wherein A, Q and $R^2$ to $R^5$ are as defined in the text, compositions containing them and methods for using them to control insects, acarids and fungi.

19 Claims, No Drawings

INSECTICIDAL, ACARICIDAL AND FUNGICIDAL AMINOPYRIMIDINES

CROSS-REFERENCE TO RELATED APPLICATIONS

This application is a 371 of PCT/US91/08241, filed Nov. 13, 1991, which is a continuation-in-part of application Ser. No. 07/615,509, filed on Nov. 19, 1990, now abandoned.

BACKGROUND OF THE INVENTION

1. Field of the Invention

This invention concerns aralkylamino-pyrimidines, pesticidal compositions containing said compounds and use of the compounds to control pests.

2. State of the Art

U.S. Pat. No. 4,895,849 discloses aralkylaminopyrimidine derivatives of Formula I as insecticides, acaricides and fungicides

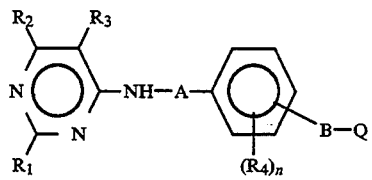

wherein:
A is an alkylene group optionally substituted with one or two substituents selected from the group alkynyl, haloalkyl, alkoxy, alkylthio and $C_3$-$C_5$ cycloalkyl.

EPA 370,704 discloses aralkylaminopyrimidine derivatives of the formula

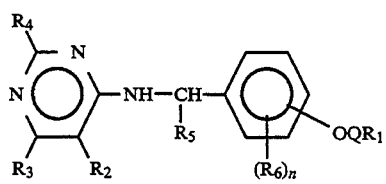

wherein:
$R_5$ is H, lower alkyl, cycloalkyl or lower haloalkyl.

EP 323,757 discloses alkylaminopyrimidine derivatives, process for producing the same, and insecticide, acaricide and fungicides containing the same as an active ingredient.

U.S. Pat. No. 4,435,402 discloses aminopyrimidine derivatives, processes for their preparation, and fungicidal, insecticidal and acaricidal compositions containing them.

EP 196,524 discloses phenoxyalkylamino-pyrimidine derivatives.

SUMMARY OF THE INVENTION

The invention pertains to compounds of Formula I, including all geometric and stereoisomers, agriculturally suitable salts thereof, agricultural compositions containing them and their use as insecticides, acaricides and fungicides in both agronomic and nonagronomic environments. The compounds of the invention are:

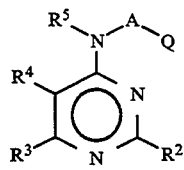

I wherein:
Q is selected from the group

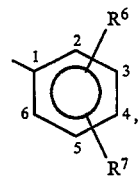

Q-1

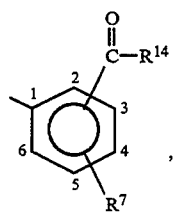

Q-2

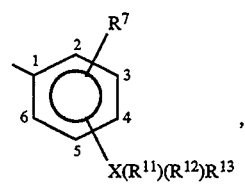

Q-3

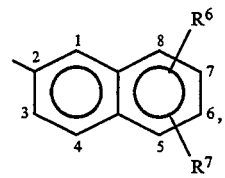

Q-4

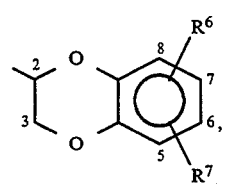

Q-5

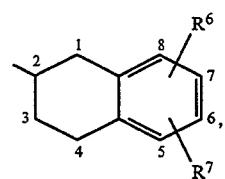

Q-6

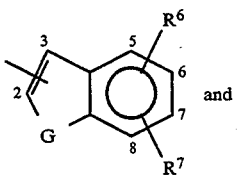

Q-7 and

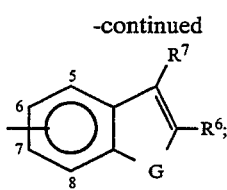

A is selected from the group $C_1$-$C_5$ alkylene and $C_3$-$C_6$ cycloalkylene, where any one atom of A can be optionally substituted with $R^1$;

G is O or S;

X is Si or Ge;

$R^1$ is selected from the group $C_1$-$C_2$ haloalkyl, CN, $C(O)R^8$, $CO_2R^8$, $C(O)N(R^8)R^9$, $N_3$, $NO_2$, $N(R^8)R^9$, $N(R^8)C(O)R^9$, $N(R^8)C(O)N(R^{10})R^9$, $N(R^8)S(O)_2R^{10}$, $OR^8$, $OC(O)R^8$, $OCO_2R^8$, $OC(O)N(R^8)R^9$, $OS(O)_2R^8$, $SR^8$, $S(O)R^8$, $S(O)_2R^8$ and SCN; provided that when $R^1$ is $N(R^8)S(O)_2R^{10}$, then $R^{10}$ is other than H and when $R^1$ is $OC(O)R^8$, $OCO_2R^8$, $OS(O)_2R^8$, $S(O)R^8$ or $S(O)_2R^8$, then $R^8$ is other than H;

$R^2$ is selected from the group H, halogen, $C_1$-$C_4$ alkyl and $C_1$-$C_4$ haloalkyl;

$R^3$ is selected from the group H, halogen, $C_1$-$C_6$ alkyl, $C_1$-$C_6$ haloalkyl, $C_2$-$C_6$ alkoxyalkyl and $C_2$-$C_6$ alkylthioalkyl;

$R^4$ is selected from the group halogen, $C_1$-$C_6$ alkyl, $C_1$-$C_6$ haloalkyl, $C_2$-$C_6$ alkoxyalkyl and $C_2$-$C_6$ alkylthioalkyl;

$R^5$ is selected from the group H, HCO, $C_2$-$C_6$ alkoxyalkyl $C_2$-$C_6$ alkylcarbonyl, $C_2$-$C_6$ alkoxycarbonyl, $C_2$-$C_6$ haloalkoxycarbonyl, $C(O)R^{15}$, $R^{11}OC(O)N(R^{12})S—$, $R^{11}(R^{12})NS—$, and $SR^8$; or $R^5$ is $C_1$-$C_6$ alkyl optionally substituted with a group selected from halogen, CN, $NO_2$, $S(O)_nR^{11}$, $C(O)R^{11}$, $CO_2R^{11}$, $C_1$-$C_3$ haloalkoxy and phenyl optionally substituted by halogen, CN, or $C_1$-$C_2$ haloalkyl;

$R^6$ is selected from the group H, $C_1$-$C_6$ alkyl, $C_1$-$C_6$ alkoxy, $C_2$-$C_6$ alkoxyalkyl, $C_2$-$C_6$ alkoxyalkoxy, $C_2$-$C_6$ alkenyl, $C_2$-$C_6$ haloalkenyl, $C_2$-$C_6$ alkynyl, $C_2$-$C_6$ alkenyloxy, $C_2$-$C_6$ alkynyloxy, $C_3$-$C_6$ cycloalkyl, $C_3$-$C_6$ cycloalkylalkyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, phenyl optionally substituted with W and phenoxy optionally substituted with W;

$R^7$ is selected from the group H, halogen, CN, $NO_2$, $C_1$-$C_2$ alkyl, $C_1$-$C_2$ alkoxy and $CF_3$;

$R^8$ and $R^{10}$ are independently selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, phenyl optionally substituted with 1 to 3 substituents independently selected from W and benzyl optionally substituted with 1 to 3 substituents independently selected from W;

$R^9$ is selected from the group H and $C_1$-$C_4$ alkyl;

$R^8$ and $R^9$ can be taken together when attached to the same atom as $—(CH_2)_4—$, $—(CH_2)_5—$ or $—CH_2CH_2OCH_2CH_2—$;

$R^{11}$ and $R^{12}$ are independently selected from the group $C_1$-$C_4$ alkyl;

$R^{13}$ is selected from the group $C_1$-$C_4$ alkyl, $C_1$-$C_4$ alkoxyalkyl and phenyl optionally substituted with W;

$R^{14}$ is selected from the group $C_1$-$C_6$ alkyl, $C_1$-$C_6$ alkoxy, $C_1$-$C_6$ haloalkoxy, and phenyl or benzyl, each phenyl and benzyl optionally and independently substituted with 1 to 3 W;

$R^{15}$ is selected from the group

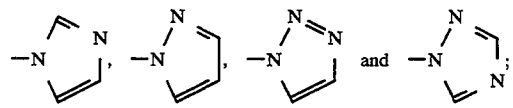

W is selected from the group halogen, CN, $NO_2$, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfonyl and $C_1$-$C_2$ haloalkylsulfonyl; and n is 0, 1 or 2;

provided that:
i) when Q is Q-1 and A is $C_1$-$C_5$ alkylene, then A is substituted with $R^1$;
ii) when Q is Q-1, A is $C_1$-$C_5$ alkylene and $R^1$ is $OR^8$ or $SR^8$, then $R^8$ is other than $C_1$-$C_6$ alkyl; and
iii) when Q is Q-1 and A is $C_1$-$C_5$ alkylene, then $R^1$ is other than $C_1$-$C_2$ haloalkyl.

Preferred Compounds A are those compounds of Formula I wherein:

A is $C_1$-$C_5$ alkylene;

G is S;

$R^1$ is selected from the group $OR^8$, $OC(O)R^8$ and $SR^8$;

$R^2$ is H;

$R^3$ is $C_1$-$C_6$ alkyl;

$R^4$ is halogen;

$R^5$ is selected from the group H and $CH_3$;

$R^6$ is selected from the group $C_1$-$C_6$ alkyl, $C_2$-$C_6$ alkoxyalkyl, $C_2$-$C_6$ alkoxyalkoxy and phenoxy optionally substituted with W;

$R^7$ is selected from the group H, halogen and $C_1$-$C_2$ alkyl;

$R^8$ is selected from the group H and $C_1$-$C_4$ alkyl;

$R^{11}$, $R^{12}$ and $R^{13}$ are independently selected from $C_1$-$C_2$ alkyl;

$R^{14}$ is selected form the group $C_1$-$C_4$ alkyl, $C_1$-$C_4$ alkoxy and phenyl each optionally substituted with 1 to 3 W; and W is selected from the group halogen and $C_1$-$C_2$ haloalkyl.

Preferred Compounds B are Compounds A wherein Q is Q-1.

Preferred Compounds C are Compounds A wherein Q is Q-2.

Preferred Compounds D are Compounds A wherein Q is Q-3.

Preferred Compounds E are Compounds A wherein Q is Q-4.

Preferred Compounds F are Compounds A wherein Q is Q-5.

Preferred Compounds G are Compounds A wherein Q is Q-6.

Preferred Compounds H are Compounds A wherein Q is Q-7.

Preferred Compounds I are Compounds A wherein Q is Q-8.

Specifically preferred for their biological activity and/or ease of synthesis are:

J. the compound of Preferred B which is β-[(5-chloro-6-ethyl-4-pyrimidinyl)amino]-4-(1,1dimethylethyl)-benzeneethanol;

K. the compound of Preferred D which is 5-chloro-6-ethyl-N-[2-[4-(trimethylsilyl)phenyl]ethyl]-4-pyrimidinamine;

L. the compound of Preferred E which is 5-chloro-6-ethyl-N-[2-(2-naphthalenyl)ethyl]-4-pyrimidinamine M. the compound of Preferred D which is 5-chloro-6-ethyl-N-[1-[4-(trimethylsilyl)phenyl]ethyl]-4-pyrimidinamine;

N. the compound of Preferred B which is β-[(5-chloro-6-ethyl-4-pyrimidinyl)amino]-4-(1,1-dimethymethyl)-benzenepropanol;

O. the compound of Preferred D which is 5-chloro-6-ethyl-N-methyl-N-[2-[4-trimethylsilyl)phenyl]ethyl]-4-pyrimidinamine; and P. the compound of Preferred D which is 5-chloro-6-ethyl-N-[2-[3-(trimethylsilyl)phenyl]ethyl]-4-pyrimidinamine.

In the above recitations, the term "alkyl" used either alone or in compound word such as "alkylthio", "alkylene", or "haloalkyl", denotes straight or branched alkyl, e.g., methyl, ethyl, n-propyl, isopropyl, or the different butyl, pentyl or hexyl isomers.

Alkoxy denotes methoxy, ethoxy, n-propyloxy, isopropyloxy and the different butoxy, pentoxy or hexyloxy isomers.

Alkenyl denotes straight or branched chain alkenes, e.g., vinyl, 1-propenyl, 2-propenyl, 3-propenyl and the different butenyl, pentenyl and hexenyl isomers. Alkynyl denotes straight chain or branched alkynes, e.g., ethynyl, 1-propynyl, 3-propynyl and the different butynyl, pentynyl and hexynyl isomers.

Alkylthio denotes methylthio, ethylthio and the different propylthio, butylthio, pentylthio and hexylthio isomers.

Alkylsulfinyl, alkylsulfonyl, alkylamino, etc., are defined analogously to the above examples.

Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$. The terms "halocycloalkyl", "haloalkenyl" and "haloalkynyl" are defined analogously to the term "haloalkyl".

The total number of carbon atoms in a substituent group is indicated by the "$C_i$-$C_j$" prefix where i and j are numbers from 1 to 8. For example, $C_1$-$C_3$ alkylsulfonyl designates methylsulfonyl through propylsulfonyl; $C_2$ alkoxyalkoxy designates $OCH_2OCH_3$; $C_4$ alkoxyalkoxy designates the various isomers of an alkoxy group substituted with a second alkoxy group containing a total of 4 carbon atoms, examples including $OCH_2OCH_2CH_2CH_3$ and $OCH_2CH_2OCH_2CH_3$; $C_2$ cyanoalkyl designates $CH_2CN$ and $C_3$ cyanoalkyl designates $CH_2CH_2CN$ and $CH(CN)CH_3$; $C_2$ alkylcarbonyl would designates $C(O)CH_3$ and $C_4$ alkylcarbonyl includes $C(O)CH_2CH_2CH_3$ and $C(O)CH(CH_3)_2$; and as a final example, $C_3$ alkoxycarbonylalkyl designates $CH_2CO_2CH_3$ and $C_4$ alkoxycarbonylalkyl includes $CH_2CH_2CO_2CH_3$, $CH_2CO_2CH_2CH_3$ and $CH(CH_3)CO_2CH_3$.

DETAILS OF THE INVENTION

Compounds of Formula I can be prepared according to the reaction shown in Scheme 1. In this scheme, Z represents a displaceable group such as a halogen atom, an alkylthio group, and an alkyl- or arylsulfonyloxy group.

SCHEME 1

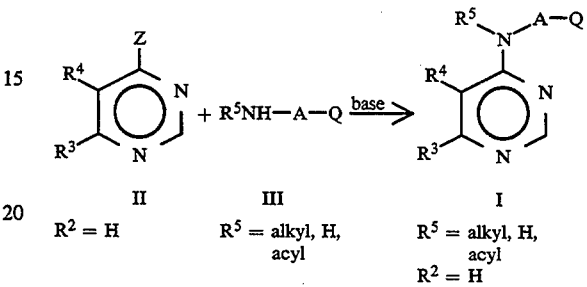

| II | III | I |
|---|---|---|
| $R^2$ = H | $R^5$ = alkyl, H, acyl | $R^5$ = alkyl, H, acyl $R^2$ = H |

The reaction of pyrimidine II with amine III is best carried out in the presence of an acid acceptor or base. The base can be, but is not limited to, triethylamine, pyridine, sodium hydride, or potassium carbonate. The synthetic process can be carried out in the absence or presence of a solvent. Suitable solvents include those that will not participate in the above reaction, for example, toluene, xylene, N,N-dimethylformamide, and N,N-dimethylacetamide. Preferred temperatures for this process are from about 20° C. to 200° C. with temperatures between 80° C. and 150° C. being particularly preferred.

Compounds of Formula I where $R^5$ is an alkyl or acyl group can be best prepared by reacting an amine of Formula III where $R^5$ is an alkyl or acyl group with a pyrimidine of Formula II. The amine of Formula III where $R^5$ is alkyl or acyl can be prepared by acylating or alkylating an amine of Formula III, where $R^5$ is equal to hydrogen, using conventional methods known to those skilled in the art.

Pyrimidines of Formula II can be prepared by a variety of literature methods. Some particularly efficient processes are described by Foster et al. in Org. Syn., 1955, 35, 80 and Ube Industries in JP 58(83) 222,070.

One particularly useful method for preparing some of the preferred compounds of this invention where Q is equal to Q-1 to Q-4, Q-7 and Q-8 is shown in Scheme 2.

SCHEME 2

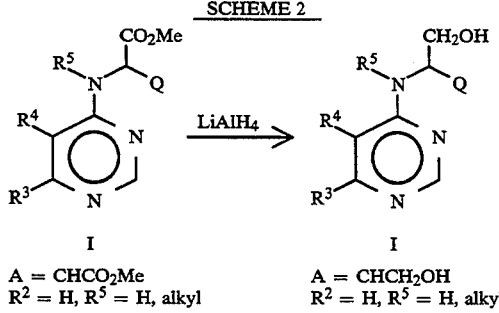

| I | I |
|---|---|
| A = CHCO$_2$Me | A = CHCH$_2$OH |
| $R^2$ = H, $R^5$ = H, alkyl | $R^2$ = H, $R^5$ = H, alkyl |

Reduction of esters of Formula I with a reducing agent, for example, Lithium aluminum hydride, gives an alcohol of Formula I where A is equal to CHCH$_2$OH. The reaction is best performed in an ether solvent that dissolves the starting ester (tetrahydrofuran) and at reduced temperatures (0° C.). Esters of Formula I where A is equal to CHCO$_2$Me can be prepared according to Scheme 1 using amines of Formula III where A is equal to CHCO$_2$Me. These reactions are usually performed in the presence of triethylamine in dimethylformamide at about 100° C. The requisite amine of Formula III can in turn be prepared by the process in Scheme 3.

SCHEME 3

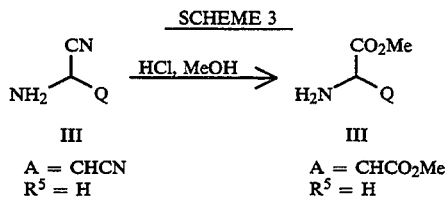

III
A = CHCN
R$^5$ = H

III
A = CHCO$_2$Me
R$^5$ = H

Hydrolysis of amine III where A is equal to CHCN with hydrogen chloride in methanol at the reflux temperature of the solvent proceeds to give an amine of Formula III where A is equal to CHCO$_2$Me. Finally, amines of Formula III where A is equal to CHCN can be synthesized from aldehydes of Formula IV according to the reaction in Scheme 4.

SCHEME 4

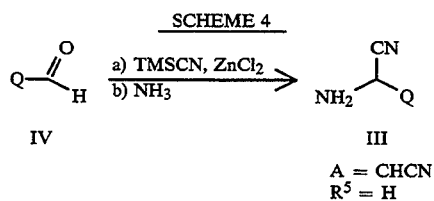

IV

III
A = CHCN
R$^5$ = H

Treatment of aldehydes of Formula IV with trimethylsilyl cyanide in the presence of zinc chloride in methylene chloride at ambient temperature leads to an intermediate which when further treated with ammonia in methanol at 40° C. gives the desired amino cyanide product. Aldehydes of Formula IV are either known compounds or can be prepared by conventional methods known to one skilled in the art.

Related compounds of Formula I where A is equal to CH(CO$_2$Me)CH$_2$ and Q is equal to Q-1 to Q-4, Q-7 and Q-8 can be prepared according to the procedures of O'Donnell etal. in *J. Org. Chem.*, 1982, 47, 2663 and Stork etal. in *J. Org. Chem.*, 1976, 41, 3491.

Another particularly useful method for preparing some of the preferred compounds of this invention where Q is equal to Q-1 to Q-4, Q-7 and Q-8 is shown in Scheme 5.

SCHEME 5

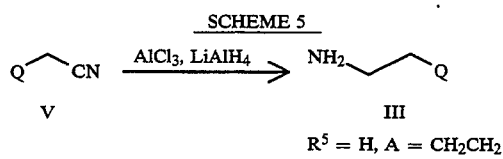

V

III
R$^5$ = H, A = CH$_2$CH$_2$

Amines of Formula III where A is equal to CH$_2$CH$_2$ can be prepared by reduction of nitriles of Formula V using alane. In situ formation of alane in ether and then treatment with nitrile V at 0° C. gives the desired primary amines in high yields. Nitriles of Formula V can in turn be synthesized by the displacement of a bromine atom from a bromide of Formula VI with potassium cyanide (Scheme 6).

SCHEME 6

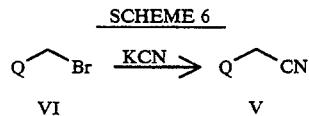

VI                V

This reaction can be accomplished in refluxing ethanol and water as cosolvents. Bromides of Formula VI where Q is equal to Q-1 to Q-4, Q-7 and Q-8 can be prepared according to the process shown in Scheme 7.

SCHEME 7

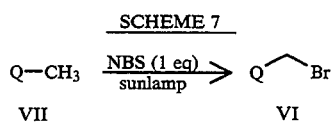

VII              VI

Aryl methyl groups in compounds of Formula VII are subject to free radical bromination by N-bromosuccinimide (NBS) in the presence of light. The reaction is commonly done in refluxing carbon tetrachloride with one equivalent of NBS. Compounds of Formula VII are either commercially available or can be prepared by conventional methods. Silylated compounds of Formula VII can be prepared according to the methods described by Habich et al. in Syn., 1979, 841. The germanylated compounds related to Formula VII can be made by simple modification of the procedure used for the silylated compounds that will be obvious to one skilled in the art.

Another particularly useful method for the preparation of some of the preferred compounds of this invention where Q is equal to Q-1 to Q-4, Q-7 and Q-8 is shown in Scheme 8.

SCHEME 8

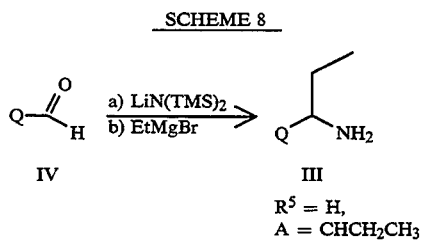

IV                III
                  R$^5$ = H,
                  A = CHCH$_2$CH$_3$

This process utilizes the method of Hart et al. described in *J. Org. Chem.*, 1983, 48, 289. Amines of Formula III where A is equal to CHCH$_2$CH$_3$ are prepared from aldehydes of Formula IV by treatment with lithium hexamethyldisilazide in THF at 0° C. followed by addition of ethyl Grignard and refluxing. Some aldehydes of Formula IV where Q is equal to Q-1 to Q-4, Q-7 and Q-8 can be prepared by reaction of dibromides of Formula VIII with silver nitrate in refluxing water/dimethoxyethane solvent (Scheme 9).

SCHEME 9

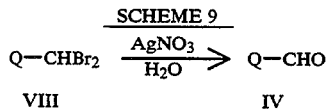

VIII              IV

The dibromides can, in turn, be prepared from compounds of Formula VII where Q is equal to Q-1 to Q-4, Q-7 and Q-8. Aryl methyl compounds of Formula VII are subject to free radical bromination with two equivalents of NBS in the presence of light in refluxing carbon tetrachloride (Scheme 10).

SCHEME 10

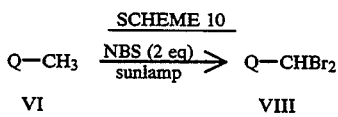

VI → VIII

The amines of Formula III prepared in Schemes 5 and can be used in Scheme 1 to prepare preferred compounds of Formula I where Q is equal to Q-1 to Q-4, Q-7 and Q-8 of this invention.

Compounds of Formula I where Q is equal to Q-5 can be prepared according to Scheme 1 wherein the amine of Formula III is synthesized according to the procedure of Henning et al. in *J. Med. Chem.*, 1987, 30, 814.

Compounds of Formula I where Q is equal to Q-6 can be prepared according to Scheme 1 wherein the amine of Formula III is synthesized according to the procedure of Gust et al., Tetrahedron, 1989, 45, 4867.

Compounds of Formula I where Q is equal to Q-2 and $R^1$ is equal to H can be made by Friedel-Crafts reaction of pyrimidinylamines of Formula IX with acid chlorides according to Scheme 11.

SCHEME 11

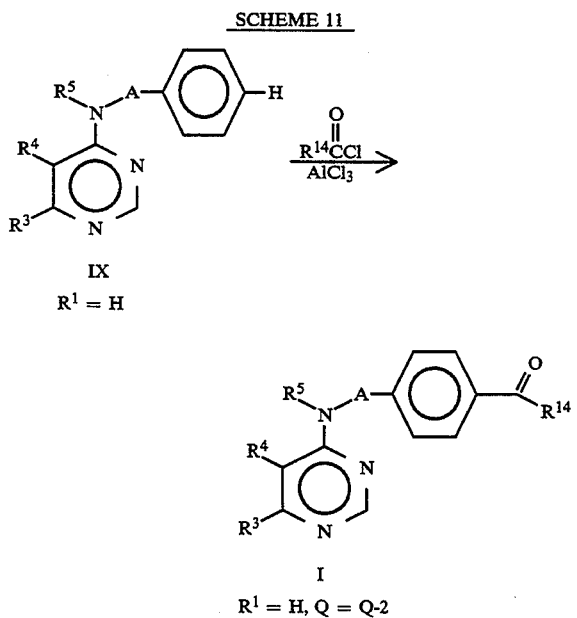

The pyrimidinylamines of Formula IX are known in the art (U.S. Pat. No. 4,435,402) or can be made by methods disclosed in this application. A wide variety of solvents, acids and acid chlorides can be used in the Friedel-Crafts acylation of the compounds of Formula IX. The Fridel-Crafts acylation of aromatic compounds is well known to those skilled in the art and a listing of suitable solvents, acids and reactions conditions can be found in "Friedel-Crafts and Related Reactions", Editor: George Olah, Interscience, New York 1964. Particularly suitable conditions for the instant invention are to use 1,2-dichloroethane as a solvent with aluminum trichloride as the acid. The reaction is generally carried out under an inert atmosphere at the reflux temperature of the solvent with a slight excess of the acid chloride.

Compounds of Formula I where Q is equal to Q-2 and $R^{14}$ is equal to alkoxy can be made by organometallic catalyzed carbonylation of compounds of Formula X according to Scheme 12.

SCHEME 12

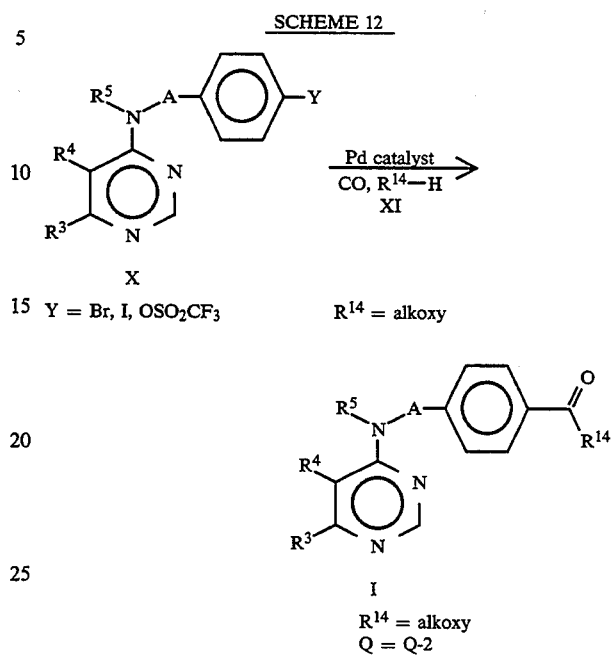

The reaction can be carried out with a variety of alcohols XI. Palladium complexes of triarylphosphines are the preferred catalysts in this reaction. The catalyst is generally used at 1–10% of the substrate concentration. Particularly preferred for its higher reactivity is the complex derived from palladium (II) acetate and bis(triphenylphosphino propane). Use of this catalyst for the carbonylation of aryl triflates and bromides has been reported by Dolle and Kruse *Chem. Comm.*, 1987, 904. The reaction can be carried out in a variety of solvents with dimethylsulfoxide being preferred for its higher catalyst turnover ratio. The temperature required for the reaction is determined by the nature of the catalyst and displaced halide or trillate. Generally the reaction is carried out at 70°–80° C. under a positive pressure of carbon monoxide. The presence of an acid scavenger is necessary for the reaction and a variety of inorganic and organic bases can serve this purpose. Triethylamine is particularly suitable for the present case.

The following examples illustrate the invention.

EXAMPLE 1

Step A

α-amino-4-(1,1-dimethylethyl)benzeneacetonitrile, hydrochloride

Trimethylsilylcyanide (24 mL, 0.18 mole) was added dropwise to a solution of p-tert-butylbenzaldehyde (25 g, 0.15 mole) and zinc iodide (0.5g, 1.5 mole) in methylene chloride while maintaining a temperature of 25° C. The yellow solution was stirred for 45 minutes and then concentrated to a viscous oil. The residue was treated with 250 mL of ammonia saturated methanol and heated at 40° C. for 1.5 hours. Concentration under vacuum gave a yellow solid which was dissolved in 250 mL of ether and dried over solid $MgSO_4$. After filtration, hydrogen chloride gas was bubbled through the ether solution for about 5 minutes while maintaining a temperature of 20°-25° C. The solid product was filtered and washed with ether and then dried under vacuum to give 28.9 g (86% yield), mp 190°-193° C.

$^1$H NMR (Me$_2$SO-d$_6$): δ 9.76 (s, 3H), 7.62, 7.54 (ABq, 4H), 5.94 (s, 1H), 1.29 (s, 9H).

Step B methyl α-amino-4-(1,1-dimethylethyl)benzeneacetate, hydrochloride

The product of Step A was dissolved in 40 mL of methanol and hydrogen chloride gas was bubbled into the solution while maintaining a temperature of 20°-30° C. The solution was refluxed for 2 hours, cooled to room temperature, and resaturated with HCl gas. After stirring at room temperature overnight, the reaction mixture was concentrated under vacuum and the residue triturated with ether to give a white solid. The solid product was collected by filtration and dried under vacuum (34 g, 99% yield), mp 185°-186° C.

$^1$H NMR (Me$_2$SO-d$_6$): δ 9.15 (s, 3H), 7.47 (s, 4H), 5.20 (s, 1H), 3.71 (s, 3H), 1.28 (s, 9H).

Step C methyl α-[(5-chloro-6-ethyl-4-pyrimidinyl)aminol-4-(1,1-dimethylethyl)benzeneacetate The ester from Step B (14.9 g, 58 mole) and 4,5-dichloro-6-ethylpyrimidine (10.3 g, 58 mole) were dissolved in a solution of triethylamine (18 mL, 0.13 mole) and dimethylformamide (40 mL) and heated at 100° C. for 6 hours. After cooling the solution was diluted with water and ether and partitioned. The aqueous phase was extracted three times with ether and the combined organic phases were washed two times with water, dried (MgSO$_4$) and concentrated. The crude residue was chromatographed on silica gel with 10% ethyl acetate/hexane. The resulting product was a waxy yellow solid (11.7 g, 56% yield).

$^1$H NMR (CDCl$_3$): δ 8.40 (s, 1H), 7.39 (s, 4H), 6.23 (d, 1H), 5.72 (d, 1H), 3.76 (s, 3H), 2.80 (q, 2H), 1.31 (s, 9H), 1.25 (t, 3H).

Step D

β-[(5-chloro-6-ethyl-4-pyrimidinyl)amino]-4-(1,1-dimethylethyl)benzeneethanol

The product of Step C (11.7 g, 32 mole) was dissolved in 80 mL of tetrahydrofuran and cooled to −5° C. with an ice/acetone bath. Lithium aluminum hydride (1.2 g, 32 mole) was added portionwise over 15 minutes in such a manner as to control gas evolution and maintain the temperature below 5° C. After complete addition of the LiAlH$_4$, the reaction was stirred at 0° C. for 30 minutes and then carefully quenched by dropwise addition of saturated aqueous Na$_2$SO$_4$ solution (10 mL). The mixture was diluted with ether and enough solid MgSO$_4$ was added to dry the suspension. Filtration and concentration of the ether solution gave a crude residue which was chromatographed on silica gel with 30% ethyl acetate/hexane. The title compound was obtained as a waxy white solid (7.9 g, 68% yield), mp 117°-119° C.

$^1$H NMR (CDCl$_3$): δ 8.39 (s, 1H), 7.39, 7.29 (ABq, 4H), 6.06 (d, 1H), 5.25 (m, 1H), 4.01 (d, 2H), 2.80 (q, 2H), 1.32 (s, 9H), 1.26 (t, 3H).

EXAMPLE 2

Step A 2-naphthaleneethanamine

Aluminum trichloride (7.6 g, 57 mmole) was added in portions to 30 mL of ether cooled to 0° C. under nitrogen. In a separate flask, lithium aluminum hydride (2.2 g, 57 mmole) was slurried in 30 mL of ether and cooled to −5° C. with an ice/acetone bath. The etherial aluminum trichloride solution was added dropwise to the LiAlH$_4$ slurry at such a rate as to maintain a temperature of 0° C. Fifteen minutes after addition was complete, 2-naphthylacetonitrile (4.0 g, 24 mmole) in 40 mL of ether was added dropwise while maintaining a temperature of 0° C. The reaction mixture was stirred for an additional 15 minutes at 0° C. and then allowed to warm to room temperature for 1 hour. After recooling to 0° C., the reaction was quenched by careful dropwise addition of water. The mixture was diluted with ether, partitioned, and the aqueous phase was basified with 30% NH$_4$OH solution. Extraction of the aqueous phase with ether, combination of the organic phases, drying, and concentration gave a colorless oil (2.7g, 67% yield).

$^1$H MNR (CDCl$_3$): δ 7.80 (m, 3H), 7.65 (s, 1H), 7.45 (m, 2H), 7.30 (m, 1H), 3.06 (t, 2H), 2.91 (t, 2H), 1.35 (s, 2H).

Step B 5-chloro-6-ethyl-N-[2-(2-naphthalenyl)ethyl]-4-pyrimidinamine

The product of Step A (0.68 g, 4.0 mmole) and 4,5-dichloro-6-ethylpyrimidine (0.71 g, 4.0 mmole) were dissolved in triethylamine (1.1 mL, 8.0 mmole) and toluene (7 mL) and heated to reflux for 4 hours. After cooling, the reaction mixture was treated with 20 mL of water and 30 mL of ether, partitioned, and the aqueous phase extracted with ether. The combined organic phases were dried (MgSO$_4$), concentrated and chromatographed on silica gel with 10% ethyl acetate/hexane. The title compound was obtained as a white solid (0.77 g, 62% yield), mp 81°-83° C.

$^1$H NMR (CDCl$_3$): δ 8.46 (s, 1H), 7.82 (m, 3H), 7.67 (s, 1H), 7.46 (m, 3H), 5.50 (t, 1H), 3.85 (q, 2H), 3.09 (t, 2H), 2.78 (q, 2H), 1.25 (t, 3H).

EXAMPLE 3

Step A 1-(dibromomethyl)-4-(trimethylsily)benzene

Trimethylsilyltoluene (5.0 g, 30 mmole), N-bromosuccinimide (11.4 g, 64 mmole), and a catalytic amount of benzoyl peroxide were dissolved in carbon tetrachloride (300 mL) and heated to reflux under irradiation by a sunlamp. After 1 hour a solid had formed and the reaction was complete. The reaction mixture was filtered and concentrated to give the desired product as a yellow liquid (10.7 g, 99% yield).

$^1$H NMR (CDCl$_3$): δ 7.53 (s, 4H), 6.64 (s, 1H), 0.27 (s, 9H).

Step B 4-(trimethylsilyl)benzaldehyde

The product of Step A (10 g, 30 mmole) was dissolved in dimethoxyethane (160 mL) and heated to reflux. A solution of silver nitrate (15.3 g, 90 mmole) in water (120 mL) was added dropwise while maintaining reflux. The reaction mixture was heated for 30 additional minutes and then cooled and the liquid decanted away from the percipitate. The solid was triturated with ether and the combined organic phases were washed once with water, dried (MgSO$_4$), and concentrated to give the desired product as a pale yellow oil (6 g, 99% yield).

$^1$H NMR (CDCl$_3$): δ 10.02 (s, 1H), 7.83, 7.70 (ABq, 4H), 0.31 (s, 9H).

Step C

α-ethyl-4-(trimethylsilyl)benzenemethanamine

To a solution of hexamethyldisilazane (4.3 mL, 20 mmole) in tetrahydrofuran (5 mL) at 0° C. was added n-butyllithium (8.4 mL of 2.5M, 21 mmole) dropwise. The mixture was allowed to warm to room temperature for 20 minutes and then recooled to 0° C. In a separate flask, the product of Step B (3.0 g, 17 mmole) in tetrahydrofuran (10 mL) was cooled to 0° C. The lithiohexamethyldisilazane solution was added via cannula to the aldehyde solution. The reaction mixture was warmed to 22° C. for 20 minutes and then ethyl magnesium bromide (14 mL of 3.0M, 42 mmole) was added dropwise. After heating the mixture at reflux for 12 hours, it was cooled and quenched with saturated aqueous ammonium chloride solution. The aqueous phase was separated and extracted with ether. Combination of the organic phases, drying (MgSO$_4$), and concentration gave a crude residue which was chromatographed on silica gel with ethyl acetate. The desired product was obtained as a colorless oil (0.95 g, 27% yield).

$^1$H NMR (CDCl$_3$): δ 7.48, 7.31 (ABq, 4H), 3.79. (t, 1H), 1.70 (t, 2H), 1.62 (s, 2H), 0.88 (t, 3H), 0.26 (s, 9H).

Step D 5-chloro-6-ethyl-N-[1-[4-(trimethylsilyl)phenyl]-propyl]-4-pyrimidinamine The amine of Step C (1.1 g, 5.3 mmole) was reacted as in Step B of Example 2 to give the title compound as a viscous oil (0.70 g, 38% yield).

$^1$H NMR (CDCl$_3$): δ 8.38 (s, 1H), 7.49, 7.32 (ABq, 4H), 5.65 (d, 1H), 5.15 (q, 1H), 2.78 (q, 2H), 1.93 (m, 2H), 1.25 (t, 3H), 0.96 (t, 3H), 0.26 (s, 9H).

EXAMPLE 4

Step A 1-ethyl-4-trimethylsilylbenzene

Magnesium(9.5 g, 0.39 mole) was suspended in THF (60 mL) at room temperature. A solution of 4-bromo-1-ethylbenzene (49 mL, 0.36 mole) in 300 mL of THF was added dropwise at such a rate as to maintain the temperature between 30° and 60° C. When the addition was complete the reaction mixture was stirred for an additional hour and then cooled to 30° C. Trimethylsilyl chloride (49 mL, 0.39 mole) was added dropwise at such a rate as to maintain the temperature between 30° and 40° C. The thin suspension was stirred overnight at room temperature. Saturated aqueous NH$_4$Cl was added and the reaction mixture partitioned. The aqueous phase was extracted three times with ether, and the combined organic phases were dried (MgSO$_4$) and concentrated. The resultant oil (60 g, 93% yield) was used in the next step without further purification.

$^1$H NMR (CDCl$_3$): δ 7.43, 7.22 (ABq, 4H), 2.64 (q, 2H), 1.24 (t, 3H), 0.25 (s, 9H).

Step B 1-bromo-1-[4-trimethylsilylphenyl]ethane

The product of Step A (59 g, 0.33 mole) was dissolved in carbon tetrachloride (700 mL). To this solution was added N-bromosuccinimide (59 g, 0.33 mole) and benzoyl peroxide (ca. 200 rag) in one portion. The reaction mixture was heated to reflux for 2.5 hours while being irradiated with a 275 watt sunlamp. After cooling, the solid succinimide was removed by filtration and the filtrate was washed with saturated aqueous NaHSO$_3$. Drying (MgSO$_4$) and concentration gave an oil (77 g, 91% yield) which was used in the next step without further purification.

$^1$H NMR (CDCl$_3$: δ 7.48, 7.43 (ABq, 4H), 5.20 (q, 1H), 2.07 (d, 3H), 0.26 (s, 9H).

Step C

1-[4-trimethylsilylphenyl]-1-N-phthalimidoethane

The product from Step B (77 g, 0.30 mole) and potassium phthalimide (58 g, 0.31 mole) were dissolved in DMF (300 mL). The reaction mixture was heated to 80° C. for one hour and then concentrated under vacuum at 80° C. to remove most of the: DMF. The residue was taken up in water and extracted three times with ether. The combined organic phases were washed two times with water, dried (MgSO$_4$) and concentrated to give an oil (91 g, 94% yield) which was used in the next step without further purification.

$^1$H NMR (CDCl$_3$): δ 7.80 (m, 2H), 7.69 (m, 2H), 7.49 (s, 4H), 5.57 (q, 1H), 1.93 (d, 3H), 0.23 (s, 9H).

Step D

α-methyl-4-trimethylsilylbenzenemethanamine

The product of Step C (91 g, 0.28 mole) and hydrazine monohydrate (14 mL, 0.29 mole) were dissolved in methanol (400 mL) and heated to reflux for two hours. After cooling, the reaction mixture was poured into 6% aqueous K$_2$CO$_3$ solution. The aqueous mixture was extracted three times with ether and the combined organic phases were dried (MgSO$_4$) and concentrated to give an oil (49 g, 90% yield) which was used in the next step without further purification.

$^1$H NMR (CDCl$_3$): δ 7.48, 7.35 (ABq, 4H), 4.10 (q, 1H), 1.65 (brs, 2H), 1.39 (d, 3H), 0.26 (s, 9H).

Step E 5-chloro-6-ethyl-N-[1-[4-(trimethylsilyl)phenyl]ethyl]-4-pyrimidinamine The product of Step D (17 g, 86 mole), 4,5-dichloro-6-ethylpyrimidine (15 g, 86 mole) and triethylamine (24 mL, 170 mole) were dissolved in toluene (65 mL). The reaction mixture was heated to reflux overnight and then cooled. Ether and water were added and the mixture was partitioned. The aqueous phase was extracted two times with ether and the combined organic phases were dried (MgSO$_4$) and concentrated. The resultant solid was recrystallized from acetonitrile to give the title compound as a white solid (17 g, 60% yield), mp 79°–80° C.

$^1$H NMR (CDCl$_3$): δ 8.40 (s, 1H), 7.51, 7.36 (ABq, 4H), 5.60 (brd, 1H), 5.37 (q, 1H), 2.78 (q, 2H), 1.60 (d, 3H), 1.25 (t, 3H), 0.26 (s, 9H).

EXAMPLE 5

Step A

4-[2-(4-bromophenyl)ethylaminol-5-chloro-6-ethylpyrimidine

4-Bromophenethylamine (4.4 g), 4,5-dichloro-6-ethylpyrimidine (2.5 g) and triethylamine (4 ml) were dissolved in dimethylacetamide (15 ml) and heated to 100°–120° C. for 4.5 h. The cooled solution was added to water (70 ml). The reaction mixture was filtered and the solid was dried by dissolution in methylene chloride and addition of magnesium sulfate. The residue was purified by column chromatography on silica gel in hexanes/ethyl acetate (4:1) to provide the product (3.4 g) which was used directly in the next step, mp 98°–99° C.

Step B

4-[2-[(5-chloro-6-ethyl-4-pyrimidinyl)amino]ethyl]benzoic acid, ethyl ester

The product from Step A (0.71 g) was dissolved in dimethylsulfoxide (6 ml) and treated with palladium acetate (35 rag), bis (diphenylphosphino)propane (70 mg), ethanol (4 ml) and triethylamine (0.5 ml). It was heated under an atmosphere of carbon monoxide to 70°–80° C. and held there for 6 h. The mixture was then cooled and treated with 30 ml of water. The solid formed was dissolved in methylene chloride and dried with magnesium sulfate. The residue was chromatographed on silica gel with hexanes/ethyl acetate (3:1) to give the desired product (0.5 g) as a solid, mp 134°–135° C.

NMR (CDCl$_3$, 200 Mhz) 8.4 (1H, ArH), 8.0 (1H, ArH), 7.3 (2H, ArH), 5.4 (NH), 4.4 (q, 2H, CH$_2$O), 3.8 (m, 2H, CH$_2$), 2.99 (m, 2H, CH$_2$), 1.4 (t, 3H, Me), 1.3 (t, 3H, Me).

EXAMPLE 6

(4-chlorophenyl)-4-[2-[(5-chloro-6-ethyl-4-pyrimidinyl)amino]ethyl]phenylmethanone A solution of 5-chloro-6-ethyl-4-(2-phenethylamino)-pyrimidine (0.84 g) in dichloroethane (15 ml) was treated with aluminum chloride (1.25 g). The mixture was treated with 4-chlorobenzoyl chloride (0.5 ml) and stirred for 1 h followed by heating at reflux for 1.5 h. The reaction mixture was cooled and treated with sodium hydroxide solution (20 ml, 1N), and methylene chloride (15 ml). The layers were separated and the organic layer was evaporated and the residue chromatographed on silica gel (hexanes/ethyl acetate 4:1) to give the product as an oil (0.72 g).

NMR (CDCl$_3$, 200 Mhz) 8.5 (1H, ArH), 7.7–7.3 (m, 8H, ArH), 5.6 (NH), 3.8 (m, 2H, CH$_2$), 3.0 (m, 2H, CH$_2$), 2.8 (m, 2H, CH$_2$), 1.3 (m, 3H, Me).

By the general procedures described herein, or obvious modifications thereof, the compounds of Index Tables A and B and Tables 1 through 9 can be prepared.

TABLE 1

| R$^5$ | R$^6$ | R$^5$ | R$^6$ |
|---|---|---|---|
| A = CHR$^1$; R$^1$ = CO$_2$Me | | A = CH(R$^1$)CH$_2$; R$^1$ = CO$_2$Me | |
| H | 4-tBu | H | 4-tBu |
| H | 4-CH$_2$CH$_2$OEt | H | 4-CH$_2$CH$_2$OEt |
| H | 4-OCH$_2$CH$_2$OEt | H | 4-OCH$_2$CH$_2$OEt |
| H | 4-OCH$_2$CF$_3$ | H | 4-OCH$_2$CF$_3$ |
| H | 4-CO$_2$tBu | H | 4-CO$_2$tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH$_2$CH$_2$OEt | Me | 4-CH$_2$CH$_2$OEt |
| Me | 4-OCH$_2$CH$_2$OEt | Me | 4-OCH$_2$CH$_2$OEt |
| Me | 4-OCH$_2$CF$_3$ | Me | 4-OCH$_2$CF$_3$ |
| Me | 4-CO$_2$tBu | Me | 4-CO$_2$tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH$_2$CH$_2$OEt | C(O)imidazole | 4-CH$_2$CH$_2$OEt |
| C(O)imidazole | 4-OCH$_2$CH$_2$OEt | C(O)imidazole | 4-OCH$_2$CH$_2$OEt |
| C(O)imidazole | 4-OCH$_2$CF$_3$ | C(O)imidazole | 4-OCH$_2$CF$_3$ |
| C(O)imidazole | 4-CO$_2$tBu | C(O)imidazole | 4-CO$_2$tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO$_2$Bu | 4-tBu | SN(Me)CO$_2$Bu | 4-tBu |
| SN(Me)CO$_2$Bu | 4-CH$_2$CH$_2$OEt | SN(Me)CO$_2$Bu | 4-CH$_2$CH$_2$OEt |
| SN(Me)CO$_2$Bu | 4-OCH$_2$CH$_2$OEt | SN(Me)CO$_2$Bu | 4-OCH$_2$CH$_2$OEt |
| SN(Me)CO$_2$Bu | 4-OCH$_2$CF$_3$ | SN(Me)CO$_2$Bu | 4-OCH$_2$CF$_3$ |
| SN(Me)CO$_2$Bu | 4-CO$_2$tBu | SN(Me)CO$_2$Bu | 4-CO$_2$tBu |
| SN(Me)CO$_2$Bu | 3-OPh | SN(Me)CO$_2$Bu | 3-OPh |
| SN(Me)CO$_2$Bu | 3-O—(4-F—Ph) | SN(Me)CO$_2$Bu | 3-O—(4-F—Ph) |
| A = CHR$^1$; R$^1$ = C(O)Me | | A = CH(R$^1$)CH$_2$; R$^1$ = C(O)Me | |
| H | 4-tBu | H | 4-tBu |
| H | 4-CH$_2$CH$_2$OEt | H | 4-CH$_2$CH$_2$OEt |
| H | 4-OCH$_2$CH$_2$OEt | H | 4-OCH$_2$CH$_2$OEt |
| H | 4-OCH$_2$CF$_3$ | H | 4-OCH$_2$CF$_3$ |
| H | 4-CO$_2$tBu | H | 4-CO$_2$tBu |
| H | 3-OPh | H | 3-OPh |
| H | 3-O—(4-F—Ph) | H | 3-O—(4-F—Ph) |
| Me | 4-tBu | Me | 4-tBu |

TABLE 1-continued

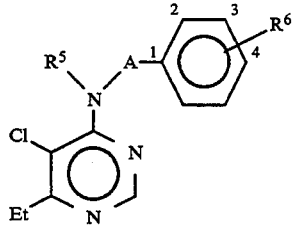

| R⁵ | R⁶ | R⁵ | R⁶ |
|---|---|---|---|
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |
| A = CHR¹; R¹ = S(O)Me | | A = CH(R¹)CH₂; R¹ = S(O)Me | |
| H | 4-tBu | H | 4-tBu |
| H | 4-CH₂CH₂OEt | H | 4-CH₂CH₂OEt |
| H | 4-OCH₂CH₂OEt | H | 4-OCH₂CH₂OEt |
| H | 4-OCH₂CF₃ | H | 4-OCH₂CF₃ |
| H | 4-CO₂tBu | H | 4-CO₂tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |
| A = CHR¹; R¹ = SCN | | A = CH(R¹)CH₂; R¹ = SCN | |
| H | 4-tBu | H | 4-tBu |
| H | 4-CH₂CH₂OEt | H | 4-CH₂CH₂OEt |
| H | 4-OCH₂CH₂OEt | H | 4-OCH₂CH₂OEt |
| H | 4-OCH₂CF₃ | H | 4-OCH₂CF₃ |
| H | 4-CO₂tBu | H | 4-CO₂tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |

TABLE 1-continued

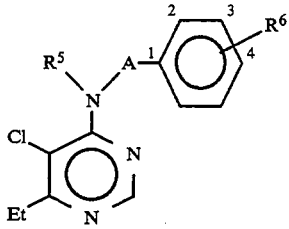

| R⁵ | R⁶ | R⁵ | R⁶ |
|---|---|---|---|
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |
| A = CHR¹; R¹ = CN | | A = CH(R¹)CH₂; R¹ = CN | |
| H | 4-tBu | H | 4-tBu |
| H | 4-CH₂CH₂OEt | H | 4-CH₂CH₂OEt |
| H | 4-OCH₂CH₂OEt | H | 4-OCH₂CH₂OEt |
| H | 4-OCH₂CF₃ | H | 4-OCH₂CF₃ |
| H | 4-CO₂tBu | H | 4-CO₂tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |
| A = CHR¹; R¹ = CH₂CN | | A = CH(R¹)CH₂; R¹ = CH₂CN | |
| H | 4-tBu | H | 4-tBu |
| H | 4-CH₂CH₂OEt | H | 4-CH₂CH₂OEt |
| H | 4-OCH₂CH₂OEt | H | 4-OCH₂CH₂OEt |
| H | 4-OCH₂CF₃ | H | 4-OCH₂CF₃ |
| H | 4-CO₂tBu | H | 4-CO₂tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |

TABLE 1-continued

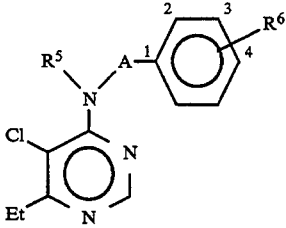

| R$^5$ | R$^6$ | R$^5$ | R$^6$ |
|---|---|---|---|
| A = CHR$^1$; R$^1$ = CH$_2$OC(Me)$_2$OMe | | A = CH(R$^1$)CH$_2$; R$^1$ = CH$_2$OC(Me)$_2$OMe | |
| H | 4-tBu | H | 4-tBu |
| H | 4-CH$_2$CH$_2$OEt | H | 4-CH$_2$CH$_2$OEt |
| H | 4-OCH$_2$CH$_2$OEt | H | 4-OCH$_2$CH$_2$OEt |
| H | 4-OCH$_2$CF$_3$ | H | 4-OCH$_2$CF$_3$ |
| H | 4-CO$_2$tBu | H | 4-CO$_2$tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH$_2$CH$_2$OEt | Me | 4-CH$_2$CH$_2$OEt |
| Me | 4-OCH$_2$CH$_2$OEt | Me | 4-OCH$_2$CH$_2$OEt |
| Me | 4-OCH$_2$CF$_3$ | Me | 4-OCH$_2$CF$_3$ |
| Me | 4-CO$_2$tBu | Me | 4-CO$_2$tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH$_2$CH$_2$OEt | C(O)imidazole | 4-CH$_2$CH$_2$OEt |
| C(O)imidazole | 4-OCH$_2$CH$_2$OEt | C(O)imidazole | 4-OCH$_2$CH$_2$OEt |
| C(O)imidazole | 4-OCH$_2$CF$_3$ | C(O)imidazole | 4-OCH$_2$CF$_3$ |
| C(O)imidazole | 4-CO$_2$tBu | C(O)imidazole | 4-CO$_2$tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO$_2$Bu | 4-tBu | SN(Me)CO$_2$Bu | 4-tBu |
| SN(Me)CO$_2$Bu | 4-CH$_2$CH$_2$OEt | SN(Me)CO$_2$Bu | 4-CH$_2$CH$_2$OEt |
| SN(Me)CO$_2$Bu | 4-OCH$_2$CH$_2$OEt | SN(Me)CO$_2$Bu | 4-OCH$_2$CH$_2$OEt |
| SN(Me)CO$_2$Bu | 4-OCH$_2$CF$_3$ | SN(Me)CO$_2$Bu | 4-OCH$_2$CF$_3$ |
| SN(Me)CO$_2$Bu | 4-CO$_2$tBu | SN(Me)CO$_2$Bu | 4-CO$_2$tBu |
| SN(Me)CO$_2$Bu | 3-OPh | SN(Me)CO$_2$Bu | 3-OPh |
| SN(Me)CO$_2$Bu | 3-O—(4-F—Ph) | SN(Me)CO$_2$Bu | 3-O—(4-F—Ph) |
| A = CHR$^1$; R$^1$ = CH$_2$OH | | A = CH(R$^1$)CH$_2$; R$^1$ = CH$_2$OH | |
| H | 4-tBu | H | 4-tBu |
| H | 4-CH$_2$CH$_2$OEt | H | 4-CH$_2$CH$_2$OEt |
| H | 4-OCH$_2$CH$_2$OEt | H | 4-OCH$_2$CH$_2$OEt |
| H | 4-OCH$_2$CF$_3$ | H | 4-OCH$_2$CF$_3$ |
| H | 4-CO$_2$tBu | H | 4-CO$_2$tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH$_2$CH$_2$OEt | Me | 4-CH$_2$CH$_2$OEt |
| Me | 4-OCH$_2$CH$_2$OEt | Me | 4-OCH$_2$CH$_2$OEt |
| Me | 4-OCH$_2$CF$_3$ | Me | 4-OCH$_2$CF$_3$ |
| Me | 4-CO$_2$tBu | Me | 4-CO$_2$tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH$_2$CH$_2$OEt | C(O)imidazole | 4-CH$_2$CH$_2$OEt |
| C(O)imidazole | 4-OCH$_2$CH$_2$OEt | C(O)imidazole | 4-OCH$_2$CH$_2$OEt |
| C(O)imidazole | 4-OCH$_2$CF$_3$ | C(O)imidazole | 4-OCH$_2$CF$_3$ |
| C(O)imidazole | 4-CO$_2$tBu | C(O)imidazole | 4-CO$_2$tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO$_2$Bu | 4-tBu | SN(Me)CO$_2$Bu | 4-tBu |
| SN(Me)CO$_2$Bu | 4-CH$_2$CH$_2$OEt | SN(Me)CO$_2$Bu | 4-CH$_2$CH$_2$OEt |
| SN(Me)CO$_2$Bu | 4-OCH$_2$CH$_2$OEt | SN(Me)CO$_2$Bu | 4-OCH$_2$CH$_2$OEt |
| SN(Me)CO$_2$Bu | 4-OCH$_2$CF$_3$ | SN(Me)CO$_2$Bu | 4-OCH$_2$CF$_3$ |
| SN(Me)CO$_2$Bu | 4-CO$_2$tBu | SN(Me)CO$_2$Bu | 4-CO$_2$tBu |
| SN(Me)CO$_2$Bu | 3-OPh | SN(Me)CO$_2$Bu | 3-OPh |
| SN(Me)CO$_2$Bu | 3-O—(4-F—Ph) | SN(Me)CO$_2$Bu | 3-O—(4-F—Ph) |
| A = CH$_2$CHR$^1$; R$^1$ = CH$_2$OH | | A = CH(R$^1$)CH$_2$CH$_2$; R$^1$ = CH$_2$OH | |
| H | 4-tBu | H | 4-tBu |
| H | 4-CH$_2$CH$_2$OEt | H | 4-CH$_2$CH$_2$OEt |
| H | 4-OCH$_2$CH$_2$OEt | H | 4-OCH$_2$CH$_2$OEt |
| H | 4-OCH$_2$CF$_3$ | H | 4-OCH$_2$CF$_3$ |
| H | 4-CO$_2$tBu | H | 4-CO$_2$tBu |
| H | 3-OPh | H | 3-OPh |
| H | 3-O—(4-F—Ph) | H | 3-O—(4-F—Ph) |
| Me | 4-tBu | Me | 4-tBu |

TABLE 1-continued

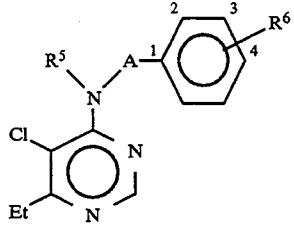

| R⁵ | R⁶ | R⁵ | R⁶ |
|---|---|---|---|
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |
| A = CHR¹; R¹ = CH(Me)OH | | A = CH(R¹)CH₂; R¹ = CH(Me)OH | |
| H | 4-tBu | H | 4-tBu |
| H | 4-CH₂CH₂OEt | H | 4-CH₂CH₂OEt |
| H | 4-OCH₂CH₂OEt | H | 4-OCH₂CH₂OEt |
| H | 4-OCH₂CF₃ | H | 4-OCH₂CF₃ |
| H | 4-CO₂tBu | H | 4-CO₂tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |
| A = CHR¹; R¹ = CH₂OCH₂CF₃ | | A = CH(R¹)CH₂; R¹ = CH₂OCH₂CF₃ | |
| H | 4-tBu | H | 4-tBu |
| H | 4-CH₂CH₂OEt | H | 4-CH₂CH₂OEt |
| H | 4-OCH₂CH₂OEt | H | 4-OCH₂CH₂OEt |
| H | 4-OCH₂CF₃ | H | 4-OCH₂CF₃ |
| H | 4-CO₂tBu | H | 4-CO₂tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |

TABLE 1-continued

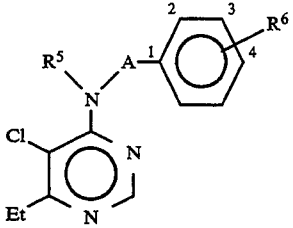

| R⁵ | R⁶ | R⁵ | R⁶ |
|---|---|---|---|
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |
| A = CHR¹; R¹ = CH₂NH₂ | | A = CH(R¹)CH₂; R¹ = CH₂NH₂ | |
| H | 4-tBu | H | 4-tBu |
| H | 4-CH₂CH₂OEt | H | 4-CH₂CH₂OEt |
| H | 4-OCH₂CH₂OEt | H | 4-OCH₂CH₂OEt |
| H | 4-OCH₂CF₃ | H | 4-OCH₂CF₃ |
| H | 4-CO₂tBu | H | 4-CO₂tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |
| A = CHR¹; R¹ = CH₂OC(O)Me | | A = CH(R¹)CH₂; R¹ = CH₂OC(O)Me | |
| H | 4-tBu | H | 4-tBu |
| H | 4-CH₂CH₂OEt | H | 4-CH₂CH₂OEt |
| H | 4-OCH₂CH₂OEt | H | 4-OCH₂CH₂OEt |
| H | 4-OCH₂CF₃ | H | 4-OCH₂CF₃ |
| H | 4-CO₂tBu | H | 4-CO₂tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |

TABLE 1-continued

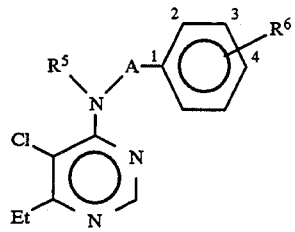

| R⁵ | R⁶ | R⁵ | R⁶ |
|---|---|---|---|
| A = CH₂CHR¹; R¹ = CH₂OC(O)Me | | A = CH(R¹)CH₂CH₂; R¹ = CH₂OC(O)Me | |
| H | 4-tBu | H | 4-tBu |
| H | 4-CH₂CH₂OEt | H | 4-CH₂CH₂OEt |
| H | 4-OCH₂CH₂OEt | H | 4-OCH₂CH₂OEt |
| H | 4-OCH₂CF₃ | H | 4-OCH₂CF₃ |
| H | 4-CO₂tBu | H | 4-CO₂tBu |
| H | 3-OPh | H | 3-OPh |
| H | 3-O—(4-F—Ph) | H | 3-O—(4-F—Ph) |
| Me | 4-tBu | Me | 4-tBu |
| Me | 4-CH₂CH₂OEt | Me | 4-CH₂CH₂OEt |
| Me | 4-OCH₂CH₂OEt | Me | 4-OCH₂CH₂OEt |
| Me | 4-OCH₂CF₃ | Me | 4-OCH₂CF₃ |
| Me | 4-CO₂tBu | Me | 4-CO₂tBu |
| Me | 3-OPh | Me | 3-OPh |
| Me | 3-O—(4-F—Ph) | Me | 3-O—(4-F—Ph) |
| C(O)imidazole | 4-tBu | C(O)imidazole | 4-tBu |
| C(O)imidazole | 4-CH₂CH₂OEt | C(O)imidazole | 4-CH₂CH₂OEt |
| C(O)imidazole | 4-OCH₂CH₂OEt | C(O)imidazole | 4-OCH₂CH₂OEt |
| C(O)imidazole | 4-OCH₂CF₃ | C(O)imidazole | 4-OCH₂CF₃ |
| C(O)imidazole | 4-CO₂tBu | C(O)imidazole | 4-CO₂tBu |
| C(O)imidazole | 3-OPh | C(O)imidazole | 3-OPh |
| C(O)imidazole | 3-O—(4-F—Ph) | C(O)imidazole | 3-O—(4-F—Ph) |
| SN(Me)CO₂Bu | 4-tBu | SN(Me)CO₂Bu | 4-tBu |
| SN(Me)CO₂Bu | 4-CH₂CH₂OEt | SN(Me)CO₂Bu | 4-CH₂CH₂OEt |
| SN(Me)CO₂Bu | 4-OCH₂CH₂OEt | SN(Me)CO₂Bu | 4-OCH₂CH₂OEt |
| SN(Me)CO₂Bu | 4-OCH₂CF₃ | SN(Me)CO₂Bu | 4-OCH₂CF₃ |
| SN(Me)CO₂Bu | 4-CO₂tBu | SN(Me)CO₂Bu | 4-CO₂tBu |
| SN(Me)CO₂Bu | 3-OPh | SN(Me)CO₂Bu | 3-OPh |
| SN(Me)CO₂Bu | 3-O—(4-F—Ph) | SN(Me)CO₂Bu | 3-O—(4-F—Ph) |

TABLE 2

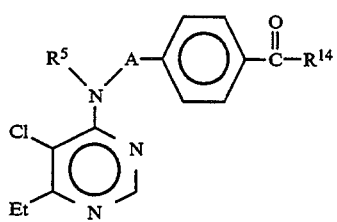

TABLE 2-continued

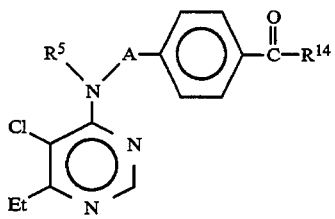

| A | R⁵ | A | R⁵ |
|---|---|---|---|
| R¹⁴ = OMe | | R¹⁴ = OMe | |
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |
| R¹⁴ = OEt | | R¹⁴ = OEt | |
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |
| R¹⁴ = OiPr | | R¹⁴ = OiPr | |
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |

TABLE 2-continued

[Structure: R⁵-N(A-phenyl-C(O)R¹⁴) attached to pyridine with Cl and Et substituents]

| | | | |
|---|---|---|---|
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

$R^{14} = Et$ / $R^{14} = Et$

| | | | |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

$R^{14} = Ph$ / $R^{14} = Ph$

| | | | |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

$R^{14} = 4\text{-}F\text{--}Ph$ / $R^{14} = 4\text{-}F\text{--}Ph$

| | | | |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

$R^{14} = 4\text{-}Cl\text{--}Ph$ / $R^{14} = 4\text{-}Cl\text{--}Ph$

TABLE 2-continued

| | | | |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

| $R^{14}$ | $R^{14}$ |
|---|---|
| $R^5 = H, A = CH_2CH_2$ | $R^5 = H, A = CH_2CH_2$ |
| Me | 2-F-phenyl |
| i-Pr | 3-F-phenyl |
| c-Pr | 2-Cl-phenyl |
| n-Bu | 3-Cl-phenyl |
| i-Bu | 2-CF₃-phenyl |
| t-Bu | 3-CF₃-phenyl |
| c-Bu | 4-CF₃-phenyl |
| n-amyl | 4-Me-phenyl |
| i-amyl | 4-OMe-phenyl |
| t-amyl | 2,4-di-F-phenyl |
| cyclopentyl | 3,4-di-F-phenyl |
| n-hexyl | 3,5-di-F-phenyl |
| cyclohexyl | 2,4-di-Cl-phenyl |
| —OCH₂CF₃ | 3,5-di-Cl-phenyl |
| —On-Pr | 3,4-di-Cl-phenyl |
| —On-Bu | |
| —Oi-Bu | |

TABLE 3

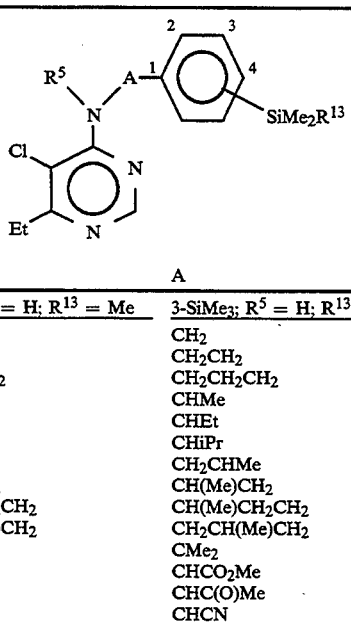

| A | A |
|---|---|
| 4-SiMe₃; $R^5 = H$; $R^{13} = Me$ | 3-SiMe₃; $R^5 = H$; $R^{13} = Me$ |
| CH₂ | CH₂ |
| CH₂CH₂ | CH₂CH₂ |
| CH₂CH₂CH₂ | CH₂CH₂CH₂ |
| CHMe | CHMe |
| CHEt | CHEt |
| CHiPr | CHiPr |
| CH₂CHMe | CH₂CHMe |
| CH(Me)CH₂ | CH(Me)CH₂ |
| CH(Me)CH₂CH₂ | CH(Me)CH₂CH₂ |
| CH₂CH(Me)CH₂ | CH₂CH(Me)CH₂ |
| CMe₂ | CMe₂ |
| CHCO₂Me | CHCO₂Me |
| CHC(O)Me | CHC(O)Me |
| CHCN | CHCN |

TABLE 3-continued

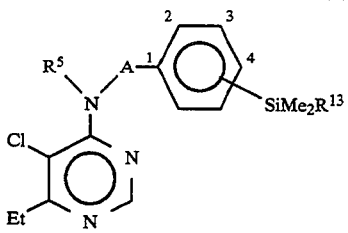 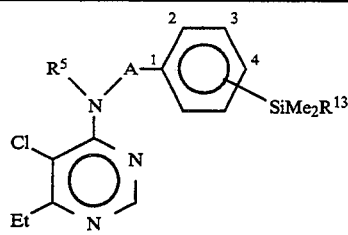

| A | A |
|---|---|
| CHCH2OH | CHCH2OH |
| CH(CH2OH)CH2 | CH(CH2OH)CH2 |
| 4-SiMe3; R5 = Me; R13 = Me | 3-SiMe3; R5 = Me; R13 = Me |
| CH2 | CH2 |
| CH2CH2 | CH2CH2 |
| CH2CH2CH2 | CH2CH2CH2 |
| CHMe | CHMe |
| CHEt | CHEt |
| CHiPr | CHiPr |
| CH2CHMe | CH2CHMe |
| CH(Me)CH2 | CH(Me)CH2 |
| CH(Me)CH2CH2 | CH(Me)CH2CH2 |
| CH2CH(Me)CH2 | CH2CH(Me)CH2 |
| CMe2 | CMe2 |
| CHCO2Me | CHCO2Me |
| CHC(O)Me | CHC(O)Me |
| CHCN | CHCN |
| CHCH2OH | CHCH2OH |
| CH(CH2OH)CH2 | CH(CH2OH)CH2 |
| 4-SiMe3; R5 = Et; R13 = Me | 3-SiMe3; R5 = Et; R13 = Me |
| CH2 | CH2 |
| CH2CH2 | CH2CH2 |
| CH2CH2CH2 | CH2CH2CH2 |
| CHMe | CHMe |
| CHEt | CHEt |
| CHiPr | CHiPr |
| CH2CHMe | CH2CHMe |
| CH(Me)CH2 | CH(Me)CH2 |
| CH(Me)CH2CH2 | CH(Me)CH2CH2 |
| CH2CH(Me)CH2 | CH2CH(Me)CH2 |
| CMe2 | CMe2 |
| CHCO2Me | CHCO2Me |
| CHC(O)Me | CHC(O)Me |
| CHCN | CHCN |
| CHCH2OH | CHCH2OH |
| CH(CH2OH)CH2 | CH(CH2OH)CH2 |
| 4-SiMe3; R5 = C(O)imidazole; R13 = Me | 3-SiMe3; R5 = C(O)imidazole; R13 = Me |
| CH2 | CH2 |
| CH2CH2 | CH2CH2 |
| CH2CH2CH2 | CH2CH2CH2 |
| CHMe | CHMe |
| CHEt | CHEt |
| CHiPr | CHiPr |
| CH2CHMe | CH2CHMe |
| CH(Me)CH2 | CH(Me)CH2 |
| CH(Me)CH2CH2 | CH(Me)CH2CH2 |
| CH2CH(Me)CH2 | CH2CH(Me)CH2 |
| CMe2 | CMe2 |
| CHCO2Me | CHCO2Me |
| CHC(O)Me | CHC(O)Me |
| CHCN | CHCN |
| CHCH2OH | CHCH2OH |
| CH(CH2OH)CH2 | CH(CH2OH)CH2 |
| 4-SiMe3; R5 = C(O)Me; R13 = Me | 3-SiMe3; R5 = C(O)Me; R13 = Me |
| CH2 | CH2 |
| CH2CH2 | CH2CH2 |
| CH2CH2CH2 | CH2CH2CH2 |
| CHMe | CHMe |
| CHEt | CHEt |
| CHiPr | CHiPr |
| CH2CHMe | CH2CHMe |
| CH(Me)CH2 | CH(Me)CH2 |
| CH(Me)CH2CH2 | CH(Me)CH2CH2 |
| CH2CH(Me)CH2 | CH2CH(Me)CH2 |
| CMe2 | CMe2 |
| CHCO2Me | CHCO2Me |
| CHC(O)Me | CHC(O)Me |
| CHCN | CHCN |
| CHCH2OH | CHCH2OH |
| CH(CH2OH)CH2 | CH(CH2OH)CH2 |
| 4-SiMe3; R5 = CH2CN; R13 = Me | 3-SiMe3; R5 = CH2CN; R13 = Me |
| CH2 | CH2 |
| CH2CH2 | CH2CH2 |
| CH2CH2CH2 | CH2CH2CH2 |
| CHMe | CHMe |
| CHEt | CHEt |
| CHiPr | CHiPr |
| CH2CHMe | CH2CHMe |
| CH(Me)CH2 | CH(Me)CH2 |
| CH(Me)CH2CH2 | CH(Me)CH2CH2 |
| CH2CH(Me)CH2 | CH2CH(Me)CH2 |
| CMe2 | CMe2 |
| CHCO2Me | CHCO2Me |
| CHC(O)Me | CHC(O)Me |
| CHCN | CHCN |
| CHCH2OH | CHCH2OH |
| CH(CH2OH)CH2 | CH(CH2OH)CH2 |
| 4-SiMe3; R5 = CH2OEt; R13 = Me | 3-SiMe3; R5 = CH2OEt; R13 = Me |
| CH2 | CH2 |
| CH2CH2 | CH2CH2 |
| CH2CH2CH2 | CH2CH2CH2 |
| CHMe | CHMe |
| CHEt | CHEt |
| CHiPr | CHiPr |
| CH2CHMe | CH2CHMe |
| CH(Me)CH2 | CH(Me)CH2 |
| CH(Me)CH2CH2 | CH(Me)CH2CH2 |
| CH2CH(Me)CH2 | CH2CH(Me)CH2 |
| CMe2 | CMe2 |
| CHCO2Me | CHCO2Me |
| CHC(O)Me | CHC(O)Me |
| CHCN | CHCN |
| CHCH2OH | CHCH2OH |
| CH(CH2OH)CH2 | CH(CH2OH)CH2 |
| 4-SiMe3; R5 = SNBu2; R13 = Me | 3-SiMe3; R5 = SNBu2; R13 = Me |
| CH2 | CH2 |
| CH2CH2 | CH2CH2 |
| CH2CH2CH2 | CH2CH2CH2 |
| CHMe | CHMe |
| CHEt | CHEt |
| CHiPr | CHiPr |
| CH2CHMe | CH2CHMe |
| CH(Me)CH2 | CH(Me)CH2 |
| CH(Me)CH2CH2 | CH(Me)CH2CH2 |
| CH2CH(Me)CH2 | CH2CH(Me)CH2 |
| CMe2 | CMe2 |
| CHCO2Me | CHCO2Me |
| CHC(O)Me | CHC(O)Me |
| CHCN | CHCN |
| CHCH2OH | CHCH2OH |
| CH(CH2OH)CH2 | CH(CH2OH)CH2 |
| 4-SiMe3; R5 = SN(Me)CO2Bu; R13 = Me | 3-SiMe3; R5 = SN(Me)CO2Bu; R13 = Me |
| CH2 | CH2 |
| CH2CH2 | CH2CH2 |
| CH2CH2CH2 | CH2CH2CH2 |
| CHMe | CHMe |
| CHEt | CHEt |
| CHiPr | CHiPr |
| CH2CHMe | CH2CHMe |

TABLE 3-continued

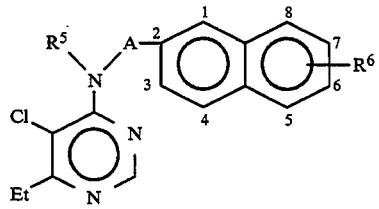

| A | A |
|---|---|
| CH(Me)CH$_2$ | CH(Me)CH$_2$ |
| CH(Me)CH$_2$CH$_2$ | CH(Me)CH$_2$CH$_2$ |
| CH$_2$CH(Me)CH$_2$ | CH$_2$CH(Me)CH$_2$ |
| CMe$_2$ | CMe$_2$ |
| CHCO$_2$Me | CHCO$_2$Me |
| CHC(O)Me | CHC(O)Me |
| CHCN | CHCN |
| CHCH$_2$OH | CHCH$_2$OH |
| CH(CH$_2$OH)CH$_2$ | CH(CH$_2$OH)CH$_2$ |
| 4-SiMe$_2$R$^{13}$; R$^5$ = H; R$^{13}$ = tBu | 4-SiMe$_2$R$^{13}$; R$^5$ = C(O)imidazole; R$^{13}$ = tBu |
| CH$_2$ | CH$_2$ |
| CH$_2$CH$_2$ | CH$_2$CH$_2$ |
| CHMe | CHMe |
| CHEt | CHEt |
| CHiPr | CHiPr |
| CH(Me)CH$_2$ | CH(Me)CH$_2$ |
| CHCH$_2$OH | CHCH$_2$OH |
| CH(CH$_2$OH)CH$_2$ | CH(CH$_2$OH)CH$_2$ |
| 4-SiMe$_2$R$^{13}$; R$^5$ = Me; R$^{13}$ = tBu | 4-SiMe$_2$R$^{13}$; R$^5$ = SN(Me)CO$_2$Bu; R$^{13}$ = tBu |
| CH$_2$ | CH$_2$ |
| CH$_2$CH$_2$ | CH$_2$CH$_2$ |
| CHMe | CHMe |
| CHEt | CHEt |
| CHiPr | CHiPr |
| CH(Me)CH$_2$ | CH(Me)CH$_2$ |
| CHCH$_2$OH | CHCH$_2$OH |
| CH(CH$_2$OH)CH$_2$ | CH(CH$_2$OH)CH$_2$ |
| 4-SiMe$_2$R$^{13}$; R$^5$ = H; R$^{13}$ = Ph | 4-SiMe$_2$R$^{13}$; R$^5$ = C(O)imidazole; R$^{13}$ = Ph |
| CH$_2$ | CH$_2$ |
| CH$_2$CH$_2$ | CH$_2$CH$_2$ |
| CHMe | CHMe |
| CHEt | CHEt |
| CHiPr | CHiPr |
| CH(Me)CH$_2$ | CH(Me)CH$_2$ |
| CHCH$_2$OH | CHCH$_2$OH |
| CH(CH$_2$OH)CH$_2$ | CH(CH$_2$OH)CH$_2$ |
| 4-SiMe$_2$R$^{13}$; R$^5$ = Me; R$^{13}$ = Ph | 4-SiMe$_2$R$^{13}$; R$^5$ = SN(Me)CO$_2$Bu; R$^{13}$ = Ph |
| CH$_2$ | CH$_2$ |
| CH$_2$CH$_2$ | CH$_2$CH$_2$ |
| CHMe | CHMe |
| CHEt | CHEt |
| CHiPr | CHiPr |
| CH(Me)CH$_2$ | CH(Me)CH$_2$ |
| CHCH$_2$OH | CHCH$_2$OH |
| CH(CH$_2$OH)CH$_2$ | CH(CH$_2$OH)CH$_2$ |
| 4-SiMe$_2$R$^{13}$; R$^5$ = H; R$^{13}$ = CH$_2$OEt | 4-SiMe$_2$R$^{13}$; R$^5$ = C(O)imidazole; R$^{13}$ = CH$_2$OEt |
| CH$_2$ | CH$_2$ |
| CH$_2$CH$_2$ | CH$_2$CH$_2$ |
| CHMe | CHMe |
| CHEt | CHEt |
| CHiPr | CHiPr |
| CH(Me)CH$_2$ | CH(Me)CH$_2$ |
| CHCH$_2$OH | CHCH$_2$OH |
| CH(CH$_2$OH)CH$_2$ | CH(CH$_2$OH)CH$_2$ |
| 4-SiMe$_2$R$^{13}$; R$^5$ = Me; R$^{13}$ = CH$_2$OEt | 4-SiMe$_2$R$^{13}$; R$^5$ = SN(Me)CO$_2$Bu; R$^{13}$ = CH$_2$OEt |
| CH$_2$ | CH$_2$ |
| CH$_2$CH$_2$ | CH$_2$CH$_2$ |
| CHMe | CHMe |
| CHEt | CHEt |

TABLE 3-continued

| A | A |
|---|---|
| CHiPr | CHiPr |
| CH(Me)CH$_2$ | CH(Me)CH$_2$ |
| CHCH$_2$OH | CHCH$_2$OH |
| CH(CH$_2$OH)CH$_2$ | CH(CH$_2$OH)CH$_2$ |

TABLE 4

| A | A |
|---|---|
| R$^5$ = H; R$^6$ = H | R$^5$ = Me; R$^6$ = H |
| CH$_2$ | CH$_2$ |
| CH$_2$CH$_2$ | CH$_2$CH$_2$ |
| CH$_2$CH$_2$CH$_2$ | CH$_2$CH$_2$CH$_2$ |
| CHMe | CHMe |
| CHEt | CHEt |
| CHiPr | CHiPr |
| CH$_2$CHMe | CH$_2$CHMe |
| CH(Me)CH$_2$ | CH(Me)CH$_2$ |
| CH(Me)CH$_2$CH$_2$ | CH(Me)CH$_2$CH$_2$ |
| CH$_2$CH(Me)CH$_2$ | CH$_2$CH(Me)CH$_2$ |
| CMe$_2$ | CMe$_2$ |
| CHCO$_2$Me | CHCO$_2$Me |
| CHC(O)ME | CHC(O)Me |
| CHCN | CHCN |
| CHCH$_2$OH | CHCH$_2$OH |
| CH(CH$_2$OH)CH$_2$ | CH(CH$_2$OH)CH$_2$ |
| R$^5$ = Et; R$^6$ = H | R$^5$ = C(O)imidazole; R$^6$ = H |
| CH$_2$ | CH$_2$ |
| CH$_2$CH$_2$ | CH$_2$CH$_2$ |
| CH$_2$CH$_2$CH$_2$ | CH$_2$CH$_2$CH$_2$ |
| CHMe | CHMe |
| R$^5$ = Et; R$^6$ = H | R$^5$ = C(O)imidazole; R$^6$ = H |
| CHEt | CHEt |
| CHiPr | CHiPr |
| CH$_2$CHMe | CH$_2$CHMe |
| CH(Me)CH$_2$ | CH(Me)CH$_2$ |
| CH(Me)CH$_2$CH$_2$ | CH(Me)CH$_2$CH$_2$ |
| CH$_2$CH(Me)CH$_2$ | CH$_2$CH(Me)CH$_2$ |
| CMe$_2$ | CMe$_2$ |
| CHCO$_2$Me | CHCO$_2$Me |
| CHC(O)Me | CHC(O)Me |
| CHCN | CHCN |
| CHCH$_2$OH | CHCH$_2$OH |
| CH(CH$_2$OH)CH$_2$ | CH(CH$_2$OH)CH$_2$ |
| R$^5$ = C(O)Me; R$^6$ = H | R$^5$ = CH$_2$CN; R$^6$ = H |
| CH$_2$ | CH$_2$ |
| CH$_2$CH$_2$ | CH$_2$CH$_2$ |
| CH$_2$CH$_2$CH$_2$ | CH$_2$CH$_2$CH$_2$ |
| CHMe | CHMe |
| CHEt | CHEt |
| CHiPr | CHiPr |
| CH$_2$CHMe | CH$_2$CHMe |
| CH(Me)CH$_2$ | CH(Me)CH$_2$ |
| CH(Me)CH$_2$CH$_2$ | CH(Me)CH$_2$CH$_2$ |
| CH$_2$CH(Me)CH$_2$ | CH$_2$CH(Me)CH$_2$ |
| CMe$_2$ | CMe$_2$ |
| CHCO$_2$Me | CHCO$_2$Me |

TABLE 4-continued

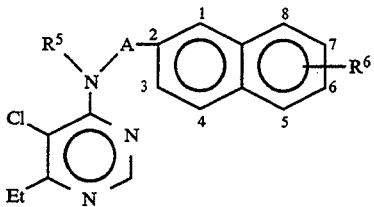

| A | A |
|---|---|
| CHC(O)Me | CHC(O)Me |
| CHCN | CHCN |
| CHCH2OH | CHCH2OH |
| CH(CH2OH)CH2 | CH(CH2OH)CH2 |
| R5 = CH2OEt; R6 = H | R5 = SNBu2; R6 = H |
| CH2 | CH2 |
| CH2CH2 | CH2CH2 |
| CH2CH2CH2 | CH2CH2CH2 |
| CHMe | CHMe |
| CHEt | CHEt |
| CHiPr | CHiPr |
| CH2CHMe | CH2CHMe |
| CH(Me)CH2 | CH(Me)CH2 |
| CH(Me)CH2CH2 | CH(Me)CH2CH2 |
| CH2CH(Me)CH2 | CH2CH(Me)CH2 |
| CMe2 | CMe2 |
| CHCO2Me | CHCO2Me |
| CHC(O)Me | CHC(O)Me |
| CHCN | CHCN |
| CHCH2OH | CHCH2OH |
| CH(CH2OH)CH2 | CH(CH2OH)CH2 |
| R5 = SN(Me)CO2Bu; R6 = H | R5 = H; R6 = 6-Cl |
| CH2 | CH2 |
| CH2CH2 | CH2CH2 |
| CH2CH2CH2 | CHMe |
| CHMe | CHEt |
| CHEt | CHiPr |
| CHiPr | CH(Me)CH2 |
|  | CHCH2OH |
|  | CH(CH2OH)CH2 |
| R5 = SN(Me)CO2Bu; R6 = H | R5 = H; R6 = 6-Cl |
| CH2CHMe | CH2 |
| CH(Me)CH2 | CH2CH2 |
| CH(Me)CH2CH2 | CHMe |
| CH2CH(Me)CH2 | CHEt |
| CMe2 | CHiPr |
| CHCO2Me | CH(Me)CH2 |
| CHC(O)Me | CHCH2OH |
| CHCN | CH(CH2OH)CH2 |
| CHCH2OH |  |
| CH(CH2OH)CH2 |  |
| R5 = C(O)imidazole; R6 = 6-Cl | R5 = H; R6 = 7-Cl |
| CH2 | CH2 |
| CH2CH2 | CH2CH2 |
| CHMe | CHMe |
| CHEt | CHEt |
| CHiPr | CHiPr |
| CH(Me)CH2 | CH(Me)CH2 |
| CHCH2OH | CHCH2OH |
| CH(CH2OH)CH2 | CH(CH2OH)CH2 |
| R5 = SN(Me)CO2Bu; R6 = 6-Cl | R5 = Me; R6 = 7-Cl |
| CH2 | CH2 |
| CH2CH2 | CH2CH2 |
| CHMe | CHMe |
| R5 = SN(Me)CO2Bu; R6 = 6-Cl | R5 = Me; R6 = 7-Cl |
| CHEt | CHEt |
| CHiPr | CHiPr |
| CH(Me)CH2 | CH(Me)CH2 |
| CHCH2OH | CHCH2OH |
| CH(CH2OH)CH2 | CH(CH2OH)CH2 |
| R5 = C(O)imidazole; R6 = 7-Cl | R5 = H; R6 = 6-F |
| CH2 | CH2 |
| CH2CH2 | CH2CH2 |
| CHMe | CHMe |
| CHEt | CHEt |
| CHiPr | CHiPr |
| CH(Me)CH2 | CH(Me)CH2 |
| CHCH2OH | CHCH2OH |

TABLE 4-continued

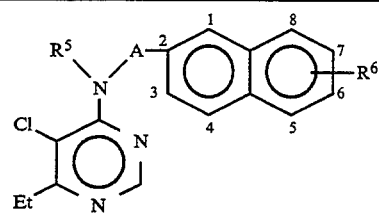

| A | A |
|---|---|
| CH(CH2OH)CH2 | CH(CH2OH)CH2 |
| R5 = SN(Me)CO2Bu; R6 = 7-Cl | R5 = Me; R6 = 6-F |
| CH2 | CH2 |
| CH2CH2 | CH2CH2 |
| CHMe | CHMe |
| CHEt | CHEt |
| CHiPr | CHiPr |
| CH(Me)CH2 | CH(Me)CH2 |
| CHCH2OH | CHCH2OH |
| CH(CH2OH)CH2 | CH(CH2OH)CH2 |
| R5 = C(O)imidazole; R6 = 6-F | R5 = H; R6 = 6-Me |
| CH2 | CH2 |
| CH2CH2 | CH2CH2 |
| CHMe | CHMe |
| CHEt | CHEt |
| CHiPr | CHiPr |
| CH(Me)CH2 | CH(Me)CH2 |
| CHCH2OH | CHCH2OH |
| CH(CH2OH)CH2 | CH(CH2OH)CH2 |
| R5 = SN(Me)CO2Bu; R6 = 6-F | R5 = Me; R6 = 6-Me |
| CH2 | CH2 |
| CH2CH2 | CH2CH2 |
| CHMe | CHMe |
| CHEt | CHEt |
| CHiPr | CHiPr |
| CH(Me)CH2 | CH(Me)CH2 |
| CHCH2OH | CHCH2OH |
| CH(CH2OH)CH2 | CH(CH2OH)CH2 |
| R5 = C(O)imidazole; R6 = 6-Me | R5 = H; R6 = 6-OMe |
| CH2 | CH2 |
| CH2CH2 | CH2CH2 |
| CHMe | CHMe |
| CHEt | CHEt |
| R5 = C(O)imidazole; R6 = 6-Me | R5 = H; R6 = 6-OMe |
| CHiPr | CHiPr |
| CH(Me)CH2 | CH(Me)CH2 |
| CHCH2OH | CHCH2OH |
| CH(CH2OH)CH2 | CH(CH2OH)CH2 |
| R5 = SN(Me)CO2Bu; R6 = 6-Me | R5 = Me; R6 = 6-OMe |
| CH2 | CH2 |
| CH2CH2 | CH2CH2 |
| CHMe | CHMe |
| CHEt | CHEt |
| CHiPr | CHiPr |
| CH(Me)CH2 | CH(Me)CH2 |
| CHCH2OH | CHCH2OH |
| CH(CH2OH)CH2 | CH(CH2OH)CH2 |
| R5 = C(O)imidazole; R6 = 6-OMe | R5 = SN(Me)CO2Bu; R6 = 6-Me |
| CH2 | CH2 |
| CH2CH2 | CH2CH2 |
| CHMe | CHMe |
| CHEt | CHEt |
| CHiPr | CHiPr |
| CH(Me)CH2 | CH(Me)CH2 |
| CHCH2OH | CHCH2OH |
| CH(CH2OH)CH2 | CH(CH2OH)CH2 |

TABLE 5

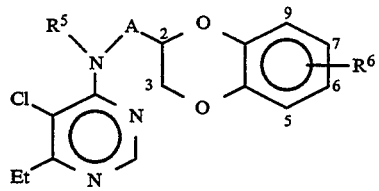

| A | R⁶ = H | A | R⁶ = 6-Cl |
|---|---|---|---|
| R⁶ = H | | R⁶ = 6-Cl | |
| CH₂ | H | CH₂ | H |
| CHMe | H | CHMe | H |
| CHEt | H | CHEt | H |
| CHiPr | H | CHiPr | H |
| CHCN | H | CHCN | H |
| CHCH₂OH | H | CHCH₂OH | H |
| CH₂ | Me | CH₂ | Me |
| CHMe | Me | CHMe | Me |
| CHEt | Me | CHEt | Me |
| CHiPr | Me | CHiPr | Me |
| CHCN | Me | CHCN | Me |
| CHCH₂OH | Me | CHCH₂OH | Me |
| CH₂ | C(O)imidazole | CH₂ | C(O)imidazole |
| CHMe | C(O)imidazole | CHMe | C(O)imidazole |
| CHEt | C(O)imidazole | CHEt | C(O)imidazole |
| CHiPr | C(O)imidazole | CHiPr | C(O)imidazole |
| CHCN | C(O)imidazole | CHCN | C(O)imidazole |
| CHCH₂OH | C(O)imidazole | CHCH₂OH | C(O)imidazole |
| CH₂ | SN(Me)CO₂Bu | CH₂ | SN(Me)CO₂Bu |
| CHMe | SN(Me)CO₂Bu | CHMe | SN(Me)CO₂Bu |
| CHEt | SN(Me)CO₂Bu | CHEt | SN(Me)CO₂Bu |
| CHiPr | SN(Me)CO₂Bu | CHiPr | SN(Me)CO₂Bu |
| R⁶ = H | | R⁶ = 6-Cl | |
| CHCN | SN(Me)CO₂Bu | CHCN | SN(Me)CO₂Bu |
| CHCH₂OH | SN(Me)CO₂Bu | CHCH₂OH | SN(Me)CO₂Bu |
| R⁶ = 7-Cl | | R⁶ = 6-F | |
| CH₂ | H | CH₂ | H |
| CHMe | H | CHMe | H |
| CHEt | H | CHEt | H |
| CHiPr | H | CHiPr | H |
| CHCN | H | CHCN | H |
| CHCH₂OH | H | CHCH₂OH | H |
| CH₂ | Me | CH₂ | Me |
| CHMe | Me | CHMe | Me |
| CHEt | Me | CHEt | Me |
| CHiPr | Me | CHiPr | Me |
| CHCN | Me | CHCN | Me |
| CHCH₂OH | Me | CHCH₂OH | Me |
| CH₂ | C(O)imidazole | CH₂ | C(O)imidazole |
| CHMe | C(O)imidazole | CHMe | C(O)imidazole |
| CHEt | C(O)imidazole | CHEt | C(O)imidazole |
| CHiPr | C(O)imidazole | CHiPr | C(O)imidazole |
| CHCN | C(O)imidazole | CHCN | C(O)imidazole |
| CHCH₂OH | C(O)imidazole | CHCH₂OH | C(O)imidazole |
| CH₂ | SN(Me)CO₂Bu | CH₂ | SN(Me)CO₂Bu |
| CHMe | SN(Me)CO₂Bu | CHMe | SN(Me)CO₂Bu |
| CHEt | SN(Me)CO₂Bu | CHEt | SN(Me)CO₂Bu |
| CHiPr | SN(Me)CO₂Bu | CHiPr | SN(Me)CO₂Bu |
| CHCN | SN(Me)CO₂Bu | CHCN | SN(Me)CO₂Bu |
| CHCH₂OH | SN(Me)CO₂Bu | CHCH₂OH | SN(Me)CO₂Bu |
| R⁶ = 6-Me | | R⁶ = 6-OMe | |
| CH₂ | H | CH₂ | H |
| CHMe | H | CHMe | H |
| CHEt | H | CHEt | H |
| CHiPr | H | CHiPr | H |
| CHCN | H | CHCN | H |
| CHCH₂OH | H | CHCH₂OH | H |
| CH₂ | Me | CH₂ | Me |
| CHMe | Me | CHMe | Me |
| CHEt | Me | CHEt | Me |
| CHiPr | Me | CHiPr | Me |
| CHCN | Me | CHCN | Me |
| CHCH₂OH | Me | CHCH₂OH | Me |
| CH₂ | C(O)imidazole | CH₂ | C(O)imidazole |
| CHMe | C(O)imidazole | CHMe | C(O)imidazole |
| CHEt | C(O)imidazole | CHEt | C(O)imidazole |
| CHiPr | C(O)imidazole | CHiPr | C(O)imidazole |
| CHCN | C(O)imidazole | CHCN | C(O)imidazole |

TABLE 5-continued

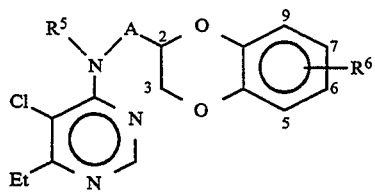

| A | R⁶ = H | A | R⁶ = 6-Cl |
|---|---|---|---|
| CHCH₂OH | C(O)imidazole | CHCH₂OH | C(O)imidazole |
| CH₂ | SN(Me)CO₂Bu | CH₂ | SN(Me)CO₂Bu |
| CHMe | SN(Me)CO₂Bu | CHMe | SN(Me)CO₂Bu |
| CHEt | SN(Me)CO₂Bu | CHEt | SN(Me)CO₂Bu |
| CHiPr | SN(Me)CO₂Bu | CHiPr | SN(Me)CO₂Bu |
| CHCN | SN(Me)CO₂Bu | CHCN | SN(Me)CO₂Bu |
| CHCH₂OH | SN(Me)CO₂Bu | CHCH₂OH | SN(Me)CO₂Bu |

TABLE 6

| A | R⁵ | A | R⁵ |
|---|---|---|---|
| R⁶ = H | | R⁶ = 6-Cl | |
| CH₂ | H | CH₂ | H |
| CHMe | H | CHMe | H |
| CHEt | H | CHEt | H |
| CHiPr | H | CHiPr | H |
| CHCN | H | CHCN | H |
| CHCH₂OH | H | CHCH₂OH | H |
| CH₂ | Me | CH₂ | Me |
| CHMe | Me | CHMe | Me |
| CHEt | Me | CHEt | Me |
| CHiPr | Me | CHiPr | Me |
| CHCN | Me | CHCN | Me |
| CHCH₂OH | Me | CHCH₂OH | Me |
| CH₂ | C(O)imidazole | CH₂ | C(O)imidazole |
| CHMe | C(O)imidazole | CHMe | C(O)imidazole |
| CHEt | C(O)imidazole | CHEt | C(O)imidazole |
| CHiPr | C(O)imidazole | CHiPr | C(O)imidazole |
| CHCN | C(O)imidazole | CHCN | C(O)imidazole |
| CHCH₂OH | C(O)imidazole | CHCH₂OH | C(O)imidazole |
| CH₂ | SN(Me)CO₂Bu | CH₂ | SN(Me)CO₂Bu |
| CHMe | SN(Me)CO₂Bu | CHMe | SN(Me)CO₂Bu |
| CHEt | SN(Me)CO₂Bu | CHEt | SN(Me)CO₂Bu |
| CHiPr | SN(Me)CO₂Bu | CHiPr | SN(Me)CO₂Bu |
| R⁶ = H | | R⁶ = 6-Cl | |
| CHCN | SN(Me)CO₂Bu | CHCN | SN(Me)CO₂Bu |
| CHCH₂OH | SN(Me)CO₂Bu | CHCH₂OH | SN(Me)CO₂Bu |
| R⁶ = 7-Cl | | R⁶ = 6-F | |
| CH₂ | H | CH₂ | H |
| CHMe | H | CHMe | H |
| CHEt | H | CHEt | H |
| CHiPr | H | CHiPr | H |
| CHCN | H | CHCN | H |
| CHCH₂OH | H | CHCH₂OH | H |
| CH₂ | Me | CH₂ | Me |
| CHMe | Me | CHMe | Me |
| CHEt | Me | CHEt | Me |
| CHiPr | Me | CHiPr | Me |
| CHCN | Me | CHCN | Me |
| CHCH₂OH | Me | CHCH₂OH | Me |
| CH₂ | C(O)imidazole | CH₂ | C(O)imidazole |
| CHMe | C(O)imidazole | CHMe | C(O)imidazole |
| CHEt | C(O)imidazole | CHEt | C(O)imidazole |
| CHiPr | C(O)imidazole | CHiPr | C(O)imidazole |
| CHCN | C(O)imidazole | CHCN | C(O)imidazole |
| CHCH₂OH | C(O)imidazole | CHCH₂OH | C(O)imidazole |
| CH₂ | SN(Me)CO₂Bu | CH₂ | SN(Me)CO₂Bu |
| CHMe | SN(Me)CO₂Bu | CHMe | SN(Me)CO₂Bu |

TABLE 6-continued

[Structure: R⁵-N(A-CH₂-tetrahydronaphthalene with R⁶)-pyridine with Cl and Et substituents]

| A | R⁵ | A | R⁵ |
|---|---|---|---|
| CHEt | SN(Me)CO₂Bu | CHEt | SN(Me)CO₂Bu |
| CHiPr | SN(Me)CO₂Bu | CHiPr | SN(Me)CO₂Bu |
| CHCN | SN(Me)CO₂Bu | CHCN | SN(Me)CO₂Bu |
| CHCH₂OH | SN(Me)CO₂Bu | CHCH₂OH | SN(Me)CO₂Bu |
| R⁶ = Me | | R⁶ = 6-OMe | |
| CH₂ | H | CH₂ | H |
| CHMe | H | CHMe | H |
| CHEt | H | CHEt | H |
| CHiPr | H | CHiPr | H |
| CHCN | H | CHCN | H |
| CHCH₂OH | H | CHCH₂OH | H |
| CH₂ | Me | CH₂ | Me |
| CHMe | Me | CHMe | Me |
| CHEt | Me | CHEt | Me |
| CHiPr | Me | CHiPr | Me |

TABLE 6-continued

| A | R⁵ | A | R⁵ |
|---|---|---|---|
| CHCN | Me | CHCN | Me |
| CHCH₂OH | Me | CHCH₂OH | Me |
| CH₂ | C(O)imidazole | CH₂ | C(O)imidazole |
| CHMe | C(O)imidazole | CHMe | C(O)imidazole |
| CHEt | C(O)imidazole | CHEt | C(O)imidazole |
| CHiPr | C(O)imidazole | CHiPr | C(O)imidazole |
| CHCN | C(O)imidazole | CHCN | C(O)imidazole |
| CHCH₂OH | C(O)imidazole | CHCH₂OH | C(O)imidazole |
| CH₂ | SN(Me)CO₂Bu | CH₂ | SN(Me)CO₂Bu |
| CHMe | SN(Me)CO₂Bu | CHMe | SN(Me)CO₂Bu |
| CHEt | SN(Me)CO₂Bu | CHEt | SN(Me)CO₂Bu |
| CHiPr | SN(Me)CO₂Bu | CHiPr | SN(Me)CO₂Bu |
| CHCN | SN(Me)CO₂Bu | CHCN | SN(Me)CO₂Bu |
| CHCH₂OH | SN(Me)CO₂Bu | CHCH₂OH | SN(Me)CO₂Bu |

TABLE 7

[Structure: R⁵-N(A-benzofuran with R⁶)-pyridine with Cl and Et substituents, G in position]

2-Q-7; G = O; R⁶ = H

| A | R⁵ | A | R⁵ |
|---|---|---|---|
| CH₂ | H | CH₂ | C(O)imidazole |
| CH₂CH₂ | H | CH₂CH₂ | C(O)imidazole |
| CHMe | H | CHHE | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

2-Q-7; G = O; R⁶ = 6-Cl

| A | R⁵ | A | R⁵ |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |

2-Q-7; G = O; R⁶ = 6-Cl

| A | R⁵ | A | R⁵ |
|---|---|---|---|
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHME | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |

TABLE 7-continued

| CHCH$_2$OH | Me | CHCH$_2$OH | SN(Me)CO$_2$Bu |
| CH(CH$_2$OH)CH$_2$ | Me | CH(CH$_2$OH)CH$_2$ | SN(Me)CO$_2$Bu |

2-Q-7; G = O; R$^6$ = 7-Cl

| A | R$^5$ | A | R$^5$ |
|---|---|---|---|
| CH$_2$ | H | CH$_2$ | C(O)imidazole |
| CH$_2$CH$_2$ | H | CH$_2$CH$_2$ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH$_2$ | H | CH(Me)CH$_2$ | C(O)imidazole |
| CHCN | H | CHCN | C(O)imidazole |
| CHCH$_2$OH | H | CHCH$_2$OH | C(O)imidazole |

2-Q-7; G = O; R$^6$ = 7-Cl

| A | R$^5$ | A | R$^5$ |
|---|---|---|---|
| CH(CH$_2$OH)CH$_2$ | H | CH(CH$_2$OH)CH$_2$ | C(O)imidazole |
| CH$_2$ | Me | CH$_2$ | SN(Me)CO$_2$Bu |
| CH$_2$CH$_2$ | Me | CH$_2$CH$_2$ | SN(Me)CO$_2$Bu |
| CHMe | Me | CHMe | SN(Me)CO$_2$Bu |
| CHEt | Me | CHEt | SN(Me)CO$_2$Bu |
| CHiPr | Me | CHiPr | SN(Me)CO$_2$Bu |
| CH(Me)CH$_2$ | Me | CH(Me)CH$_2$ | SN(Me)CO$_2$Bu |
| CHCN | Me | CHCN | SN(Me)CO$_2$Bu |
| CHCH$_2$OH | Me | CHCH$_2$OH | SN(Me)CO$_2$Bu |
| CH(CH$_2$OH)CH$_2$ | Me | CH(CH$_2$OH)CH$_2$ | SN(Me)CO$_2$Bu |

3-Q-7; G = O; R$^6$ = H

| A | R$^5$ | A | R$^5$ |
|---|---|---|---|
| CH$_2$ | H | CH$_2$ | C(O)imidazole |
| CH$_2$CH$_2$ | H | CH$_2$CH$_2$ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH$_2$ | H | CH(Me)CH$_2$ | C(O)imidazole |
| CHCN | H | CHCN | C(O)imidazole |
| CHCH$_2$OH | H | CHCH$_2$OH | C(O)imidazole |
| CH(CH$_2$OH)CH$_2$ | H | CH(CH$_2$OH)CH$_2$ | C(O)imidazole |
| CH$_2$ | Me | CH$_2$ | SN(Me)CO$_2$Bu |
| CH$_2$CH$_2$ | Me | CH$_2$CH$_2$ | SN(Me)CO$_2$Bu |
| CHMe | Me | CHMe | SN(Me)CO$_2$Bu |
| CHEt | Me | CHEt | SN(Me)CO$_2$Bu |
| CHiPr | Me | CHiPr | SN(Me)CO$_2$Bu |
| CH(Me)CH$_2$ | Me | CH(Me)CH$_2$ | SN(Me)CO$_2$Bu |
| CHCN | Me | CHCN | SN(Me)CO$_2$Bu |
| CHCH$_2$OH | Me | CHCH$_2$OH | SN(Me)CO$_2$Bu |
| CH(CH$_2$OH)CH$_2$ | Me | CH(CH$_2$OH)CH$_2$ | SN(Me)CO$_2$Bu |

3-Q-7; G = O; R$^6$ = 6-Cl

| A | R$^5$ | A | R$^5$ |
|---|---|---|---|
| CH$_2$ | H | CH$_2$ | C(O)imidazole |
| CH$_2$CH$_2$ | H | CH$_2$CH$_2$ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH$_2$ | H | CH(Me)CH$_2$ | C(O)imidazole |
| CHCN | H | CHCN | C(O)imidazole |
| CHCH$_2$OH | H | CHCH$_2$OH | C(O)imidazole |
| CH(CH$_2$OH)CH$_2$ | H | CH(CH$_2$OH)CH$_2$ | C(O)imidazole |
| CH$_2$ | Me | CH$_2$ | SN(Me)CO$_2$Bu |
| CH$_2$CH$_2$ | Me | CH$_2$CH$_2$ | SN(Me)CO$_2$Bu |
| CHMe | Me | CHMe | SN(Me)CO$_2$Bu |
| CHEt | Me | CHEt | SN(Me)CO$_2$Bu |
| CHiPr | Me | CHiPr | SN(Me)CO$_2$Bu |
| CH(Me)CH$_2$ | Me | CH(Me)CH$_2$ | SN(Me)CO$_2$Bu |
| CHCN | Me | CHCN | SN(Me)CO$_2$Bu |
| CHCH$_2$OH | Me | CHCH$_2$OH | SN(Me)CO$_2$Bu |
| CH(CH$_2$OH)CH$_2$ | Me | CH(CH$_2$OH)CH$_2$ | SN(Me)CO$_2$Bu |

3-Q-7; G = O; R$^6$ = 7-Cl

| A | R$^5$ | A | R$^5$ |
|---|---|---|---|
| CH$_2$ | H | CH$_2$ | C(O)imidazole |
| CH$_2$CH$_2$ | H | CH$_2$CH$_2$ | C(O)imidazole |
| CHMe | H | CHMe | C(O)imidazole |
| CHEt | H | CHEt | C(O)imidazole |

3-Q-7; G = O; R$^6$ = 7-Cl

| A | R$^5$ | A | R$^5$ |
|---|---|---|---|
| CHiPr | H | CHiPr | C(O)imidazole |
| CH(Me)CH$_2$ | H | CH(Me)CH$_2$ | C(O)imidazole |
| CHCN | H | CHCN | C(O)imidazole |
| CHCH$_2$OH | H | CHCH$_2$OH | C(O)imidazole |
| CH(CH$_2$OH)CH$_2$ | H | CH(CH$_2$OH)CH$_2$ | C(O)imidazole |
| CH$_2$ | Me | CH$_2$ | SN(Me)CO$_2$Bu |
| CH$_2$CH$_2$ | Me | CH$_2$CH$_2$ | SN(Me)CO$_2$Bu |

TABLE 7-continued

| A | R⁵ | A | R⁵ |
|---|---|---|---|
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

2-Q-7; G = S; R⁶ = H  —  2-Q-7; G = S; R⁶ = H

| A | R⁵ | A | R⁵ |
|---|---|---|---|
| CH₂ | H | CH₂ | SN(Me)CO₂Bu |
| CH₂CH₂ | H | CH₂CH₂ | SN(Me)CO₂Bu |
| CHMe | H | CHMe | SN(Me)CO₂Bu |
| CHEt | H | CHEt | SN(Me)CO₂Bu |
| CHiPr | H | CHiPr | SN(Me)CO₂Bu |
| CH(Me)CH₂ | H | CH(Me)CH₂ | SN(Me)CO₂Bu |
| CHCN | H | CHCN | SN(Me)CO₂Bu |
| CHCH₂OH | H | CHCH₂OH | SN(Me)CO₂Bu |
| CH(CH₂OH)CH₂ | H | CH(CH₂OH)CH₂ | SN(Me)CO₂Bu |
| CH₂ | Me | CH₂ | Et |
| CH₂CH₂ | Me | CH₂CH₂ | Et |

2-Q-7; G = S; R⁶ = H  —  2-Q-7; G = S; R⁶ = H

| A | R⁵ | A | R⁵ |
|---|---|---|---|
| CHMe | Me | CHMe | Et |
| CHEt | Me | CHEt | Et |
| CHiPr | Me | CHiPr | Et |
| CH(Me)CH₂ | Me | CH(Me)CH₂ | Et |
| CHCN | Me | CHCN | Et |
| CHCH₂OH | Me | CHCH₂OH | Et |
| CH(CH₂OH)CH₂ | Me | CH(CH₂OH)CH₂ | Et |
| CH₂ | C(O)imidazole | CH₂ | C(O)Me |
| CH₂CH₂ | C(O)imidazole | CH₂CH₂ | C(O)Me |
| CHMe | C(O)imidazole | CHMe | C(O)Me |
| CHEt | C(O)imidazole | CHEt | C(O)Me |
| CHiPr | C(O)imidazole | CHiPr | C(O)Me |
| CH(Me)CH₂ | C(O)imidazole | CH(Me)CH₂ | C(O)Me |
| CHCN | C(O)imidazole | CHCN | C(O)Me |
| CHCH₂OH | C(O)imidazole | CHCH₂OH | C(O)Me |
| CH(CH₂OH)CH₂ | C(O)imidazole | CH(CH₂OH)CH₂ | C(O)Me |

2-Q-7; G = S; R⁶ = H  —  2-Q-7; G = S; R⁶ = 6-Cl

| A | R⁵ | A | R⁵ |
|---|---|---|---|
| CH₂ | CH₂CN | CH₂ | H |
| CH₂CH₂ | CH₂CN | CH₂CH₂ | H |
| CHMe | CH₂CN | CHMe | H |
| CHEt | CH₂CN | CHEt | H |
| CHiPr | CH₂CN | CHiPr | H |
| CH(Me)CH₂ | CH₂CN | CH(Me)CH₂ | H |
| CHCN | CH₂CN | CHCN | H |
| CHCH₂OH | CH₂CN | CHCH₂OH | H |

2-Q-7; G = S; R⁶ = H  —  2-Q-7; G = S; R⁶ = 6-Cl

| A | R⁵ | A | R⁵ |
|---|---|---|---|
| CH(CH₂OH)CH₂ | CH₂CN | CH(CH₂OH)CH₂ | H |
| CH₂ | CH₂OEt | CH₂ | Me |
| CH₂CH₂ | CH₂OEt | CH₂CH₂ | Me |
| CHMe | CH₂OEt | CHMe | Me |
| CHEt | CH₂OEt | CHEt | Me |
| CHiPr | CH₂OEt | CHiPr | Me |
| CH(Me)CH₂ | CH₂OEt | CH(Me)CH₂ | Me |
| CHCN | CH₂OEt | CHCN | Me |
| CHCH₂OH | CH₂OEt | CHCH₂OH | Me |
| CH(CH₂OH)CH₂ | CH₂OEt | CH(CH₂OH)CH₂ | Me |
| CH₂ | SNBu₂ | CH₂ | C(O)imidazole |
| CH₂CH₂ | SNBu₂ | CH₂CH₂ | C(O)imidazole |
| CHMe | SNBu₂ | CHMe | C(O)imidazole |
| CHEt | SNBu₂ | CHEt | C(O)imidazole |
| CHiPr | SNBu₂ | CHiPr | C(O)imidazole |
| CH(Me)CH₂ | SNBu₂ | CH(Me)CH₂ | C(O)imidazole |
| CHCN | SNBu₂ | CHCN | C(O)imidazole |
| CHCH₂OH | SNBu₂ | CHCH₂OH | C(O)imidazole |
| CH(CH₂OH)CH₂ | SNBu₂ | CH(CH₂OH)CH₂ | C(O)imidazole |

2-Q-7; G = S; R⁶ = 6-Cl  —  2-Q-7; G = S; R⁶ = 7-Cl

| A | R⁵ | A | R⁵ |
|---|---|---|---|
| CH₂ | SN(Me)CO₂Bu | CHCH₂OH | Me |
| CH₂CH₂ | SN(Me)CO₂Bu | CH(CH₂OH)CH₂ | Me |
| CHMe | SN(Me)CO₂Bu | CH₂ | C(O)imidazole |
| CHEt | SN(Me)CO₂Bu | CH₂CH₂ | C(O)imidazole |
| CHiPr | SN(Me)CO₂Bu | CHMe | C(O)imidazole |
| CH(Me)CH₂ | SN(Me)CO₂Bu | CHEt | C(O)imidazole |
| CHCN | SN(Me)CO₂Bu | CHiPr | C(O)imidazole |
| CHCH₂OH | SN(Me)CO₂Bu | CH(Me)CH₂ | C(O)imidazole |
| CH(CH₂OH)CH₂ | SN(Me)CO₂Bu | CHCN | C(O)imidazole |

TABLE 7-continued

| 2-Q-7; G = S; R⁶ = 7-Cl | |
|---|---|
| A | R⁵ |
| CH₂ | H |
| CH₂CH₂ | H |
| CHMe | H |
| CHEt | H |
| CHiPr | H |
| CH(Me)CH₂ | H |
| CHCN | H |
| CHCH₂OH | H |
| CH(CH₂OH)CH₂ | H |
| CH₂ | Me |
| CH₂CH₂ | Me |
| CHMe | Me |
| CHEt | Me |
| CHiPr | Me |
| CH(Me)CH₂ | Me |
| CHCN | Me |

| 3-Q-7; G = S; R⁶ = H | |
|---|---|
| A | R⁵ |
| CH(Me)CH₂ | H |
| CHCN | H |
| CHCH₂OH | H |
| CH(CH₂OH)CH₂ | H |
| CH₂ | Me |
| CH₂CH₂ | Me |
| CHMe | Me |

| 3-Q-7; G = S; R⁶ = H | |
|---|---|
| A | R⁵ |
| CHEt | Me |
| CHiPr | Me |
| CH(Me)CH₂ | Me |
| CHCN | Me |
| CHCH₂OH | Me |
| CH(CH₂OH)CH₂ | Me |
| CH₂ | C(O)imidazole |
| CH₂CH₂ | C(O)imidazole |
| CHMe | C(O)imidazole |
| CHEt | C(O)imidazole |
| CHiPr | C(O)imidazole |
| CH(Me)CH₂ | C(O)imidazole |
| CHCN | C(O)imidazole |
| CHCH₂OH | C(O)imidazole |
| CH(CH₂OH)CH₂ | C(O)imidazole |
| CH₂ | SN(Me)CO₂Bu |
| CH₂CH₂ | SN(Me)CO₂Bu |
| CHMe | SN(Me)CO₂Bu |
| CHEt | SN(Me)CO₂Bu |
| CHiPr | SN(Me)CO₂Bu |
| CH(Me)CH₂ | SN(Me)CO₂Bu |
| CHCN | SN(Me)CO₂Bu |

| 3-Q-7; G = S; R⁶ = 6-Cl | |
|---|---|
| A | R⁵ |
| CH(Me)CH₂ | C(O)imidazole |
| CHCN | C(O)imidazole |
| CHCH₂OH | C(O)imidazole |
| CH(CH₂OH)CH₂ | C(O)imidazole |
| CH₂ | SN(Me)CO₂Bu |
| CH₂CH₂ | SN(Me)CO₂Bu |
| CHMe | SN(Me)CO₂Bu |
| CHEt | SN(Me)CO₂Bu |
| CHiPr | SN(Me)CO₂Bu |
| CH(Me)CH₂ | SN(Me)CO₂Bu |
| CHCN | SN(Me)CO₂Bu |
| CHCH₂OH | SN(Me)CO₂Bu |
| CH(CH₂OH)CH₂ | SN(Me)CO₂Bu |

| 3-Q-7; G = S; R⁶ = 7-Cl | |
|---|---|
| A | R⁵ |
| CH₂ | H |
| CH₂CH₂ | H |
| CHMe | H |
| CHEt | H |
| CHiPr | H |
| CH(Me)CH₂ | H |
| CHCN | H |
| CHCH₂OH | H |

| 2-Q-7; G = S; R⁶ = 7-Cl | |
|---|---|
| A | R⁵ |
| CHCH₂OH | C(O)imidazole |
| CH(CH₂OH)CH₂ | C(O)imidazole |
| CH₂ | SN(Me)CO₂Bu |
| CH₂CH₂ | SN(Me)CO₂Bu |
| CHMe | SN(Me)CO₂Bu |
| CHEt | SN(Me)CO₂Bu |
| CHiPr | SN(Me)CO₂Bu |
| CH(Me)CH₂ | SN(Me)CO₂Bu |
| CHCN | SN(Me)CO₂Bu |
| CHCH₂OH | SN(Me)CO₂Bu |
| CH(CH₂OH)CH₂ | SN(Me)CO₂Bu |

| 3-Q-7; G = S; R⁶ = H | |
|---|---|
| A | R⁵ |
| CH₂ | H |
| CH₂CH₂ | H |
| CHMe | H |
| CHEt | H |
| CHiPr | H |
| CHCH₂OH | SN(Me)CO₂Bu |
| CH(CH₂OH)CH₂ | SN(Me)CO₂Bu |

| 3-Q-7; G = S; R⁶ = 6-Cl | |
|---|---|
| A | R⁵ |
| CH₂ | H |
| CH₂CH₂ | H |
| CHMe | H |
| CHEt | H |
| CHiPr | H |
| CH(Me)CH₂ | H |
| CHCN | H |
| CHCH₂OH | H |
| CH(CH₂OH)CH₂ | H |
| CH₂ | Me |
| CH₂CH₂ | Me |
| CHMe | Me |
| CHEt | Me |
| CHiPr | Me |
| CH(Me)CH₂ | Me |
| CHCN | Me |
| CHCH₂OH | Me |
| CH(CH₂OH)CH₂ | Me |
| CH₂ | C(O)imidazole |
| CH₂CH₂ | C(O)imidazole |
| CHMe | C(O)imidazole |
| CHEt | C(O)imidazole |
| CHiPr | C(O)imidazole |

| 3-Q-7; G = S; R⁶ = 7-Cl | |
|---|---|
| A | R⁵ |
| CHEt | Me |
| CHiPr | Me |
| CH(Me)CH₂ | Me |
| CHCN | Me |
| CHCH₂OH | Me |
| CH(CH₂OH)CH₂ | Me |
| CH₂ | C(O)imidazole |
| CH₂CH₂ | C(O)imidazole |
| CHMe | C(O)imidazole |
| CHEt | C(O)imidazole |
| CHiPr | C(O)imidazole |
| CH(Me)CH₂ | C(O)imidazole |
| CHCN | C(O)imidazole |
| CHCH₂OH | C(O)imidazole |
| CH(CH₂OH)CH₂ | C(O)imidazole |
| CH₂ | SN(Me)CO₂Bu |
| CH₂CH₂ | SN(Me)CO₂Bu |
| CHMe | SN(Me)CO₂Bu |
| CHEt | SN(Me)CO₂Bu |
| CHiPr | SN(Me)CO₂Bu |
| CH(Me)CH₂ | SN(Me)CO₂Bu |
| CHCN | SN(Me)CO₂Bu |
| CHCH₂OH | SN(Me)CO₂Bu |
| CH(CH₂OH)CH₂ | SN(Me)CO₂Bu |

TABLE 7-continued

| | |
|---|---|
| CH(CH₂OH)CH₂ | H |
| CH₂ | Me |
| CH₂CH₂ | Me |
| CHMe | Me |

TABLE 8

[Structure: pyridine ring with Cl and Et substituents, N-R⁵ group, A linker to benzene ring (positions 5,6,7,8) fused with G-containing ring bearing R⁶ and R⁷]

6-Q-8; G = O; R⁶ = H; R⁷ = H

| A | R⁵ | A | R⁵ |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

6-Q-8; G = O; R⁶ = H; R⁷ = Cl

| A | R⁵ | A | R⁵ |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

6-Q-8; G = O; R⁶ = Cl; R⁷ = H

| A | R⁵ | A | R⁵ |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SM(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

7-Q-8; G = O; R⁶ = H; R⁷ = H

| A | R⁵ | A | R⁵ |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

7-Q-8; G = O; R⁶ = H; R⁷ = Cl

| A | R⁵ | A | R⁵ |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |
| CHEt | Me | CHEt | SN(Me)CO₂Bu |
| CHiPr | Me | CHiPr | SN(Me)CO₂Bu |
| CH(Me)CH₂ | Me | CH(Me)CH₂ | SN(Me)CO₂Bu |
| CHCN | Me | CHCN | SN(Me)CO₂Bu |
| CHCH₂OH | Me | CHCH₂OH | SN(Me)CO₂Bu |
| CH(CH₂OH)CH₂ | Me | CH(CH₂OH)CH₂ | SN(Me)CO₂Bu |

7-Q-8; G = O; R⁶ = Cl; R⁷ = H

| A | R⁵ | A | R⁵ |
|---|---|---|---|
| CH₂ | H | CH₂ | C(O)imidazole |
| CH₂CH₂ | H | CH₂CH₂ | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH₂ | H | CH(Me)CH₂ | C(O)imidazole |
| CHCN | H | CHCN | C(O)imidazole |
| CHCH₂OH | H | CHCH₂OH | C(O)imidazole |
| CH(CH₂OH)CH₂ | H | CH(CH₂OH)CH₂ | C(O)imidazole |
| CH₂ | Me | CH₂ | SN(Me)CO₂Bu |
| CH₂CH₂ | Me | CH₂CH₂ | SN(Me)CO₂Bu |
| CHMe | Me | CHMe | SN(Me)CO₂Bu |

TABLE 8-continued

Structure: R5-N(A-[phenyl(5,7,8 positions, G)-furan with R6, R7])-pyridine with Cl, Et substituents

| A | R5 | A | R5 |
|---|---|---|---|
| CHEt | Me | CHEt | SN(Me)CO2Bu |
| CHiPr | Me | CHiPr | SN(Me)CO2Bu |
| CH(Me)CH2 | Me | CH(Me)CH2 | SN(Me)CO2Bu |
| CHCN | Me | CHCN | SN(Me)CO2Bu |
| CHCH2OH | Me | CHCH2OH | SN(Me)CO2Bu |
| CH(CH2OH)CH2 | Me | CH(CH2OH)CH2 | SN(Me)CO2Bu |

6-Q-8; G = S; R6 = H; R7 = H | 6-Q-8; G = S; R6 = H; R7 = H

| A | R5 | A | R5 |
|---|---|---|---|
| CH2 | H | CH2 | C(O)imidazole |
| CH2CH2 | H | CH2CH2 | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH2 | H | CH(Me)CH2 | C(O)imidazole |
| CHCN | H | CHCN | C(O)imidazole |
| CHCH2OH | H | CHCH2OH | C(O)imidazole |
| CH(CH2OH)CH2 | H | CH(CH2OH)CH2 | C(O)imidazole |
| CH2 | Me | CH2 | SN(Me)CO2Bu |
| CH2CH2 | Me | CH2CH2 | SN(Me)CO2Bu |
| CHMe | Me | CHMe | SN(Me)CO2Bu |
| CHEt | Me | CHEt | SN(Me)CO2Bu |
| CHiPr | Me | CHiPr | SN(Me)CO2Bu |
| CH(Me)CH2 | Me | CH(Me)CH2 | SN(Me)CO2Bu |
| CHCN | Me | CHCN | SN(Me)CO2Bu |
| CHCH2OH | Me | CHCH2OH | SN(Me)CO2Bu |
| CH(CH2OH)CH2 | Me | CH(CH2OH)CH2 | SN(Me)CO2Bu |

6-Q-8; G = S; R6 = H; R7 = Cl | 6-Q-8; G = S; R6 = H; R7 = Cl

| A | R5 | A | R5 |
|---|---|---|---|
| CH2 | H | CH2 | C(O)imidazole |
| CH2CH2 | H | CH2CH2 | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH2 | H | CH(Me)CH2 | C(O)imidazole |
| CHCN | H | CHCN | C(O)imidazole |

6-Q-8; G = S; R6 = H; R7 = Cl | 6-Q-8; G = S; R6 = H; R7 = Cl

| A | R5 | A | R5 |
|---|---|---|---|
| CHCH2OH | H | CHCH2OH | C(O)imidazole |
| CH(CH2OH)CH2 | H | CH(CH2OH)CH2 | C(O)imidazole |
| CH2 | Me | CH2 | SN(Me)CO2Bu |
| CH2CH2 | Me | CH2CH2 | SN(Me)CO2Bu |
| CHMe | Me | CHMe | SN(Me)CO2Bu |
| CHEt | Me | CHEt | SN(Me)CO2Bu |
| CHiPr | Me | CHiPr | SN(Me)CO2Bu |
| CH(Me)CH2 | Me | CH(Me)CH2 | SN(Me)CO2Bu |
| CHCN | Me | CHCN | SN(Me)CO2Bu |
| CHCH2OH | Me | CHCH2OH | SN(Me)CO2Bu |
| CH(CH2OH)CH2 | Me | CH(CH2OH)CH2 | SN(Me)CO2Bu |

6-Q-8; G = S; R6 = Cl; R7 = H | 6-Q-8; G = S; R6 = Cl; R7 = H

| A | R5 | A | R5 |
|---|---|---|---|
| CH2 | H | CH2 | C(O)imidazole |
| CH2CH2 | H | CH2CH2 | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH2 | H | CH(Me)CH2 | C(O)imidazole |
| CHCN | H | CHCN | C(O)imidazole |
| CHCH2OH | H | CHCH2OH | C(O)imidazole |
| CH(CH2OH)CH2 | H | CH(CH2OH)CH2 | C(O)imidazole |
| CH2 | Me | CH2 | SN(Me)CO2Bu |
| CH2CH2 | Me | CH2CH2 | SN(Me)CO2Bu |
| CHMe | Me | CHMe | SN(Me)CO2Bu |

6-Q-8; G = S; R6 = Cl; R7 = H | 6-Q-8; G = S; R6 = Cl; R7 = H

| A | R5 | A | R5 |
|---|---|---|---|
| CHEt | Me | CHEt | SN(Me)CO2Bu |
| CHiPr | Me | CHiPr | SN(Me)CO2Bu |
| CH(Me)CH2 | Me | CH(Me)CH2 | SN(Me)CO2Bu |
| CHCN | Me | CHCN | SN(Me)CO2Bu |
| CHCH2OH | Me | CHCH2OH | SN(Me)CO2Bu |
| CH(CH2OH)CH2 | Me | CH(CH2OH)CH2 | SN(Me)CO2Bu |

7-Q-8; G = S; R6 = H; R7 = H | 7-Q-8; G = S; R6 = H; R7 = H

| A | R5 | A | R5 |
|---|---|---|---|
| CH2 | H | CH2 | C(O)imidazole |
| CH2CH2 | H | CH2CH2 | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH2 | H | CH(Me)CH2 | C(O)imidazole |
| CHCN | H | CHCN | C(O)imidazole |
| CHCH2OH | H | CHCH2OH | C(O)imidazole |
| CH(CH2OH)CH2 | H | CH(CH2OH)CH2 | C(O)imidazole |
| CH2 | Me | CH2 | SN(Me)CO2Bu |
| CH2CH2 | Me | CH2CH2 | SN(Me)CO2Bu |
| CHMe | Me | CHMe | SN(Me)CO2Bu |
| CHEt | Me | CHEt | SN(Me)CO2Bu |
| CHiPr | Me | CHiPr | SN(Me)CO2Bu |
| CH(Me)CH2 | Me | CH(Me)CH2 | SN(Me)CO2Bu |
| CHCN | Me | CHCN | SN(Me)CO2Bu |
| CHCH2OH | Me | CHCH2OH | SN(Me)CO2Bu |
| CH(CH2OH)CH2 | Me | CH(CH2OH)CH2 | SN(Me)CO2Bu |

7-Q-8; G = S; R6 = H; R7 = Cl | 7-Q-8; G = S; R6 = H; R7 = Cl

| A | R5 | A | R5 |
|---|---|---|---|
| CH2 | H | CH2 | C(O)imidazole |
| CH2CH2 | H | CH2CH2 | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH2 | H | CH(Me)CH2 | C(O)imidazole |
| CHCN | H | CHCN | C(O)imidazole |
| CHCH2OH | H | CHCH2OH | C(O)imidazole |
| CH(CH2OH)CH2 | H | CH(CH2OH)CH2 | C(O)imidazole |
| CH2 | Me | CH2 | SN(Me)CO2Bu |
| CH2CH2 | Me | CH2CH2 | SN(Me)CO2Bu |
| CHMe | Me | CHMe | SN(Me)CO2Bu |
| CHEt | Me | CHEt | SN(Me)CO2Bu |
| CHiPr | Me | CHiPr | SN(Me)CO2Bu |
| CH(Me)CH2 | Me | CH(Me)CH2 | SN(Me)CO2Bu |
| CHCN | Me | CHCN | SN(Me)CO2Bu |
| CHCH2OH | Me | CHCH2OH | SN(Me)CO2Bu |
| CH(CH2OH)CH2 | Me | CH(CH2OH)CH2 | SN(Me)CO2Bu |

7-Q-8; G = S; R6 = Cl; R7 = H | 7-Q-8; G = S; R6 = Cl; R7 = H

| A | R5 | A | R5 |
|---|---|---|---|
| CH2 | H | CH2 | C(O)imidazole |
| CH2CH2 | H | CH2CH2 | C(O)imidazole |
| CHMe | H | CHMe | C(O)imidazole |
| CHEt | H | CHEt | C(O)imidazole |
| CHiPr | H | CHiPr | C(O)imidazole |
| CH(Me)CH2 | H | CH(Me)CH2 | C(O)imidazole |
| CHCN | H | CHCN | C(O)imidazole |
| CHCH2OH | H | CHCH2OH | C(O)imidazole |
| CH(CH2OH)CH2 | H | CH(CH2OH)CH2 | C(O)imidazole |
| CH2 | Me | CH2 | SN(Me)CO2Bu |
| CH2CH2 | Me | CH2CH2 | SN(Me)CO2Bu |
| CHMe | Me | CHMe | SN(Me)CO2Bu |
| CHEt | Me | CHEt | SN(Me)CO2Bu |
| CHiPr | Me | CHiPr | SN(Me)CO2Bu |
| CH(Me)CH2 | Me | CH(Me)CH2 | SN(Me)CO2Bu |
| CHCN | Me | CHCN | SN(Me)CO2Bu |
| CHCH2OH | Me | CHCH2OH | SN(Me)CO2Bu |
| CH(CH2OH)CH2 | Me | CH(CH2OH)CH2 | SN(Me)CO2Bu |

TABLE 9

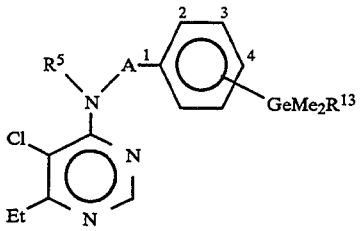

| A | A |
|---|---|
| 4-GeMe₃; R⁵ = H; R¹³ = Me | 3-GeMe₃; R⁵ = H; R¹³ = Me |
| CH₂ | CH₂ |
| CH₂CH₂ | CH₂CH₂ |
| CH₂CH₂CH₂ | CH₂CH₂CH₂ |
| CHMe | CHMe |
| CHEt | CHEt |
| CHiPr | CHiPr |
| CH₂CHMe | CH₂CHMe |
| CH(Me)CH₂ | CH(Me)CH₂ |
| CH(Me)CH₂CH₂ | CH(Me)CH₂CH₂ |
| CH₂CH(Me)CH₂ | CH₂CH(Me)CH₂ |
| CMe₂ | CMe₂ |
| CHCO₂Me | CHCO₂Me |
| CHC(O)Me | CHC(O)Me |
| CHCN | CHCN |
| CHCH₂OH | CHCH₂OH |
| CH(CH₂OH)CH₂ | CH(CH₂OH)CH₂ |
| 4-GeMe₃; R⁵ = Me; R¹³ = Me | 3-GeMe₃; R⁵ = Me; R¹³ = Me |
| CH₂ | CH₂ |
| CH₂CH₂ | CH₂CH₂ |
| CH₂CH₂CH₂ | CH₂CH₂CH₂ |
| 4-GeMe₃; R⁵ = Me; R¹³ = Me | 3-GeMe₃; R⁵ = Me; R¹³ = Me |
| CHMe | CHMe |
| CHEt | CHEt |
| CHiPr | CHiPr |
| CH₂CHMe | CH₂CHMe |
| CH(Me)CH₂ | CH(Me)CH₂ |
| CH(Me)CH₂CH₂ | CH(Me)CH₂CH₂ |
| CH₂CH(Me)CH₂ | CH₂CH(Me)CH₂ |
| CMe₂ | CMe₂ |
| CHCO₂Me | CHCO₂Me |
| CHC(O)Me | CHC(O)Me |
| CHCN | CHCN |
| CHCH₂OH | CHCH₂OH |
| CH(CH₂OH)CH₂ | CH(CH₂OH)CH₂ |
| 4-GeMe₃; R⁵ = Et; R¹³ = Me | 3-GeMe₃; R⁵ = Et; R¹³ = Me |
| CH₂ | CH₂ |
| CH₂CH₂ | CH₂CH₂ |
| CH₂CH₂CH₂ | CH₂CH₂CH₂ |
| CHMe | CHMe |
| CHEt | CHEt |
| CHiPr | CHiPr |
| CH₂CHMe | CH₂CHMe |
| CH(Me)CH₂ | CH(Me)CH₂ |
| CH(Me)CH₂CH₂ | CH(Me)CH₂CH₂ |
| CH₂CH(Me)CH₂ | CH₂CH(Me)CH₂ |
| 4-GeMe₃; R⁵ = Et; R¹³ = Me | 3-GeMe₃; R⁵ = Et; R¹³ = Me |
| CMe₂ | CMe₂ |
| CHCO₂Me | CHCO₂Me |
| CHC(O)Me | CHC(O)Me |
| CHCN | CHCN |
| CHCH₂OH | CHCH₂OH |
| CH(CH₂OH)CH₂ | CH(CH₂OH)CH₂ |
| 4-GeMe₃; R⁵ = C(O)imidazole; R¹³ = Me | 3-GeMe₃; R⁵ = C(O)imidazole; R¹³ = Me |
| CH₂ | CH₂ |
| CH₂CH₂ | CH₂CH₂ |
| CH₂CH₂CH₂ | CH₂CH₂CH₂ |
| CHMe | CHMe |
| CHEt | CHEt |
| CHiPr | CHiPr |
| CH₂CHMe | CH₂CHMe |
| CH(Me)CH₂ | CH(Me)CH₂ |
| CH(Me)CH₂CH₂ | CH(Me)CH₂CH₂ |
| CH₂CH(Me)CH₂ | CH₂CH(Me)CH₂ |
| CMe₂ | CMe₂ |
| CHCO₂Me | CHCO₂Me |

TABLE 9-continued

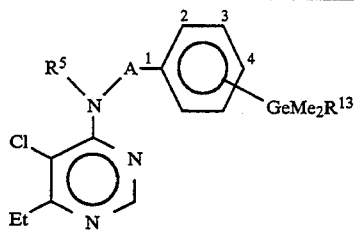

| A | A |
|---|---|
| CHC(O)Me | CHC(O)Me |
| CHCN | CHCN |
| CHCH₂OH | CHCH₂OH |
| CH(CH₂OH)CH₂ | CH(CH₂OH)CH₂ |
| 4-GeMe₃; R⁵ = C(O)Me; R¹ = Me | 3-GeMe₃; R⁵ = C(O)Me; R¹ = Me |
| CH₂ | CH₂ |
| CH₂CH₂ | CH₂CH₂ |
| CH₂CH₂CH₂ | CH₂CH₂CH₂ |
| CHMe | CHMe |
| CHEt | CHEt |
| CHiPr | CHiPr |
| CH₂CHMe | CH₂CHMe |
| CH(Me)CH₂ | CH(Me)CH₂ |
| CH(Me)CH₂CH₂ | CH(Me)CH₂CH₂ |
| CH₂CH(Me)CH₂ | CH₂CH(Me)CH₂ |
| CMe₂ | CMe₂ |
| CHCO₂Me | CHCO₂Me |
| CHC(O)Me | CHC(O)Me |
| CHCN | CHCN |
| CHCH₂OH | CHCH₂OH |
| CH(CH₂OH)CH₂ | CH(CH₂OH)CH₂ |
| 4-GeMe₃; R⁵ = CH₂CN; R¹³ = Me | 3-GeMe₃; R⁵ = CH₂CN; R¹ = Me |
| CH₂ | CH₂ |
| CH₂CH₂ | CH₂CH₂ |
| CH₂CH₂CH₂ | CH₂CH₂CH₂ |
| CHMe | CHMe |
| CHEt | CHEt |
| CHiPr | CHiPr |
| CH₂CHMe | CH₂CHMe |
| CH(Me)CH₂ | CH(Me)CH₂ |
| 4-GeMe₃; R⁵ = CH₂CN; R¹³ = Me | 3-GeMe₃; R⁵ = CH₂CN; R¹³ = Me |
| CH(Me)CH₂CH₂ | CH(Me)CH₂CH₂ |
| CH₂CH(Me)CH₂ | CH₂CH(Me)CH₂ |
| CMe₂ | CMe₂ |
| CHCO₂Me | CHCO₂Me |
| CHC(O)Me | CHC(O)Me |
| CHCN | CHCN |
| CHCH₂OH | CHCH₂OH |
| CH(CH₂OH)CH₂ | CH(CH₂OH)CH₂ |
| 4-GeMe₃; R⁵ = CH₂OEt; R¹³ = Me | 3-GeMe₃; R⁵ = CH₂OEt; R¹³ = Me |
| CH₂ | CH₂ |
| CH₂CH₂ | CH₂CH₂ |
| CH₂CH₂CH₂ | CH₂CH₂CH₂ |
| CHMe | CHMe |
| CHEt | CHEt |
| CHiPr | CHiPr |
| CH₂CHMe | CH₂CHMe |
| CH(Me)CH₂ | CH(Me)CH₂ |
| CH(Me)CH₂CH₂ | CH(Me)CH₂CH₂ |
| CH₂CH(Me)CH₂ | CH₂CH(Me)CH₂ |
| CMe₂ | CMe₂ |
| CHCO₂Me | CHCO₂Me |
| CHC(O)Me | CHC(O)Me |
| CHCN | CHCN |
| CHCH₂OH | CHCH₂OH |
| CH(CH₂OH)CH₂ | CH(CH₂OH)CH₂ |
| 4-GeMe₃; R⁵ = SNBu₂; R¹³ = Me | 3-GeMe₃; R⁵ = SNBu₂; R¹³ = Me |
| CH₂ | CH₂ |
| CH₂CH₂ | CH₂CH₂ |
| CH₂CH₂CH₂ | CH₂CH₂CH₂ |
| CHMe | CHMe |
| CHEt | CHEt |
| CHiPr | CHiPr |

TABLE 9-continued

[Structure: R⁵-N(A¹-phenyl-4-GeMe₂R¹³) attached to pyridine with Cl and Et substituents]

| A | A |
|---|---|
| CH₂CHMe | CH₂CHMe |
| CH(Me)CH₂ | CH(Me)CH₂ |
| CH(Me)CH₂CH₂ | CH(Me)CH₂CH₂ |
| CH₂CH(Me)CH₂ | CH₂CH(Me)CH₂ |
| CMe₂ | CMe₂ |
| CHCO₂Me | CHCO₂Me |
| CHC(O)Me | CHC(O)Me |
| CHCN | CHCN |
| CHCH₂OH | CHCH₂OH |
| CH(CH₂OH)CH₂ | CH(CH₂OH)CH₂ |
| 4-GeMe₃; | 3-GeMe₃; |
| R⁵ = SN(Me)CO₂Bu; | R⁵ = SN(Me)CO₂Bu; |
| R¹³ = Me | R¹³ = Me |
| CH₂ | CH₂ |
| CH₂CH₂ | CH₂CH₂ |
| CH₂CH₂CH₂ | CH₂CH₂CH₂ |
| CHMe | CHMe |
| CHEt | CHEt |
| CHiPr | CHiPr |
| CH₂CHMe | CH₂CHMe |
| CH(Me)CH₂ | CH(Me)CH₂ |
| 4-GeMe₃; | 3-GeMe₃; |
| R⁵ = SN(Me)CO₂Bu; | R⁵ = SN(Me)CO₂Bu; |
| R¹³ = Me | R¹³ = Me |
| CH(Me)CH₂CH₂ | CH(Me)CH₂CH₂ |
| CH₂CH(Me)CH₂ | CH₂CH(Me)CH₂ |
| CMe₂ | CMe₂ |
| CHCO₂Me | CHCO₂Me |
| CHC(O)Me | CHC(O)Me |
| CHCN | CHCN |
| CHCH₂OH | CHCH₂OH |
| CH(CH₂OH)CH₂ | CH(CH₂OH)CH₂ |
| 4-GeMe₂R¹³; | 4-GeMe₂R¹³; |
| R⁵ = H; R¹³ = tBu | R⁵ = C(O)imidazole; R¹³ = tBu |
| CH₂ | CH₂ |
| CH₂CH₂ | CH₂CH₂ |
| CHMe | CHMe |
| CHEt | CHEt |
| CHiPr | CHiPr |
| CH(Me)CH₂ | CH(Me)CH₂ |
| CHCH₂OH | CHCH₂OH |
| CH(CH₂OH)CH₂ | CH(CH₂OH)CH₂ |
| | 4-GeMe₂R¹³; |
| 4-GeMe₂R¹³; | R⁵ = SN(Me)CO₂Bu; |
| R⁵ = Me; R¹³ = tBu | R¹³ = tBu |
| CH₂ | CH₂ |
| CH₂CH₂ | CH₂CH₂ |
| CHMe | CHMe |
| CHEt | CHEt |
| | 4-GeMe₂R¹³; |
| 4-GeMe₂R¹³; | R⁵ = SN(Me)CO₂Bu; |
| R⁵ = Me; R¹³ = tBu | R¹³ = tBu |
| CHiPr | CHiPr |
| CH(Me)CH₂ | CH(Me)CH₂ |
| CHCH₂OH | CHCH₂OH |
| CH(CH₂OH)CH₂ | CH(CH₂OH)CH₂ |
| | 4-GeMe₂R¹³; |
| | R⁵ = C(O)imidazole; |
| 4-GeMe₂R¹³; R⁵ = H; R¹³ = Ph | R¹³ = Ph |
| CH₂ | CH₂ |
| CH₂CH₂ | CH₂CH₂ |
| CHMe | CHMe |
| CHEt | CHEt |
| CHiPr | CHiPr |
| CH(Me)CH₂ | CH(Me)CH₂ |
| CHCH₂OH | CHCH₂OH |
| CH(CH₂OH)CH₂ | CH(CH₂OH)CH₂ |
| 4-GeMe₂R¹³; | 4-GeMe₂R¹³; |
| R⁵ = Me; R¹³ = Ph | R⁵ = SN(Me)CO₂Bu; R¹³ = Ph |
| CH₂ | CH₂ |
| CH₂CH₂ | CH₂CH₂ |
| CHMe | CHMe |
| CHEt | CHEt |
| CHiPr | CHiPr |
| 4-GeMe₂R¹³; | 4-GeMe₂R¹³; |
| R⁵ = Me; R¹³ = Ph | R⁵ = SN(Me)CO₂Bu; R¹³ = Ph |
| CH(Me)CH₂ | CH(Me)CH₂ |
| CHCH₂OH | CHCH₂OH |
| CH(CH₂OH)CH₂ | CH(CH₂OH)CH₂ |
| | 4-GeMe₂R¹³; |
| 4-GeMe₂R¹³; | R⁵ = C(O)imidazole; |
| R⁵ = H; R¹³ = CH₂OEt | R¹³ = CH₂OEt |
| CH₂ | CH₂ |
| CH₂CH₂ | CH₂CH₂ |
| CHMe | CHMe |
| CHEt | CHEt |
| CHiPr | CHiPr |
| CH(Me)CH₂ | CH(Me)CH₂ |
| CHCH₂OH | CHCH₂OH |
| CH(CH₂OH)CH₂ | CH(CH₂OH)CH₂ |
| | 4-GeMe₂R¹³; |
| 4-GeMe₂R¹³; | R⁵ = SN(Me)CO₂Bu; |
| R⁵ = Me; R¹³ = CH₂OEt | R¹³ = CH₂OEt |
| CH₂ | CH₂ |
| CH₂CH₂ | CH₂CH₂ |
| CHMe | CHMe |
| CHEt | CHEt |
| CHiPr | CHiPr |
| CH(Me)CH₂ | CH(Me)CH₂ |
| CHCH₂OH | CHCH₂OH |
| CH(CH₂OH)CH₂ | CH(CH₂OH)CH₂ |

Formulation and Use

The compounds of this invention will generally be used in formulation with an agriculturally suitable carrier comprising a liquid or solid diluent or an organic solvent. Useful formulations of the compounds of Formula I can be prepared in conventional ways. They include dusts, granules, baits, pellets, solutions, suspensions, emulsions, wettable powders, emulsifiable concentrates, dry flowables and the like. Many of these can be applied directly. Sprayable formulations can be extended in suitable media and used at spray volumes of from about one to several hundred liters per hectare. High strength compositions are primarily used as intermediates for further formulation. The formulations, broadly, contain from less than about 1% to 99% by weight of active ingredient(s) and at least one of a) about 0.1% to 20% surfactant (s) and b) about 5% to 99% solid or liquid diluent(s). More specifically, they will contain effective amounts of these ingredients in the following approximate proportions:

|  | Percent by Weight | | |
| --- | --- | --- | --- |
|  | Active Ingredient | Diluent(s) | Surfactant(s) |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvent are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, U.S. Pat. No. 3,060,084). Granules and pellets can be made by spraying the active material upon preformed granular carriers or by agglomeration techniques. See J. E. Browning, "Agglomeration", *Chemical Engineering*, Dec. 4, 1967, pages 147 and following, and "Perry's Chemical Engineer's Handbook", 4th Ed., McGraw-Hill, New York, 1963, pages 8 to 59 and following.

EXAMPLE A

Emulsifiable Concentrate

| 5-chloro-6-ethyl-N-[2-[4-(trimethylsilyl)phenyl]-ethyl]-4-pyrimidinamine | 20% |
| --- | --- |
| blend of oil soluble sulfonates and polyoxyethylene ethers | 10% |
| isophorone | 70% |

The ingredients are combined and stirred with gentle warming to speed solution. A fine screen filter is included in packaging operation to insure the absence of any extraneous undissolved material in the product.

EXAMPLE B

Wettable Powder

| 5-chloro-6-ethyl-N-[2-(2-naphthalenyl)ethyl]-4-pyrimidinamine | 30% |
| --- | --- |
| sodium alkylnaphthalenesulfonate | 2% |
| sodium ligninsulfonate | 2% |
| synthetic amorphous silica | 3% |
| kaolinite | 63% |

The active ingredient is mixed with the inert materials in a blender. After grinding in a hammermill, the material is re-blended and sifted through a 50 mesh screen.

EXAMPLE C

Dust

| Wettable powder of Example B | 10% |
| --- | --- |
| pyrophyllite (powder) | 90% |

The wettable powder and the pyrophyllite diluent are thoroughly blended and then packaged. The product is suitable for use as a dust.

EXAMPLE D

Granule

| β-[(5-chloro-6-ethyl-4-pyrimidinyl)amino]-4-(1,1-dimethylethyl)benzeneethanol | 10% |
| --- | --- |
| attapulgite granules (low volative matter, 0.71/0.30 mm; U.S.S No. 25–50 sieves) | 90% |

The active ingredient is dissolved in a volatile solvent such as acetone and sprayed upon dedusted and prewarmed attapulgite granules in a double cone blender. The acetone is then driven off by heating. The granules are then allowed to cool and are packaged.

EXAMPLE E

Granule

| Wettable powder of Example B | 15% |
| --- | --- |
| gypsum | 69% |
| potassium sulfate | 16% |

The ingredients are blended in a rotating mixer and water sprayed on to accomplish granulation. When most of the material has reached the desired range of 0.1 to 0.42 mm (U.S.S. No. 18 to 40 sieves), the granules are removed, dried, and screened. Oversize material is crushed to produce additional material in the desired range. These granules contain 4.5% active ingredient.

EXAMPLE F

Solution

| α-[(5-chloro-6-ethyl-4-pyrimidinyl)amino]-4-(1,1-dimethylethyl)benzeneacetamide | 25% |
| --- | --- |
| N-methyl-pyrrolidone | 75% |

The ingredients are combined and stirred to produce a solution suitable for direct, low volume application.

EXAMPLE G

Aqueous Suspension

| | |
|---|---|
| methyl α-[(5-chloro-6-ethyl-4-pyrimidinyl)amino]-4-(1,1-dimethylethyl)benzeneacetate | 40% |
| polyacrylic acid thickener | 0.3% |
| dodecyclophenol polyethylene glycol ether | 0.5% |
| disodium phosphate | 1.0% |
| monosodium phosphate | 0.5% |
| polyvinyl alcohol | 1.0% |
| water | 56.7% |

The ingredients are blended and ground together in a sand mill to produce particles substantially all under 5 microns in size.

EXAMPLE H

Oil Suspension

| | |
|---|---|
| 7-chloro-2,3,3a,4-tetrahydro-3a-oxiranyl-N-[4-(trifluoromethyl)phenyl][1]benezopyarno-[4,3-C]pyrazole-2-carboxamide | 35.0% |
| blend of polyalchohol carboxylic esters and oil soluble petroleum sulfonates | 6.0% |
| xylene range solvent | 59.0% |

The ingredients are combined and ground together in a sand mill to produce particles substantially all below 5 microns. The product can be used directly, extended with oils, or emulsified in water.

EXAMPLE I

Bait Granules

| | |
|---|---|
| 5-chloro-6-ethyl-N-[1-[4-(trimethylsilyl)phenyl]propyl]-4-pyrimidinamine | 3.0% |
| blend of polyethoxylated nonylphenols and sodium dodecylbenzene sulfonates | 9.0% |
| ground up corn cobs | 88.0% |

The active ingredient and surfactant blend are dissolved in a suitable solvent such as acetone and sprayed onto the ground corn cobs. The granules are then dried and packaged.

Compounds of Formula I can also be mixed with one or more other insecticides, fungicides, nematocides, bactericides, acaricides, or other biologically active compounds to form a multi-component pesticide giving an even broader spectrum of effective agricultural protection. Examples of other agricultural protectants with which compounds of this invention can be formulated are:

Insecticides:
3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl O-(methylcarbamoyl)thiolacetohydroxamate (methomyl)
N'-(4-chloro-o-tolyl)-N,N-dimethylformamidine (chlordimeform)
O,O-diethyl-O-(2-isopropyl-4-methyl-6-pyrimidylphosphorothioate (diazinon)
octachlorocamphene (toxaphene)
O-ethyl-O-p-nitrophenyl phenylphosphonothioate (EPN)
(S)-α-cyano-m-phenoxybenzyl(1R, 3R) -3-(2,2-dibromovinyl)-2,2-dimethylcyclopropanecarboxylate (deltamethrin)
Methyl-N',N'-dimethyl-N-[(methylcarbamoyl)oxy]-1-thioox amimidate (oxamyl)
cyano (3-phenoxyphenyl)-methyl -4-chloro-a-(1-methylethyl)benzeneacetate (fenvalerate)
(3-phenoxyphenyl)methyl(+)-cis,trans-3-(2,2-dichloroethenyl)-2,2-dimethylcyclopropanecarboxylate (permethrin)
α-cyano-3-phenoxybenzyl 3-(2,2-dichlorovinyl)-2,2-dimethylcyclopropane carboxylate (cypermethrin)
O-ethyl-S-(p-chlorophenyl)ethylphosphonodithioate (profenofos)
phosphorothiolothionic acid,
O-ethyl-O-[4-(methylthio)-phenyl]-S-n-propyl ester (sulprofos).

Additional insecticides are listed hereafter by their common names: triflumuron, diflubenzuron, methoprene, buprofezin, thiodicarb, acephate, azinphosmethyl, chlorpyrifos, dimethoate, fonophos, isofenphos, methidathion, methamidiphos, monocrotphos, phosmet, phosphamidon, phosalone, pirimicarb, phorate, terbufos, trichlorfon, methoxychlor, bifenthrin, biphenate, cyfluthrin, fenpropathrin, fluvalinate, flucythrinate, tralomethrin, metaldehyde and rotenone.

Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
1-[2-(2,4-dichlorophenyl)-4-propyl-1,3-dioxolan-2-yl-methyl]-1H-2,4-triazole (propiconazole)
2-cyano-N-ethylcarbamoyl-2-methoxyiminoacetamide (cymoxanil)
1-(4-chlorophenoxy)-3,3-dimethyl-1-(1H-1, 2,4-triazol-1-yl)-2-butanone (triadimefon)
N-(trichloromethylthio)tetrahydrophthalimide (captan)
N-(trichloromethylthio)phthalimide (folpet)
dimethyl 4,4'-(o-phenylene) bis (3-thioallophanate) (thiophanate-methyl)
2-(thiazol-4-yl)benzimidazole (thiabendazole)
aluminum tris (O-ethylphosphonate) (phosethyl aluminum)
tetrachloroisophthalonitrile (chlorothalonil)
2,6-dichloro-4-nitroaniline (dichloran)
N- (2,6-dimethylphenyl)-N-(methoxyacetyl)alanine methyl ester (metalaxyl)
cis-N-[1,1,2,2-tetrachloroethyl)thio]cyclohex4-ene-1,2-dicarbioximide (captafol)
3-(3,5-dichlorophenyl)-N-(2-methylethyl)-2,4-dioxolimidazolidine carboxamide (iprodione)
3-(3,5-dichlorophenyl)-5-ethenyl-5-methyl-2,4-oxazolidinedione (vinclozolin)
kasugamycin
O-ethyl-S,S-diphenylphosphorodithioate (edifenphos)

4-(3-(4-(1,1-dimethylethyl)phenyl-2-methyl)propyl-2,6-dimethylmorpholine (fenpropimorph)
4-(3-4(1,1-dimethylethyl)phenyl)-2-methyl)propyl-piperidine (fenpropidine)
2-(4-chlorophenyl)-2-(1H-1,2,4-triazol-1-ylmethyl)hexanenitrile (myclobutanil)
1-[2-(4-chlorophenyl)ethyl]-1-(1,1-dimethylethyl)-1-(1H-1,2,4-triazole-1-yl)ethanol (tebuconazol)
3-chloro-4-[4-methyl-2-(1H-1,2,4-triazol)-1-ylmethyl)-1,3-dioxolan-2-yl]phenyl-4-chlorophenyl ether (difenoconazole)
1-[2-(2,4-dichlorophenyl)pentyl]-1H-1,2,4-triazole (penconazole)
2,4'-difluoro-1-(1H-1,2,4-triazole-1-ylmethyl)benzhydryl alcohol (flutriafol)
1-[[[bis(4-fluorophenyl)]methylsilyl]methyl]-1H-1,2,4-triazole (flusilazole)
N-propyl-N-[2-(2,4,6-trichlorophenoxy)ethyl-]imidazole-1-carboxamide (prochloraz)
1-[2-(2,4-dichlorophenyl)-4-propyl-1,3-dioxolan-2-ylmethyl]-1H-1,2,4-triazole (propiconazole)
1-(2-chlorophenyl)-1-(4-chlorophenyl)-1-(5-pyrimidin)-methanol (fenarimol)
1-(4-chlorophenoxy)-3,3-dimethyl-1-(1H-1, 2,4-triazole-1-yl)butan-2-ol (triadimenol)
1-(2,4-dichlorophenyl)-4,4-dimethyl-2-(1H-1,2,4-triazol-1-yl)pentan-3-ol (diclobutrazol)
copper oxychloride
methyl N(2,6-dimethylphenyl)-N-(2-furanylcarbonyl)-DL-alaninate (furalaxyl)
N-(trichloromethylthio)phthalimide (folpet)
Nematocides:
S-methyl 1-(dimethylcarbamoyl)-N-(methylcarbamoyloxy)thioformimidate
S-methyl 1-carbamoyl-N-(methylcarbamoyloxy)thioformimidate
N-isopropylphosphoramidic acid O-ethyl O'-[4-(methylthio)-m-tolyl]diester (fenamiphos)
Bactericides:
tribasic copper sulfate
streptomycin sulfate
Acaricides:
senecioic acid, ester with 2-sec-butyl-4,6-dinitrophenol (binapacryl)
6-methyl-1,3-cithiolo[4,5-β]quinoxalin-2-one (oxythioquinox)
ethyl 4,4'-dichlorobenzilate (chlorobenzilate)
1,1-bis(p-chlorophenyl)-2,2,2-trichloroethanol (dicofol)
bis(pentachloro-2,4-cyclopentadien-1-yl) (dienochlor)
tricyclohexyltin hydroxide (cyhexatin)
trans-5-(4-chlorophenyl)-N-cyclohexyl-4-methyl-2-oxothiazolidine-3-carboxamide (hexythiazox)
amitraz
propargite
fenbutatin-oxide
Biological
Bacillus thuringiensis
Avermectin B.

Utility

The compounds of this invention are useful against agronomic and nonagronomic pests. They exhibit activity against a wide spectrum of foliar and soil inhabiting arthropods which are pests of growing and stored agronomic crops, forestry, greenhouse crops, ornamentals, nursery crops, stored food and fiber products, livestock, household, and public and animal health. Those skilled in the art will recognize that not all compounds are equally effective against all pests but the compounds of this invention display activity against economically important agronomic, forestry, greenhouse, ornamental food and fiber product, stored product, domestic structure, and nursery pests, such as:

larvae of the order Lepidoptera including fall and beet armyworm and other *Spodoptera spp.*, tobacco budworm, corn earworm and other *Heliothis spp.*, European corn borer, navel orangeworm, stalk/-stem borers and other pyralids, cabbage and soybean loopers and other loopers, codling moth, grape berry moth and other tortricids, black cutworm, spotted cutworm, other cutworms and other noctuids, diamondback moth, green cloverworm, velvetbean caterpillar, green cloverworm, pink bollworm, gypsy moth, and spruce budworm;

foliar feeding larvae and adults of the order Coleoptera including Colorado potato beetle, Mexican bean beetle, flea beetle, Japanese beetles, and other leaf beetles, boll weevil, rice water weevil, granary weevil, rice weevil and other weevil pests, and soil inhabiting insects such as Western corn rootworm and other *Diabrotica spp.*, Japanese beetle, European chafer and other coleopteran grubs, and wireworms;

adults and larvae of the orders Hemiptera and Homoptera including tarnished plant bug and other plant bugs (*miridae*), aster leafhopper and other leafhoppers (*cicadellidae*), rice planthopper, brown planthopper, and other planthoppers (*fulgoroidea*), psylids, whiteflies (*aleurodidae*), aphids (*aphidae*), scales (*coccidae* and *diaspididae*), lace bugs (*tingidae*), stink bugs (*pentatomidae*), cinch bugs and other seed bugs (*lygaeidae*), cicadas (*cicadidae*), spittlebugs (*cercopids*), squash bugs (*coreidae*), red bugs and cotton stainers (*pyrrhocoridae*);

adults and larvae of the order *acari* (mites) including European red mite, two spotted spider mite, rust mites, McDaniel mite, and foliar feeding mites;

adults and inunatures of the order Orthoptera including grasshoppers;

adults and inunatures of the order Diptera including leafminers, midges, fruit flies (*tephritidae*), and soil maggots;

adults and immatures of the order Thysanoptera including onion thrips and other foliar feeding thrips.

The compounds are also active against economically important livestock, household, public and animal health pests such as:

insect pests of the order Hymenoptera including carpenter ants, bees, hornets, and wasps;

insect pests of the order Diptera including house flies, stable flies, face flies, horn flies, blow flies, and other muscoid fly pests, horse flies, deer flies and other Brachycera, mosquitoes, black flies, biting midges, sand flies, sciarids, and other Nematocera;

insect pests of the order Orthoptera including cockroaches and crickets;

insect pests of the order Isoptera including the Eastern subterranean termite and other termites;

insect pests of the order Mallophaga and Anoplura including the head louse, body louse, chicken head louse and other sucking and chewing parasitic lice that attack man and animals;

insect pests of the order Siphonoptera including the cat flea, dog flea and other fleas.

Finally, the compounds of this invention are useful as plant disease control agents. They provide control of diseases caused by a broad spectrum of fungal plant pathogens in the Basidiomycete, Ascomycete and Oomycete classes. They are effective in controlling a broad spectrum of plant diseases, particularly foliar pathogens of ornamental, vegetable, field, cereal, and fruit crops. These pathogens include, *Venturia inaequalis, Cercosporidium personatum, Cercospora arachidicola, Cercospora beticola, Pseudocercosporella herpotrichoides, Erysiphe graminis, Uncinula necatur, Podosphaera leucotricha, Puccinia recondita, Puccinia graminis, Hemileia vastatrix, Puccinia striiformis, Puccinia arachidis, Pyricularia oryzae, Phytophthora infestaris, Plasmopara viticola, Peronospora tabacina, Pseudoperonospora cubensis, Pythium aphanidermatum* and other species closely related to these pathogens. They also control seed pathogens.

The specific species for which arthropod control is exemplified are: fall armyworm, *Spodoptera fruigiperda*; tobacco budworm, *Heliothis virescens* (Helicoverpa); boll weevil, *Anthonomus grandis*; aster leafhopper, *Macrosteles fascifrons*; black bean aphid, (*Aphis Fabae*); southern corn rootworm, *Diabrotica undecimpunctata* and two-spotted spider mite (*Tetranychus urt*). The pest control protection afforded by the compounds of the present invention is not limited, however, to these species. The compounds of this invention may also be utilized as rodenticides.

The specific plant pathogens for which control is exemplified are: *Ventura inaequalis* (the causal agent of apple scab); *Cercosporidium personatum* (the causal agent of peanut late leafspot); *Erysiphe graminis f. sp. tritici* (the causal agent of wheat powdery mildew); *Puccinia cecondita* (the causal agent of wheat leaf rust); and *Plasmopara viticola* (the causal agent of grape downey mildew). The plant pathogen control protection afforded by the compounds of the present invention is not limited, however, to these species.

Application

Arthropod pests are controlled and protection of agronomic crops, animal and human health is achieved by applying one or more of the Formula I compounds of this invention, in an effective amount, to the environment of the pests including the agronomic and/or nonagronomic locus of infestation, to the area to be protected, or directly on the pests to be controlled. Because of the diversity of habitat and behavior of these arthropod pest species, many different methods of application are employed. A preferred method of application is by spraying with equipment that distributes the compound in the environment of the pests, on the foliage, animal, person, or premise, in the soil or animal, to the plant part that is infested or needs to be protected. Alternatively, granular formulations of these toxicant compounds can be applied to or incorporated into the soil. Other methods of application can also be employed including direct and residual sprays, aerial sprays, baits, eartags, boluses, foggets, aerosols, and many others. The compounds can be incorporated into baits that are consumed by the arthropods or in devices such as traps and the like which entice them to ingest or otherwise contact the compounds.

Plant disease control is ordinarily accomplished by applying an effective amount of the compound either preinfection or post-infection to the portion of the plant to be protected such as the roots, stems, foliage, fruit, seeds, tubers or bulbs, or to the media (soil or sand) in which the plants to be protected are growing. The compound may also be applied to the seed, to protect the seed and seedling.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrates, and synergists such as piperonyl butoxide often enhance the efficacy of the compounds of Formula I.

The rate of application of the Formula I compounds required for effective arthropod control will depend on such factors as the species of arthropod to be controlled, the pest's life cycle, life stage, its size, location, time of year, host crop or animal, feeding behavior, mating behavior, ambient moisture, temperature, etc. In general, application rates of 0.01 to 2 kg of active ingredient per hectare are sufficient to provide large-scale effective control of pests in agronomic ecosystems under normal circumstances, but as little as 0.001 kg/hectare or as much as 8 kg hectare may be required. For nonagronomic applications, effective use rates will range from about 1.0 to 50 mg/square meter but as little as about 0.1 mg/square meter or as much as 150 mg/square meter may be required.

Rates of application for these compounds as plant disease control agents can be influenced by many factors of the environment and should be determined under actual use conditions. Foliage can normally be protected when treated at a rate of from less than 10 g/ha to 10,000 g/ha of active ingredient. Plants growing in soil treated at a concentration from 0.1 to about 20 kg/ha can be protected from disease. Seed and seedlings can normally be protected when seed is treated at a rate of from 0.1 to 10 g per kilogram of seed.

The following tests demonstrate the control efficacy of compounds of Formula I on specific pests and plant pathogens; see Index Tables A and B for compound descriptions. Compounds for which no data are reported were either not screened or have activities lower than the recited minimum values.

INDEX TABLE A

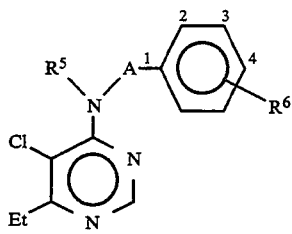

| CMPD | R[5] | A | R[6] | mp (°C.) |
|---|---|---|---|---|
| 1 | H | CHC(O)NH$_2$ | 4-tBu | glass[a] |
| 2 | H | CHCO$_2$Me | 4-tBu | wax[b] |
| 3 | H | CHCO$_2$H | 4-tBu | solid[c] |
| 4 | H | CHCO$_2$Me | 3-O-(4-F-Ph) | oil[d] |
| 5 | H | CHC(O)NH$_2$ | 3-O-(4-F-Ph) | oil[e] |
| 6 | H | CHCH$_2$OH | 4-tBu | 118–120 |
| 7 | H | CH(CO$_2$Me)CH$_2$ | 4-tBu | oil[f] |
| 8 | H | CH$_2$CH$_2$ | 4-SiMe$_3$ | 101–103 |
| 9 | H | CHEt | 4-SiMe$_3$ | oil[g] |
| 10 | H | CHCMe$_2$(OH) | 4-tBu | 158–160 |
| 11 | H | CH(CO$_2$Me)CH$_2$ | 4-F | 75–78 |
| 12 | H | CH$_2$CH$_2$ | 4-SiMe$_2$(tBu) | 110–112 |
| 13 | H | CHCHMe(OH) | 4-tBu | wax[h] |
| 14 | H | CHCH$_2$OC(O)Me | 4-tBu | oil[i] |
| 15 | H | CH(CH$_2$OH)CH$_2$ | 4-tBu | 128–130 |
| 16 | H | CH(CO$_2$Bu)CH$_2$ | 4-F | oil[j] |
| 17 | H | CHCH$_2$OCMe$_2$(OMe) | 4-tBu | oil[k] |
| 18 | H | CHiPr | 4-SiMe$_3$ | oil[l] |
| 19 | C(O)imidazole | CH$_2$CH$_2$ | 4-SiMe$_3$ | oil[m] |
| 20 | H | CH$_2$CH$_2$ | 4-SiMe$_3$ | 184–186 (HCl salt) |
| 21 | H | CH$_2$CH$_2$ | 4-SiEt$_3$ | 77–79 |
| 22 | H | CH$_2$CH$_2$ | 4-SiMe$_2$(Ph) | 71–73 |
| 23 | H | CHCH$_2$OCH$_2$CH$_2$OEt | 4-tBu | oil[n] |
| 24 | H | CHMe | 4-SiMe$_3$ | 78–80 |
| 25 | H | CHCO$_2$CH$_2$CH$_2$OMe | 4-tBu | oil[o] |
| 26 | H | CH(Me)CH(OSiMe$_3$) | 4-tBu | oil[p] |
| 27 | H | CH(Me)CH(OSiMe$_3$) | 4-tBu | oil[q] |
| 28 | H | CHCO$_2$C$_7$H$_{15}$ | 4-tBu | oil[r] |
| 29 | H | CH$_2$CH(Me)CH(OSiMe$_3$) | 4-tBu | oil[s] |
| 30 | H | CHCH$_2$OC(O)Bu | 4-tBu | oil[t] |
| 31 | H | CH(CO$_2$CH$_2$Ph)CH$_2$ | 4-tBu | 94–97 |
| 32 | H | CHCH$_2$OCH$_2$Ph | 4-tBu | oil[u] |
| 33 | H | CH$_2$CH(Me)CH(OH) | 4-tBu | 107–110 |
| 34 | H | CH(Me)CH(OH) | 4-tBu | glass[v] |
| 35 | H | CH(Me)CH(OH) | 4-tBu | glass[w] |
| 36 | H | CH[CH$_2$OC(O)Me]CH$_2$ | 4-tBu | oil[x] |
| 37 | H | CH[CH$_2$OCMe$_2$(OMe)]CH$_2$ | 4-tBu | oil[y] |
| 38 | Me | CH$_2$CH$_2$ | 4-SiMe$_3$ | oil[z] |
| 39 | H | CH(CH$_2$OCH$_2$Ph)CH$_2$ | 4-tBu | oil[aa] |
| 40 | H | CH$_2$CH$_2$ | 3-SiMe$_3$ | 93–95 |
| 41 | H | CHMe | 4-SiMe$_3$ | 196–199 (HCl salt) |
| 42 | H | CHCN | 4-tBu | wax[bb] |
| 43 | H | CHMe | 4-SiMe$_3$ | $[\alpha]_D^{25} = +15.9$ |
| 44 | H | CHMe | 4-SiMe$_3$ | $[\alpha]_D^{25} = -13.9$ |
| 45 | H | CHCN | 3-O-(4-F-Ph) | glass[cc] |
| 46 | H | CHCH$_2$OCH$_2$CF$_3$ | 4-tBu | oil[dd] |
| 47 | H | CH$_2$CH$_2$ | 4-CO$_2$Et | 134–135 |
| 48 | H | CH$_2$CH$_2$ | 4-CO$_2$CH$_2$CF$_3$ | oil |
| 49 | H | CHMe | 4-CO$_2$Et | 101–102 |
| 50 | H | CH$_2$CH$_2$ | 4-CO$_2$Me | 138–139 |
| 51 | H | CH$_2$CH$_2$ | 4-C(O)Ph | wax[ee] |
| 52 | H | CH$_2$CH$_2$ | 4-C(O)iPr | oil[ff] |
| 53 | H | CH$_2$CH$_2$ | 4-C(O)Et | 116–118 |
| 54 | H | CH$_2$CH$_2$ | 4-C(O)(4-Cl—Ph) | oil[gg] |
| 55 | H | CH$_2$CH$_2$ | 4-C(O)nPr | 104–107 |
| 56 | H | CH$_2$CH$_2$ | 4-C(O)(2-Cl—Ph) | oil[hh] |
| 57 | H | CH$_2$CH$_2$ | 4-C(O)(3-Cl—Ph) | 99–101 |
| 58 | H | CH$_2$CH$_2$ | 4-C(O)(4-F—Ph) | 109–110 |
| 59 | H | CH$_2$CH$_2$ | 4-C(O)(2,4-di-Cl—Ph) | oil[ii] |
| 60 | H | CH$_2$CH$_2$ | 4-C(O)(3,5-di-Cl—Ph) | wax[jj] |
| 61 | H | CH$_2$CH$_2$ | 4-C(O)Me | 94–96 |
| 62 | H | CH$_2$CH$_2$ | 4-C(O)(2,4-di-F—Ph) | 95–97 |
| 63 | H | CH$_2$CH$_2$ | 4-C(O)CH$_2$Ph | oil[kk] |
| 64 | H | CH$_2$CH$_2$ | 4-C(O)(3,4-di-F—Ph) | oil[ll] |
| 65 | H | CH$_2$CH$_2$ | 4-C(O)iBu | oil |
| 66 | H | CH$_2$CH$_2$ | 4-CO$_2$iPr | 105–106 |

-continued

INDEX TABLE A

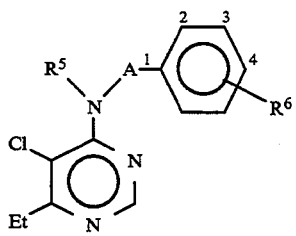

| CMPD | R⁵ | A | R⁶ | mp (°C.) |
|---|---|---|---|---|
| 78 | H | CHMe | 4-GeMe₃ | 74–77 |

INDEX TABLE B

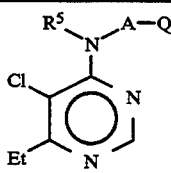

| CMPD | R⁵ | A | Q | mp (°C.) |
|---|---|---|---|---|
| 67 | H | CH₂ | 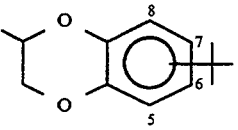 | oil^mm |
| 68 | H | CH₂ | 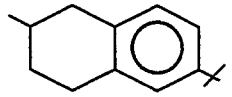 | oil^nn |
| 69 | H | CH₂CH₂ | 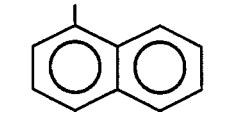 | 92–95 |
| 70 | H | CH₂CH₂ | 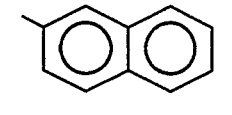 | 79–83 |
| 71 | Et | CH₂ | 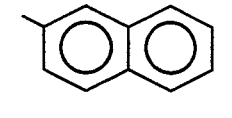 | oil^oo |
| 72 | Me | CH₂ | 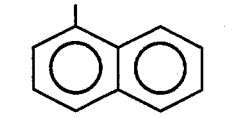 | oil^pp |
| 73 | H | CHEt | 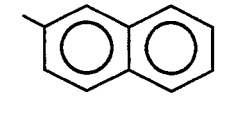 | oil^qq |
| 74 | H | CHMe |  | 79–82 |

INDEX TABLE B-continued

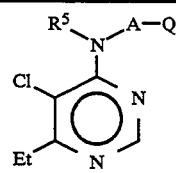

| CMPD | R⁵ | A | Q | mp (°C.) |
|---|---|---|---|---|
| 75 | H | CHMe | 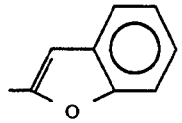 | 96–98 |
| 76 | H | CHMe | 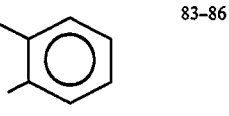 | 83–86 |
| 77 | H | CHMe | 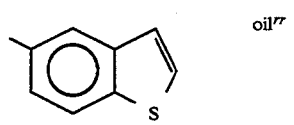 | oil^rr |

¹HNMR $^a$(CDCl₃): δ 8.39 (s, 1H), 7.41 (s, 4H), 6.60 (brd, 1H), 5.69 (brs, 2H), 5.63 (d, 1H), 2.78 (q, 2H), 1.31 (s, 9H), 1.24 (t, 3H).

$^b$(CDCl₃): δ 8.40 (s, 1H), 7.39 (s, 4H), 6.22 (brd, 1H), 5.73 (d, 1H), 3.76 (s, 3H), 2.80 (q, 2H), 1.31 (s, 9H), 1.25 (t, 3H).

$^c$(DMSO-d₆): δ 8.33 (s, 1H), 7.37 (s, 4H), 7.10 (d, 1H), 5.60 (d, 1H), 3.30 (brs, 1H), 2.72 (q, 2H), 1.25 (s, 9H), 1.15 (t, 3H).

$^d$(CDCl₃): δ 8.38 (s, 1H), 7.32 (m, 2H), 7.20-6.05 (m, 6H), 6.33 (brd, 1H), 5.74 (d, 1H), 3.77 (s, 3H), 2.80 (q, 2H), 1.26 (t, 3H).

$^e$(CDCl₃): δ 8.28 (s, 1H), 7.40-6.85 (m, 8H), 6.66 (d, 1H), 5.67 (brd, 1H), 5.60 (d, 1H), 2.80 (q, 2H), 1.25 (t, 3H).

$^f$(CDCl₃): δ 8.40 (s, 1H), 7.30, 7.08 (ABq, 4H), 5.78 (brd, 1H), 5.06 (q, 1H), 3.75 (s, 3H), 3.19 (m, 2H), 2.78 (q, 2H), 1.30 (s, 9H), 1.25 (t, 3H).

$^g$(CDCl₃): δ 8.38 (s, 1H), 7.49, 7.32 (ABq, 4H), 5.65 (brd, 1H), 5.15 (q, 1H), 2.78 (q, 2H), 1.93 (m, 2H), 1.25 (t, 3H), 0.96 (t, 3H), 0.26 (s, 9H).

$^h$(CDCl₃): δ 8.35 (s, 1H), 7.38, 7.32 (ABq, 4H), 6.26 (brd, 1H), 5.19 (m, 1H), 4.20 (m, 1H), 2.79 (q, 2H), 2.32 (brd, 1H), 1.31 (s, 9H), 1.28 (t, 3H), 1.17 (d, 3H).

$i$(CDCl$_3$): δ 8.40 (s, 1H), 7.39, 7.30 (ABq, 4H), 5.98 (brd, 1H), 5.55 (m, 1H), 4.42 (d, 2H), 2.79 (q, 2H), 2.05 (s, 3H), 1.31 (s, 9H), 1.26 (t, 3H).

$j$(CDCl$_3$): δ 8.41 (s, 1H), 7.10 (m, 2H, 7.00 (m, 2H), 5.82 (d, 1H), 5.05 (q, 1H), 4.12 (m, 2H), 3.19 (d, 2H), 2.80 (q, 2H), 1.58 (m, 2H), 1.26 (m, 5H), 0.91 (t, 3H).

$k$(CDCl$_3$): δ 8.36 (s, 1H), 7.34, 7.31 (ABq, 4H), 6.18 (brd, 1H), 5.37 (m, 1H), 3.75 (m, 2H), 3.03 (s, 3H), 2.80 (q, 2H), 1.30 (m, 18H).

$l$(CDCl$_3$): δ 8.35 (s, 1H), 7.47, 7.27 (ABq, 4H), 5.78 (d, 1H), 5.06 (t, 1H), 2.77 (q, 2H), 2.18 (m, 1H), 1.24 (t, 3H), 1.00 (d, 3H), 0.92 (d, 3H), 0.24 (s, 9H).

$m$(CDCl$_3$): δ 8.68 (s, 1H), 7.63 (s, 1H), 7.38, 7.17 (ABq, 4H), 6.88 (s, 2H), 4.25 (t, 2H), 3.06 (t, 2H), 2.82 (q, 2H), 1.20 (t, 3H), 0.23 (s, 9H).

$n$( CDCl$_3$): δ 8.34 (s, 1H), 7.35, 7.30 (ABq, 4H), 6.18 (d, 1H), 5.40 (q, 1H), 3.85 (m, 2H), 3.70-3.45 (m, 4H), 2.78 (q, 2H), 1.30 (s, 9H), 1.21 (m, 6H).

$o$(CDCl$_3$): δ 8.40 (s, 1H), 7.40 (s, 4H), 6.14 (brd, 1H), 5.97 (d, 1H), 4.30 (m, 2H), 3.55 (t, 2H), 3.28 (s, 3H), 2.80 (q, 2H), 1.31 (s, 9H), 1.25 (t, 3H).

$p$(CDCl$_3$): δ 8.43 (s, 1H), 8.30, 8.25 (ABq, 4H), 5.65 (brd, 1H), 4.96 (d, 1H), 4.42 (m, 1H), 2.80 (q, 2H), 1.32 (s, 9H), 1.27 (t, 3H), 0.98 (d, 3H), 0.45 (s, 9H), single diastereomer $q$(CDCl$_3$): δ 8.25 (s, 1H), 7.24, 7.18 (ABq, 4H), 5.72 (brd, 1H), 4.73 (d, 1H), 4.36 (m, 1H), 2.76 (q, 2H), 1.27 (s, 9H), 1.23 (m, 6H), 0.92 (s, 9H), single diastereomer $r$(CDCl$_3$): δ 8.40 (s, 1H), 7.39 (s, 4H), 6.28 (brd, 1H), 5.72 (d, 1H), 4.16 (m, 2H), 2.80 (q, 2H), 1.60 (m, 2H), 1.32 (s, 9H), 1.15 (m, 9H), 0.85 (m, 5H).

$s$(CDCl$_3$): δ 8.30 (s, 1H), 7.26, 7.13 (ABq, 4H), 6.35 (m, 1H), 4.70 (d, 1H), 4.60 (d, 1H), 3.40 (m, 2H), 2.73 (q, 2H), 2.18 (m, 1H), 2.00 (m, 1H), 1.25 (s, 9H), 1.21 (t, 3H), 0.98 (d, 3H), 0.82 (d, 3H), 0.00 (s, 9H), mixture of diastereomers $t$(CDCl$_3$): δ 8.39 (s, 1H), 7.38, 7.30 (ABq, 4H), 5.98 (brd, 1H), 5.58 (m, 1H), 4.55 (dd, 1H), 4.35 (dd, 1H), 2.79 (q, 2H), 2.29 (t, 2H), 1.65-1.45 (m, 2H), 1.31 (s, 9H), 1.26 (m, 5H), 0.84 (t, 3H).

$u$(CDCl$_3$): δ 8.35 (s, 1H), 7.40-7.20 (m, 9H), 6.13 (d, 1H), 5.42 (m, 1H), 4.56 (s, 2H), 3.80 (m, 2H), 2.79 (q, 2H), 1.30 (s, 9H), 1.29 (t, 3H).

$v$(CDCl$_3$): δ 8.41 (s, 1H), 7.38, 7.10 (ABq, 4H), 7.49 (d, 1H), 4.95 (m, 1H), 4.59 (m, 1H), 3.65 (d, 1H), 2.80 (q, 2H), 1.32 (s, 9H), 1.27 (t, 3H), 1.13 (d, 3H), single diastereomer $w$(CDCl$_3$): δ 8.34 (s, 1H), 7.35, 7.28 (ABq, 4H), 5.60 (d, 1H), 4.69 (t, 1H), 4.45 (m, 1H), 3.38 (d, 1H), 2.78 (q, 2H), 1.30 (s, 9H), 1.23 (m, 6H), single diastereomer $x$(CDCl$_3$): δ 8.42 (s, 1H), 7.32, 7.16 (ABq, 4H), 5.54 (d, 1H), 4.70 (brm, 1H), 4.16 (d, 2H), 3.05-2.85 (m, 2H), 2.79 (q, 2H), 2.09 (s, 3H), 1.30 (s, 9H), 1.26 (t, 3H).

$y$(CDCl$_3$): δ 8.40 (s, 1H), 7.30, 7.18 (ABq, 4H), 5.78 (brd, 1H), 4.55 (brm, 1H), 3.45 (d, 3H), 3.20 (d, 3H), 2.95 (m, 2H ), 2.78 ( q, 2H), 1.40-1.20 (m, 18H).

$z$(CDCl$_3$): δ 8.43 (s, 1H), 7.45, 7.22 (ABq, 4H), 3.78 (m, 2H), 3.18 (s, 3H), 2.96 (m, 2H), 2.84 (q, 2H), 1.27 (t, 3H), 0.25 (s, 9H).

$aa$(CDCl$_3$): δ 8.40 (s, 1H), 7.34 (m, 5H), 7.28, 7.14 (ABq, 4H), 5.77 (d, 1H), 4.56 (s, 2H), 4.50 (brm, 1H), 3.50 (m, 2H), 2.95 (m, 2H), 2.78 (q, 2H), 1.30 (s, 9H), 1.26 (t, 3H).

$bb$(CDCl$_3$): δ 8.58 (s, 1H), 7.50 (s, 4H), 6.30 (d, 1H), 5.65 (brd, 1H), 2.84 (q, 2H), 1.34 (s, 9H), 1.28 (t, 3H).

$cc$(CDCl$_3$): δ 8.56 (s, 1H), 7.45-6.95 (m, 8H), 6.35 (d, 1H), 5.68 (brd, 1H), 2.84 (q, 2H), 1.29 (t, 3H).

$dd$(CDCl$_3$): δ 8.39 (s, 1H), 7.42, 7.28 (ABq, 4H), 5.90 (brm, 1H), 4.62 (m, 1H), 4.03 (m, 1H), 3.90-3.22 (brm, 3H), 2.81 (q, 2H), 1.33 (s, 9H), 1.27 (t, 3H).

$ee$(CDCl$_3$): δ 8.45 (s, 1H), 7.80-7.30 (m, 10H), 5.45 (s, 1H), 3.84 (m, 2H), 3.07 (m, 2H), 2.80 (m, 2H), 1.30 (m, 3H).

$ff$(CDCl$_3$): δ 8.45 (s, 1H), 7.90, 7.30 (ABq, 4H), 3.80 (t, 2H), 3.50 (m, 1H), 3.00 (t, 2H), 2.80 (q, 2H), 1.20 (m, 9H).

$gg$(CDCl$_3$): δ 8.50 (s, 1H), 7.70-7.30 (m, 8H), 5.60 (s, 1H), 3.80 (t, 2H), 3.00 (t, 2H), 2.80 (q, 2H), 1.30 (t, 3H).

$hh$(CDCl$_3$): δ 8.45 (s, 1H), 7.80 (m, 2H), 7.40 (m, 6H), 5.50 (s, 1H), 3.80 (t, 2H), 3.00 (t, 2H), 2.80 (q, 2H), 1.30 (t, 3H).

$ii$(CDCl$_3$): δ 8.50 ( s, 1H), 7.80-7.20 (m, 7H), 5.45 (s, 1H), 3.80 (t, 2H), 3.10 (t, 2H), 2.80 (q, 2H), 1.20 (t, 3H).

$jj$(CDCl$_3$): 8.45 (s, 1H), 7.80-7.20 (m, 7H), 5.40 (s, 1H), 3.80 (t, 2H), 3.10 (t, 2H), 2.80 (q, 2H), 1.25 (t, 3H).

$kk$(CDCl$_3$): δ 8.40 (s, 1H), 8.00 (m, 2H), 7.20 (m, 7H), 5.40 (s, 1H), 4.30 (t, 2H), 3.90 (t, 2H), 2.90 (s, 2H), 2.70 (q, 2H), 1.20 (t, 3H).

$ll$(CDCl$_3$): δ 8.45 (s, 1H), 7.70-7.20 (m, 7H), 5.50 (s, 1H), 3.80 (t, 2H), 3.00 (t, 2H), 2.80 (q, 2H), 1.26 (t, 3H).

$mm$(CDCl$_3$): δ 8.43 (s, 1H), 6.95-6.80 (m, 3H), 5.80 (brs, 1H), 4.40 (m, 1H), 4.30 (m, 1H), 4.05-3.70 (m, 3H), 2.80 (q, 2H), 1.28 (s, 9H), 1.27 (t, 3H), mixture of 6-tBu and 7-tBu isomers $nn$(CDCl$_3$): δ 8.42 (s, 1H), 7.20-7.00 (m, 3H), 5.55 (brs, 1H), 3.55 (t, 2H), 2.86 (m, 3H), 2.81 (q, 2H), 2.60-2.25 (m, 1H), 2.05 (brm, 2H), 1.60-1.35 (brm, 1H), 1.30 (s, 9H), 1.27 (t, 3H).

$oo$(CDCl$_3$): δ 8.48 (s, 1H), 7.80 (m, 4H), 7.46 (m, 3H), 5.00 (s, 2H), 3.65 (q, 2H), 2.86 (q, 2H), 1.27 (m, 6H).

$pp$(CDCl$_3$): δ 8.51 (s, 1H), 7.90 (m, 2H), 7.82 (m, 1H), 7.49 (m, 4H), 5.26 (s, 2H), 3.16 (s, 3H), 2.87 (q, 2H), 1.29 (t, 3H).

$qq$(CDCl$_3$): δ 8.38 (s, 1H), 7.82 (m, 4H), 7.46 (m, 3H), 5.73 (brd, 1H), 5.30 (q, 1H), 2.77 (q, 2H), 2.03 (m, 2H), 1.25 (t, 3H), 0.99 (t, 3H).

$rr$(CDCl$_3$): δ 8.40 (s, 1H), 7.85 (d, 1H), 7.82 (d, 1H), 7.45 (d, 1H), 7.35 (d, 1H), 7.33 (s, 1H), 5.65 (brd, 1H), 5.58 (m, 1H), 2.79 (q, 2H), 1.66 (d, 3H), 1.26 (t, 3H).

EXAMPLE J

Fall Armyworm

Test units, each consisting of an 8-ounce (230 mL) plastic cup containing a layer of wheat germ diet, approximately 0.5 cm thick, were prepared. Five third-instar larvae of fall armyworm (*Spodoptera frugiperda*) were placed into each cup. Solutions of each of the test compounds (acetone/distilled water 75/25 solvent) were sprayed into the cups. Spraying was accomplished by passing the cups, on a conveyer belt, directly beneath a flat fan hydraulic nozzle which discharged the spray at a rate of 0.5 pounds of active ingredient per acre (about 0.55 kg/ha) at 30 p.s.i. (207 kPa). The cups were then covered and held at 27° C. and 50% relative humidity for 72 hours, after which time readings were taken. Of the compounds tested, the following gave mortality levels of 80% or higher: 8, 14, 20, 30, 40, 41, 54, 56, 57, 58, 59, 60, 62, 63, 64, 65, 66, 68.

EXAMPLE K

Tobacco Budworm

The test procedure of Example J was repeated for efficacy against third-instar larvae of the tobacco budworm (*Heliothis virescens* [Helicoverpa]) except that mortality was assessed at 48 hours. Of the compounds tested, the following gave mortality level of 80% or higher: 8, 30, 47, 54, 55, 58, 59, 62, 63, 66, 68, 70.

EXAMPLE L

Southern Corn Rootworm

The units, each consisting of an 8-ounce (230 mL) plastic cup containing 1 sprouted corn seed, were prepared. The test units were sprayed as described in Example J with individual solutions of the test compounds. After the spray on the cups had dried, five third-instar larvae of the southern corn rootworm (*Diabrotica undecimpunctata howardi*) were placed into each cup. A moistened dental wick was inserted into each cup to prevent drying and the cups were then covered. The cups were then held at 27° C. and 50% relative humidity for 48 hours, after which time mortality readings were taken. Of the compounds tested, the following gave mortality levels of 80% or higher: 4, 5, 9, 11, 14, 15, 18, 21, 22, 24, 32, 36, 40, 41, 47, 52, 53, 54, 55, 56, 57, 58, 59, 61, 62, 63, 64, 66, 69, 72, 73, 74, 76.

EXAMPLE M

Aster Leafhopper

Test units were prepared from a series of 12-ounce (350 mL) cups, each containing oat (*Avena sativa*) seedlings in a 1-inch (2.54 cm) layer of sterilized soil. The test units were sprayed as described in Example J with individual solutions of the below-listed compounds. After the oats had dried from the spraying, between 10 and 15 adult aster leafhoppers (*Macrosteles quadrilineatus*) were aspirated into each of the covered cups. The cups were held at 27° C. and 50% relative humidity for 48 hours, after which time mortality readings were taken. Of the compounds tested, the following gave mortality levels of 80% or higher: 2, 7, 8, 9, 11, 18, 20, 24, 38, 40, 41, 49, 50, 52, 54, 57, 58, 59, 60, 61, 62, 63, 64, 66, 68, 73, 74, 75, 76.

EXAMPLE N

Boll Weevil

Five adult boll weevils (*Anthonomus grandis grandis*) were placed into each of a series of 9 ounce (260 mL) cups. The test procedure employed was then otherwise the same as in Example J. Mortality readings were taken 48 hours after treatment. Of the compounds tested, the following gave mortality levels of 80% or higher: 4, 8, 11, 20, 30, 38, 47, 54, 56, 57, 58, 59, 62, 64, 66, 68, 70, 73, 74.

EXAMPLE O

Black Bean Aphid

Individual nasturtium leaves were infested with 5 to 10 aphids (all stages of *Aphis fabae*) and sprayed with their undersides facing up on a hydraulic sprayer as described in Example J. The leaves were then set in a 15×45 mm shell vial containing sugar water solution and covered with a clear plastic 1 oz (29.57 milliliters) portion cup to prevent escape of aphids that drop from the leaves. The test units were held at 27° C. and 50% relative humidity for 48 hours, after which time mortality readings were taken. Of the compounds tested, the following gave mortality levels of 80% or higher: 1, 2, 4, 6, 7, 8, 9, 11, 14, 15, 17, 18, 19, 20, 21, 22, 24, 25, 30, 36, 37, 38, 39, 40, 41, 47, 49, 50, 51, 52, 53, 54, 55, 56, 57, 58, 59, 60, 61, 62, 63, 64, 65, 66, 67, 68, 69, 70, 74, 75, 76, 78.

EXAMPLE P

Two-Spotted Spider Mite

One inch squares (2.54 centimeters) of kidney bean leaves that have been infested on the undersides with 25 to 30 adult mites (*Tetranychus urticae*) were sprayed with their undersides facing up on a hydraulic sprayer as described in Example J. The leaf squares were placed underside up on a square of wet cotton in a petri dish and the perimeter of the leaf square was tamped down onto the cotton with forceps so that the mites cannot escape onto untreated leaf surface. The test units were held at 27° C. and 50% relative humidity for 48 hours, after which time mortality readings were taken. Of the compounds tested, the following gave levels of 80% or higher: 1, 2, 4, 5, 6, 7, 8, 9, 11, 12, 13, 14, 15, 17, 18, 19, 20, 21, 22, 24, 30, 36, 37, 38, 39, 40, 41, 42, 44, 51, 52, 54, 56, 57, 58, 59, 60, 62, 63, 64, 65, 67, 68, 69, 70, 73, 74, 75, 76, 78.

EXAMPLE Q

The test compounds were dissolved in acetone in an amount equal to 3% of the final volume and then suspended at a concentration of 200 ppm in purified water containing 250 ppm of the surfactant Trem 14 (polyhydric alcohol esters). This suspension was sprayed to the point of run-off on wheat seedlings. The following day the seedlings were inoculated with a spore dust of *Erysiphe graminis f. sp. tritici* (the causal agent of wheat powdery mildew) and incubated growth chamber at 20° C. for 7 days, after which disease ratings were made. Of the compounds tested, the following gave 70% disease control or higher: 7, 8, 9, 11, 12, 14, 15, 16, 17, 18, 19, 20, 21, 22, 23, 24, 25, 26, 27, 29, 30, 32, 33, 35, 36, 37, 38, 39, 40, 41, 49, 50, 52, 53, 54, 55, 56, 57, 58, 59, 60, 61, 62, 65, 67, 68, 70, 71, 72, 73, 74, 75, 76, 78.

EXAMPLE R

The test compounds were dissolved in acetone in an amount equal to 3% of the final volume and then suspended at a concentration of 200 ppm in purified water containing 250 ppm of the surfactant Trem 14 (polyhydric alcohol esters). This suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 hours, and then moved to a growth chamber at 20° C. for 6 days, after which disease ratings were made. Of the compounds tested, the following gave 70% disease control or higher: 6, 7, 8, 9, 11, 14, 15, 17, 18, 19, 20, 21, 22, 23, 24, 25, 30, 36, 37, 38, 40, 41, 42, 45, 48, 49, 50, 51, 52, 53, 54, 55, 56, 57, 58, 59, 60, 61, 62, 65, 66, 67, 68, 70, 72, 73, 74, 75, 76, 78.

EXAMPLE S

The test compounds were dissolved in acetone in an amount equal to 3% of the final volume and then suspended at a concentration of 200 ppm in purified water containing 250 ppm of the surfactant Trem 14 (polyhydric alcohol esters). This suspension was sprayed to the point of run-off on wheat seedlings. The following day the seedlings were inoculated with a spore suspension of *Plasmopara viticola* (the causal agent of grape downey mildew) and incubated in a saturated atmosphere at 20° C. for 24 hours, and then moved to a growth chamber at 20° C. for 6 days, and then incubated in a saturated atmosphere at 20° C. for 24 hours, after which disease ratings were made. Of the compounds tested, the following gave 70% disease control or higher when tested at 40 ppm: 1, 6, 15, 17, 18, 19, 20, 22, 25, 30, 32, 35, 36, 38, 40, 41, 49, 52, 54, 55, 56, 57, 58, 59, 60, 61, 62, 65, 73, 74, 75, 76, 78.

What is claimed is:

1. A compound of the formula:

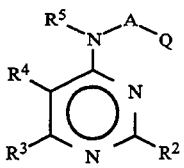

wherein:

Q is selected from the group

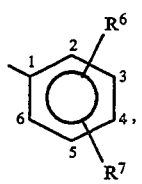 Q-1

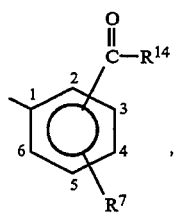 Q-2

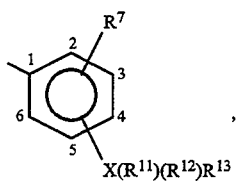 Q-3

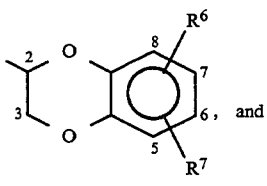 Q-5

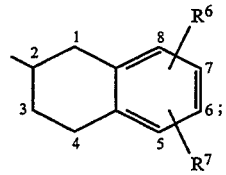 Q-6

A is selected from the group $C_1$-$C_5$ alkylene and $C_3$-$C_6$ cycloalkylene, where any one atom of A can be optionally substituted with $R^1$;

X is Si or Ge;

$R^1$ is selected from the group $C_1$-$C_2$ haloalkyl, CN, $C(O)R^8$, $CO_2R^8$, $C(O)N(R^8)R^9$, $N_3$, $NO_2$, $N(R^8)R^9$, $N(R^8)C(O)R^9$, $N(R^8)C(O)N(R^{10})R^9$, $N(R^8)S(O_2R^{10}$, $OR^8$, $OC(O)R^8$, $OCO_2R^8$, $OC(O)N(R^8)R^9$, $OS(O)_2R^8$, $SR^8$, $S(O)$ $R^8$, $S(O)_2R^8$ and SCN; provided that when $R^1$ is $N(R^8)S(O)_2R^{10}$, then $R^{10}$ is other than H and when $R^1$ is $OC(O)R^8$, $OCO_2R^8$, $OS(O)_2R^8$, $S(O)R^8$ or $S(O)_2R^8$, then $R^8$ is other than H;

$R^2$ is selected from the group H, halogen, $C_1$-$C_4$ alkyl and $C_1$-$C_4$ haloalkyl;

$R^3$ is selected from the group H, halogen, $C_1$-$C_6$ alkyl, $C_1$-$C_6$ haloalkyl, $C_2$-$C_6$ alkoxyalkyl and $C_2$-$C_6$ alkylthioalkyl;

$R^4$ is selected from the group halogen, $C_1$-$C_6$ alkyl, $C_1$-$C_6$ haloalkyl, $C_2$-$C_6$ alkoxyalkyl and $C_2$-$C_6$ alkylthioalkyl;

$R^5$ is selected from the group H, HCO, $C_2$-$C_6$ alkoxyalkyl $C_2$-$C_6$ alkylcarbonyl, $C_2$-$C_6$ alkoxycarbonyl, $C_2$-$C_6$ haloalkoxycarbonyl, $C(O)$ $R^{15}$, $R^{11}OC(O)N(R^{12})S$—, $R^{11}(R^{12})NS$—, and $SR^8$; or $R^5$ is $C_1$-$C_6$ alkyl optionally substituted with a group selected from halogen, CN, $NO_2$, $S(O)_nR^{11}$, $C(O)R^{11}$, $CO_2R^{11}$, $C_1$-$C_3$ haloalkoxy and phenyl optionally substituted by halogen, CN, or $C_1$-$C_2$ haloalkyl;

$R^6$ is selected from the group H, $C_1$-$C_6$ alkyl, $C_1$-$C_6$ alkoxy, $C_2$-$C_6$ alkoxyalkyl, $C_2$-$C_6$ alkoxyalkoxy, $C_2$-$C_6$ alkenyl, $C_2$-$C_6$ haloalkenyl, $C_2$-$C_6$ alkynyl, $C_2$-$C_6$ alkenyloxy, $C_2$-$C_6$ alkynyloxy, $C_3$-$C_6$ cycloalkyl, $C_3$-$C_6$ cycloalkylalkyl, $C_1$-$C_6$ alkylthio, $C_1$-$C_6$ alkylsulfinyl, $C_1$-$C_6$ alkylsulfonyl, $C_1$-$C_6$ haloalkylthio, $C_1$-$C_6$ haloalkylsulfinyl, $C_1$-$C_6$ haloalkylsulfonyl, phenyl optionally substituted with W and phenoxy optionally substituted with W;

$R^7$ is selected from the group H, halogen, CN, $NO_2$, $C_1$-$C_2$ alkyl, $C_1$-$C_2$ alkoxy and $CF_3$;

$R^8$ and $R^{10}$ are independently selected from the group H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_3$-$C_6$ haloalkynyl, $C_2$-$C_6$ alkoxyalkyl, $C_2$-$C_6$ alkylthioalkyl, $C_1$-$C_6$ nitroalkyl, $C_2$-$C_6$ cyanoalkyl, $C_3$-$C_8$ alkoxycarbonylalkyl, $C_3$-$C_6$ cycloalkyl, $C_3$-$C_6$ halocycloalkyl, phenyl optionally substituted with 1 to 3 substituents independently selected from W and benzyl optionally substituted with 1 to 3 substituents independently selected from W;

$R^9$ is selected from the group H and $C_1$-$C_4$ alkyl;

$R^8$ and $R^9$ can be taken together when attached to the same atom as —$(CH_2)_4$—, —$(CH_2)_5$— or —$CH_2CH_2OCH_2CH_2$—;

$R^{11}$ and $R^{12}$ are independently selected from the group $C_1$-$C_4$ alkyl;

$R^{13}$ is selected from the group $C_1$-$C_4$ alkyl, $C_1$-$C_4$ alkoxyalkyl and phenyl optionally substituted with W;

$R^{14}$ is selected from the group $C_1$-$C_6$ alkyl, $C_1$-$C_6$ alkoxy, $C_1$-$C_6$ haloalkoxy, and phenyl or benzyl, each phenyl and benzyl optionally and independently substituted with 1 to 3 W;

$R^{15}$ is selected from the group

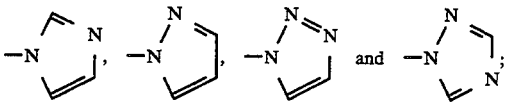

W is selected from the group halogen, CN, $NO_2$, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio, $C_1$-$C_2$ haloalkylthio, $C_1$-$C_2$ alkylsulfonyl and $C_1$-$C_2$ haloalkylsulfonyl; and n is 0, 1 or 2;

provided that:

(i) when Q is Q-1 and A is $C_1$-$C_5$ alkylene, then A is substituted with $R^1$;

(ii) when Q is Q-1, A is $C_1$-$C_5$ alkylene and $R^1$ is $OR^8$ or $SR^8$, then $R^8$ is other than $C_1$-$C_6$ alkyl;

(iii) when Q is Q-1 and A is $C_1$-$C_5$ alkylene, then $R^1$ is other than $C_1$-$C_2$ haloalkyl; and (iv) when Q is Q-1, R2 is chlorine, $R^3$ is H, $R^4$ is fluorine, $R^5$ is H and $R^6$ and $R^7$ are H, then A is other than $C_2$ alkylene substituted with $CO_2H$.

2. A compound according to claim 1 wherein:

A is $C_1$-$C_5$ alkylene;

$R^1$ is selected from the group $OR^8$, $OC(O)R^8$ and $SR^8$;

$R^2$ is H;

$R^3$ is $C_1$-$C_6$ alkyl;

$R^4$ is halogen;

$R^5$ is selected from the group H and $CH_3$;

$R^6$ is selected from the group $C_1$-$C_6$ alkyl, $C_2$-$C_6$ alkoxyalkyl, $C_2$-$C_6$ alkoxyalkoxy and phenoxy optionally substituted with W;

$R^7$ is selected from the group H, halogen and $C_1$-$C_2$ alkyl;

$R^8$ is selected from the group H and $C_1$-$C_4$ alkyl;

$R^{11}$, $R^{12}$ and $R^{13}$ are independently selected from $C_1$-$C_2$ alkyl;

$R^{14}$ is selected form the group $C_1$-$C_4$ alkyl, $C_1$-$C_4$ alkoxy and phenyl each optionally substituted with 1 to 3 W; and W is selected from the group halogen and $C_1$-$C_2$ haloalkyl.

3. A compound according to claim 2 wherein Q is Q-1.

4. A compound according to claim 2 wherein Q is Q-2.

5. A compound according to claim 2 wherein Q is Q-3.

6. A compound according to claim 2 wherein Q is Q-4.

7. A compound according to claim 2 wherein Q is Q-5.

8. A compound according to claim 2 wherein Q is Q-6.

9. A compound according to claim 2 wherein Q is Q-7.

10. An insecticidal, acaricidal and fungicidal composition comprising an effective amount of a compound according to any one of claims 1 to 9 and a carrier therefor.

11. A method for controlling insects, acarids and fungi comprising applying to them or to their environment an effective amount of a compound according to any one of claims 1 to 9.

12. A compound according to claim 3: β-[(5-chloro-6-ethyl-4-pyrimidinyl)amino]-4-(1,1-dimethylethyl)-benzenepropanol.

13. A compound according to claim 5: 5-chloro-6-ethyl-N-[2-[4-(trimethylsilyl)phenyl]ethyl]-4-pyrimidinamine.

14. A compound according to claim 5: 5-chloro-6-ethyl-N-[1-[4-(trimethylsilyl)phenyl]ethyl]-4-pyrimidinamine.

15. A compound according to claim 5: 5-chloro-6-ethyl-N-methyl-N-[2-[4-trimethylsilyl)phenyl]-ethyl]-4-pyrimidinamine.

16. A compound according to claim 5: 5-chloro-6-ethyl-N-[2-[3-(trimethylsilyl)phenyl]-ethyl]-4-pyrimidinamine.

17. A compound according to claim 6: 5-chloro-6-ethyl-N-[2-(2-naphthalenyl)ethyl]-4-pyrimidinamine.

18. A pesticidal composition comprising a compound according to any one of claims 1 to 17 and a carrier therefor.

19. A method for controlling pests comprising applying to them or to their environment a pesticidally effective amount of a compound according to any one of claims 1 to 17.

* * * * *